(12) United States Patent
Lefrancois et al.

(10) Patent No.: US 9,365,630 B2
(45) Date of Patent: *Jun. 14, 2016

(54) COMPOSITIONS AND METHODS FOR IMMUNOMODULATION IN AN ORGANISM

(71) Applicant: University of Connecticut, Farmington, CT (US)

(72) Inventors: Leo Lefrancois, West Hartford, CT (US); Thomas A. Stoklasek, Bristol, CT (US)

(73) Assignee: University of Connecticut, Farmington, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/567,317

(22) Filed: Dec. 11, 2014

(65) Prior Publication Data

US 2015/0093357 A1 Apr. 2, 2015

Related U.S. Application Data

(62) Division of application No. 13/368,605, filed on Feb. 8, 2012, now Pat. No. 8,940,288, which is a division of application No. 11/435,497, filed on May 17, 2006, now Pat. No. 8,124,084.

(60) Provisional application No. 60/681,663, filed on May 17, 2005.

(51) Int. Cl.

| C07K 14/54 | (2006.01) |
| C07K 14/715 | (2006.01) |
| A61K 38/17 | (2006.01) |
| A61K 38/20 | (2006.01) |
| C07K 14/55 | (2006.01) |
| C07K 1/02 | (2006.01) |
| C07K 16/00 | (2006.01) |

(52) U.S. Cl.
CPC ......... *C07K 14/5443* (2013.01); *A61K 38/1793* (2013.01); *A61K 38/2086* (2013.01); *C07K 1/02* (2013.01); *C07K 14/55* (2013.01); *C07K 14/7155* (2013.01); *C07K 16/00* (2013.01); *C07K 2317/52* (2013.01); *C07K 2319/02* (2013.01); *C07K 2319/30* (2013.01); *C07K 2319/31* (2013.01)

(58) Field of Classification Search
None
See application file for complete search history.

(56) References Cited

U.S. PATENT DOCUMENTS

| 5,552,303 | A | 9/1996 | Grabstein et al. |
| 5,574,138 | A | 11/1996 | Grabstein et al. |
| 5,965,726 | A | 10/1999 | Pavlakis et al. |
| 5,972,596 | A | 10/1999 | Pavlakis et al. |
| 6,001,973 | A | 12/1999 | Strom et al. |
| 6,063,911 | A | 5/2000 | Vournakis et al. |
| 6,174,666 | B1 | 1/2001 | Pavlakis et al. |
| 6,291,664 | B1 | 9/2001 | Pavlakis et al. |
| 6,414,132 | B1 | 7/2002 | Pavlakis et al. |
| 6,451,308 | B1 | 9/2002 | Strom et al. |
| 6,548,065 | B1 | 4/2003 | Anderson et al. |
| 6,764,836 | B2 | 7/2004 | Anderson et al. |
| 6,787,132 | B1 | 9/2004 | Gabizon et al. |
| 6,794,498 | B2 | 9/2004 | Pavlakis et al. |
| 6,864,245 | B2 | 3/2005 | Vournakis et al. |
| 6,998,476 | B2 | 2/2006 | Strom et al. |
| 7,067,132 | B2 | 6/2006 | Grabstein et al. |
| 7,112,436 | B1 | 9/2006 | Rose-John |
| 7,258,853 | B2 | 8/2007 | Strom et al. |
| 7,435,596 | B2 | 10/2008 | Campana et al. |
| 7,638,604 | B2 | 12/2009 | Li et al. |
| 7,858,081 | B2 | 12/2010 | Bernard et al. |
| 8,124,084 | B2 | 2/2012 | Lefrancois et al. |
| 8,163,879 | B2 | 4/2012 | Wong et al. |
| 8,224,578 | B2 | 7/2012 | Raab et al. |
| 8,492,118 | B2 | 7/2013 | Wong et al. |
| 8,507,222 | B2 | 8/2013 | Wong et al. |
| 8,940,288 | B2 | 1/2015 | Lefrancois et al. |
| 2002/0022030 | A1 | 2/2002 | Marrack et al. |
| 2002/0127201 | A1 | 9/2002 | Boussiotis et al. |
| 2002/0182178 | A1 | 12/2002 | Grooten et al. |

(Continued)

FOREIGN PATENT DOCUMENTS

| CA | 2625694 | 4/2007 |
| EP | 1777294 A1 | 4/2007 |

(Continued)

OTHER PUBLICATIONS

Alpdogan et al., 2005, "IL-7 and IL-15: therapeutic cytokines for Immunodeficiency", Trends Immunol; 26:56-64.

(Continued)

*Primary Examiner* — Ruixiang Li

(74) *Attorney, Agent, or Firm* — David A. Carpenter

(57) ABSTRACT

The present invention relates to a therapeutic polypeptide and methods for its creation and use for modulating an immune response in a host organism in need thereof. In particular, the invention relates to the administration to an organism in need thereof, of an effective amount of a pre-coupled polypeptide complex comprising a lymphokine polypeptide portion, for example IL-15 (SEQ ID NO: 5, 6), IL-2 (SEQ ID NO: 10, 12) or combinations of both, and an interleukin receptor polypeptide portion, for example IL-15Ra (SEQ ID NO: 7, 8), IL-2Ra (SEQ ID NO: 9, 11) or combinations of both, for augmenting the immune system in, for example, cancer, SCID, AIDS, or vaccination; or inhibiting the immune system in, for example, rheumatoid arthritis, or Lupus. The therapeutic complex of the invention surprisingly demonstrates increased half-life, and efficacy in vivo.

25 Claims, 12 Drawing Sheets

(56) References Cited

U.S. PATENT DOCUMENTS

| | | | |
|---|---|---|---|
| 2003/0105295 | A1 | 6/2003 | Strom et al. |
| 2004/0087015 | A1 | 5/2004 | Vournakis et al. |
| 2004/0170604 | A1 | 9/2004 | Ekida et al. |
| 2004/0253587 | A1 | 12/2004 | Grabstein et al. |
| 2005/0032167 | A1 | 2/2005 | Anderson et al. |
| 2005/0042220 | A1 | 2/2005 | Li et al. |
| 2006/0057680 | A1 | 3/2006 | Zheng et al. |
| 2006/0093605 | A1 | 5/2006 | Campana et al. |
| 2006/0104945 | A1 | 5/2006 | Choi |
| 2006/0147419 | A1 | 7/2006 | Perera et al. |
| 2006/0165668 | A1 | 7/2006 | Liu et al. |
| 2006/0257361 | A1 | 11/2006 | Watanabe et al. |
| 2006/0263857 | A1 | 11/2006 | Lefrancois et al. |
| 2007/0110714 | A1 | 5/2007 | Hayashi |
| 2007/0134718 | A1 | 6/2007 | Grooten et al. |
| 2007/0141557 | A1 | 6/2007 | Raab et al. |
| 2007/0160578 | A1 | 7/2007 | Waldmann et al. |
| 2008/0255039 | A1 | 10/2008 | Bernard et al. |
| 2009/0082299 | A1 | 3/2009 | Felber et al. |
| 2009/0238791 | A1 | 9/2009 | Jacques et al. |
| 2011/0081311 | A1 | 4/2011 | Pavlakis et al. |
| 2011/0158938 | A1 | 6/2011 | Bernard et al. |
| 2012/0230946 | A1 | 9/2012 | Wong et al. |
| 2014/0134128 | A1 | 5/2014 | Wong et al. |

FOREIGN PATENT DOCUMENTS

| | | |
|---|---|---|
| WO | WO 95/27722 A1 | 10/1995 |
| WO | WO 95/30695 A1 | 11/1995 |
| WO | WO 96/37223 A1 | 11/1996 |
| WO | WO 97/41232 A1 | 11/1997 |
| WO | WO 98/36768 A1 | 8/1998 |
| WO | WO 00/36918 A1 | 6/2000 |
| WO | WO 01/80889 A1 | 11/2001 |
| WO | WO 02/22805 A2 | 3/2002 |
| WO | WO 03/092737 A1 | 11/2003 |
| WO | WO 2004/059556 A1 | 7/2004 |
| WO | WO 2005/085282 A1 | 9/2005 |
| WO | WO 2006/020849 A2 | 2/2006 |
| WO | WO 2006/089064 | 8/2006 |
| WO | WO 2007/001677 A2 | 1/2007 |
| WO | WO 2007/046006 A2 | 4/2007 |
| WO | WO 2007/084342 A2 | 7/2007 |
| WO | WO 2007/095643 A2 | 8/2007 |
| WO | WO 2008/089144 A2 | 7/2008 |
| WO | WO 2008/143794 A1 | 11/2008 |
| WO | WO 2009/002562 A2 | 12/2008 |
| WO | WO 2011/020047 A1 | 2/2011 |
| WO | WO 2012/040323 A2 | 3/2012 |
| WO | WO 2012/175222 A1 | 12/2012 |

OTHER PUBLICATIONS

Alpdogan et al., 2005, "Interleukin-15 enhances immune reconstitution after allogenic bone marrow transplantation.", Blood; 105:865-873.

Altman, et al., 1996, "Phenotypic analysis of antigen-specific T lymphocytes", Science; 274:94-96.

Anderson et al., 1995, "Functional characterization of the human interleukin-15 receptor alpha chain and close linkage of IL15RA and IL2RA genes", Journal of Biological Chemistry; 270(50):29862-29869, Table 1, p. 29865.

Armitage et al., 1995, "IL-15 has stimulatory activity for the induction of B cell proliferation and differentiation", J. Immunol; 154:483-490.

Ausubel et al., 1993, Current Protocols in Molecular Biology, John Wiley & Sons, pp. 2.10.1-2.10.16.

Baccala, 2005, "Tumor immunity via homeostatic T cell proliferation: mechanistic aspects and clinical perspectives", Springer Semin Immunopathol published online.

Badoual et al., 2008, "The soluble alpha chain of interleukin-15 receptor: a proinflammatory molecule associated with tumor progression in head and neck cancer," Cancer Res; 68(10):3907-3914.

Bamford et al., 1994, "The interleukin (IL)-2 receptor-beta chain is shared by 11-2 and a cytokine, provisionally designated ii-t, that stimulates Tcell proliferation and the induction of lymphokine-activated killer-cells", Proceedings of the National Academy of Sciences USA; 91:4940-4944.

Bamford et al., 1996, "Interleukin (IL)15/IL-T production by the adult T-cell leukemia cell line HuT-102 is associated with a human T-cclilymphotrophic virus type I region /IL-15 fusion message that lacks many upstream AUGs that normally attenuates IL-15 mRNA translation", Proc. Natl. Acad. Sci. USA; 93:2897-2902.

Bamford et al., 1998, "The 5' untranslated region, signal peptide, and the coding sequence of the carboxyl terminus of IL-15 participate in its multifaceted translational control", Journal of Immunology; 160:4418-4426.

Barzegar et al., 1998, "IL-15 is produced by a subset of human melanomas, and is involved in the regulation of markers of melanoma progression through juxtacrine loops", Oncogene; 16(19):2503-2512.

Becker et al., 2002, "Interleukin 15 is required for proliferative renewal of virus-specific memory CD8 T cells", J Exp Med; 195:1541-1548.

Berard et al., 2003, "IL-15 promotes the survival of naive and memory phenotype CD8(+) T cells", Journal of Immunology; 170:5018-5026.

Bergamaschi et al., 2008, "Intracellular Interaction of Interleukin-15 with Its Receptor α during Production Leads to Mutual Stabilization and Increased Bioactivity", J. Biol. Chem.; 283(7):4189-4199.

Bergamaschi et al., 2012, "Circulating IL-15 exists as heterodimeric complex with soluble IL-15Rα in human and mouse serum", Blood; 120(1): e1-e8.

Berger et al., 2009, "Safety and immunologic effects of IL-15 administration in nonhuman primates," Blood; 114:2417-2426.

Bernard et al., 2004, "Identification of an interleukin-15α receptor-binding site on human interleukin-15," J Biol Chem; 279:24313-24322.

Bindon et al., 1983, "Clearance rates and systemic effects of intravenously administered interleukin 2 (IL-2) containing preparations in human subjects," Br. J. Cancer, 47:123-133.

Brocker, 1997, "Survival of mature CD4 T lymphocytes is dependent on major histocompatibility complex class II-expressina dendritic cells", J Exp Med; 186:1223-1232.

Budagian et al., 2004, "Reverse signaling throlJgh membrane-bound interleukin-15", J Biol Chem; 279:42192-42201.

Burkett et al, 2004, "Coordinate expression and trans presentation of interleukin (IL)-15Ralpha and IL-15 supports natural killer cell and memory CD8+ T cell homeostasis", J Exp Med; 200:825-834.

Burkett et al., 2003, "IL-15R alpha expression on CD8+ T cells is dispensable for T cell Memory", Proc Natl Acad Sci USA; 100:4724-4729.

Burton et al., 1994, "A lymphokine, provisionally designated interleukin-t and produced by a human adult T-cell leukemia line, stimulates T-cell proliferation and the induction of lymphokine-activated killer-cells", Proc Natl Acad Sci USA; 91:4935-4939.

Carson et al., 1994, "Interleukin (IL) 15 is a novel cytokine that activates human natural killer cells via components of the IL-2 receptor", J Exp Med; 180:1395-1403.

Castelli et al., 2004, "Mature dendritic cells can enhance CD8+ cell noncytotoxic anti-HIV responses: the role of IL-15", Blood; 103:2699-2704.

Chapoval et al., 1998, "Combination chemotherapy and IL-15 administration induce permanent tumor regression in a mouse lung tumor model: NK and T cell-mediated effects antagonized by B cells", J Immunol; 161:6977-6984.

Cheever, 2008, "Twelve immunotherapy drugs that could cure cancers", Immunol Rev.; 222:357-368.

Chehimi et al., 1997, "IL-15 enhances immune functions during HIV infection", Journal of Immunology; 158(12):5978-5987.

Chertova et al., 2013, "Characterization and favorable in vivo properties of heterodimeric soluble IL-15•IL-15Rα cytokine compared to IL-15 monomer", J. Biol. Chem.; 288(25):18093-18103.

(56) References Cited

OTHER PUBLICATIONS

Chitnis et al., 2003, "Determinants of HIV-Specific CD8 T-cell responses in HIV-infected pediatric patients and enhancement of HIV-gagspecific responses with exogenous IL-15", Clin Irnrnunol; 107:36-45.
Cho et al., 2000, "Homeostasis-stimulated proliferation drives naive T cells to differentiate directly into memory T cells", J Exp Med; 192:549-556.
Cooper et al., 2002, "In vivo evidence for a dependence on interleukin 15 for survival of natural killer cells", Blood; 100:3633-3638.
Cui et al., 2014, "Characterization of the IL-15 niche in primary and secondary lymphoid organs in vivo", Proc. Natl. Acad. Sci. USA; 111(5):1915-1920.
Davis et al., 1991, "Reduction of Immunogenicity and Extension of Circulating Half-life of Peptides and Proteins," Peptide and Protein Drug Delivery, Marcel Deker Inc., New York, pp. 831-864.
De Jong et al., 1996, "Interaction of IL-15 with the shared IL-2 receptor beta and gamma c subunits. The IL-15/beta/gamma c receptor-ligand complex is less stable than the IL-2/beta/gamma c receptor-ligand complex", J Immunol; 156:1339-1348.
Dubois et al., 1999, "Natural splicing of exon 2 of human interleukin-15 receptor α-chain mRNA results in a shortened form with a distinct pattern of expression," J Biol Chem; 274:26978-26984.
Dubois et al., 2002, "IL-15R alpha recycles and presents IL-15 In trans to neighboring cells", Immunity; 17:537-547.
Dubois et al., 2008, "Preassociation of IL-15 with IL-15R alpha-IgG1-Fc enhances its activity on proliferation of NK and $CD8^+$/$CD44^{high}$ T cells and its antitumor action", J Immunol.;180(4):2099-2106.
Dudley et al., 2005, "Adoptive cell transfer therapy following nonmyeloablative but Iymphodepleting chemotherapy for the treatment of patients with refractory metastatic melanoma", J Clin Oncol; 23:2346-2357.
Dummer et al., 2002, "T cell homeostatic proliferation elicits effective antitumor autoimmunity", J Clin Invest; 110:185-192.
Dunne et al., 2001, "Selective expansion and partial activation of human NK cells and NK receptor-positive T cells by IL-2 and IL-15", J Immunol; 167-3129-3138.
EMBL Database accession No. BC074726, "*Homo sapiens* interleukin 15 receptor, alpha, transcript variant 1, m RNA (cDNA clone MGC:103798 IMAGE:30915179), complete cds", dated Aug. 4, 2004.
Epardaud et al., 2008, "Interleukin-15/interleukin-15Rα complexes promote destruction of established tumors by reviving tumor-resident CD8+ T cells," Cancer Res; 68:2972-2983.
European Search Report of EP application No. 13195495.0-1402, dated Mar. 28, 2014.
European Search Report of EP application No. 13195499.2-1402, dated Mar. 27, 2014.
Fehniger et al., 2001, "Interleukin 15: biology and relevance to human disease," Blood; 97:14-32.
Ferrari-Lacraz et al., 2004, "Targeting IL-15 receptor-bearing cells with an antagonist mutant IL-15/Fc protein prevents disease development and progression in murine collagen-induced arthritis", J Immunol; 173:5818-5826.
Fewkes ct al., 2010, "Novel gamma-chain cytokincs as candidate immunc modulators in immune therapies for cancer," J Cancer; 16:392-398.
Fischer et al., 1997, "A bioactive designer cytokine for human hematopoietic progenitor cell expansion", Nat Biotechnol; 15(2):142-145.
Forcina ct al., 2004, "Interleukin-15 modulates interferon-gamma and bctachemokine production in patients with HIV infection: implications for immune-based therapy", Cytokine; 25:283-290.
Giri et al., 1994, "Utilization of the beta and gamma chains of the IL-2 receptor by the novel cytokine IL-15", EMBO J; 13:2822-2830.
Giri et al., 1995, "Identification and cloning of a novel IL-15 binding protein that is structurally related to the alpha chain of the IL-2 receptor", EMBO J; 15:3654-3633.
Giri et al., 1995, "IL-15, a novel T cell growth factor that shares activities and receptor components with IL-2", J Leukocyte Biol; 57:763-766.
Giron-Michel et al., 2005, "Membrane-bound and soluble IL-15/IL-15Rα complexes display differential signaling and functions on human hematopoietic progenitors," Blood; 106:2302-2310.
Goldrath et al., 2002, "Cytokine requirements for acute and basal homeostatic proliferation of naive and memory CD8+ T cells", J Exp Med; 195:1515-1522.
Goldrath et al., 2000, "Low-affinity ligands for the TCR drive proliferation of mature CD8+ Tcells in lymphopenic hosts", Immunity; 11:183-190.
Grabstein et al., 2004, "Cloning of a T cell growth factor that interacts with the beta chain of the interleukin-2 receptor", Science; 264:965-968.
Hsu et al., 2005, "Primary human T lymphocytes engineered with a codon-optimized IL-15 gene resist cytokine withdrawal-induced apoptosis and persist long-term in the absence of exogenous cytokine", J Immunol; 175:7226-7234.
International Preliminary Report on Patentablility of International application No. PCT/US2008/008084, dated Jan. 5, 2010.
International Search Report of International application No. PCT/US2006/19403, dated May 11, 2007.
International Search Report of International application No. PCT/US2008/008084, dated Dec. 30, 2008.
International Search Report on International application No. PCT/US2013/066424, dated May 8, 2014.
Jalah et al., 2007, "Efficient systemic expression of bioactive IL-15 in mice upon delivery of optimized DNA expression plasmids", DNA and Cell Biology; 26(12):827-840.
Jensen et al., 2012, "Structural analysis of N- and O-glycans released from glycoproteins", Nature Protocols, 7(7):1299-1310.
Johnston et al., 1995, "Tyrosine phosphorylation and activation of STAT5, STAT3, and Janus kinases by interleukins 2 and 15", Proc Natl Acad Sci U S A. 92(19):8705-8709.
Judge et al., 2002, "Interleukin 15 controls both proliferation and survival of a subset of memory-phenotype CD8(+) T Cells", J Exp Med; 196:935-946.
Jung et al., 2002, "In vivo depletion of CD11c(+) dendritic cells abrogates priming of CD8(+) T cells by exogenous cell-associated antigens", Immunity; 17:211-220.
Kassiotis et al., 2002, "Impairment of immunological memory in the absence of MHC despite survival of memory T cells", Nat Immunol; 3:244-250.
Kennedy et al., 2000, "Reversible defects in natural killer and memory CD8 T cell lineages in Interleukin-15-deficient mice", J Exp Med; 191:771-780.
Khan et al., 1996, "IL-15 augments CD8+ T cell-mediated immunity against Toxoplasma gondii infection in mice", J Immunol; 157(5):2103-2108.
Khan et al., 2002, "Treatment with soluble interleukin-15Rα exacerbates intracellular parasitic infection by blocking the development of memory CD8+ T cell response," J Exp Med; 195(11):1463-1470.
Kieper et al., 2000, "Homeostatic expansion and phenotypic conversion of naive T cells in response to self peptide/MHC ligands", PNAS; 96:13306-13311.
Kim et al., 1998, "Generation of mucosal cytotoxic T cells against soluble protein by tissue specific environmental and costimulatory signals", Proc Natl Acad Sci USA; 95:10814-10819.
Kishimoto, 2010, "IL-6: from its discovery to clinical applications", International Immunology; 22(5):347-352.
Klebanoff et al., 2004, "IL-15 enhances the in vivo antitumor activity of tumorreactive CD8+ T cells", Proc Natl Acad Sci USA; 101:1969-1974.
Kobayashi et al., 2000, "Differences in biodistribution, pharmacokinetics, and tumor targeting between interleukins 2 and 15", Cancer Research; 60:3577-3583.
Kobayashi et al., 2005, "Role of trans-cellular IL-15 presentation in the activation of NK cell-mediated killing, which leads to enhanced tumor immunosurveillance", Blood; 105(2): 721-727.
Koka et al., 2003, "Interleukin (IL)-15R[alpha]-deficient natural killer cells survive in normal but not IL-15R[alpha]-deficient mice", J Exp Med; 197:977-984.

(56) References Cited

OTHER PUBLICATIONS

Krause et al., 1996, "Genomic structure and chromosomal localization of the human interleukin 15 gene (IL-15)", Cytokine. 8(9):667-674.
Ku et al., 2000, "Control of homeostasis of CD8+ memory T cells by opposing cytokines", Science; 288:675-678.
Kutzler et al., 2005, "Coimmunization with an optimized IL-15 plasmid results in enhanced function and longevity of CD8 T cells that are partially independent of CD4 T cell help," J Immunol; 175:112-123.
Lodolce et al., 1998, "IL-15 receptor maintains lymphoid homeostasis by supporting lymphocyte homing and proliferation", Immunity; 9:669-676.
Lodolce et al., 2001, "T cell independent interleukin 15R alpha signals are required for bystander proliferation", J Exp Med; 194:1187-1194.
Lum et al., 2004, "Differential Effects of Interleukin-7 and Interleukin-15 on NK Cell Anti-Human Immunodeficiency Virus Activity", J Viral; 78:6033-6042.
Lyons et at, 1994, "Determination of lymphocyte division by flow cytometry", J Immunol Methods. 2;171(1):131-137.
Maeurer et al., 2000, "Interleukin-7 or interleukin-15 enhances survival of mycobacterium tuberculosis-infected mice", Infect Immun; 68:2962-2970.
Masopust et al., 2001, "Direct analysis of the dynamics of the intestinal mucosa CD8 T cell response to systemic virus infection", J Immunol; 166:2348-2356.
Mastroianni et al., 2000, "Interleukin-15 enhances neutrophil functional activity in patients with human immunodeficiency virus infection", Blood; 96:1979-1984.
Matsumoto et al., 2003, "On-column refolding and characterization of soluble human interleukin-15 receptor alpha-chain produced in *Escherichia coli*", Protein Expr Purif; 31(1):64-71.
Mlecnik et al., 2014, "Functional network pipeline reveals genetic determinants associated with in situ lymphocyte proliferation and survival of cancer patients", Sci Transl Med.; 6(228):228ra37.
Mortier et al., 2004, "Natural, proteolytic release of a soluble form of human IL-15 receptor α-chain that behaves as a specific, high affinity IL-15 antagonist," J of Immunol; 173:1681-1688.
Mortier et al., 2006, "Soluble interleukin-15 receptor α (IL-15Rα)-sushi as a selective and potent agonist of IL-15 action through IL-15R β/γ. Hyperagonist IL-15 × IL-15Rα fusion proteins," J Biol Chem; 281:1612-1619.
Mueller et al., 2003, "IL-15 enhances survival and function of HIV-specific CD8+ T cells", Blood; 101(3):1024-1029.
Murali-Krishna et al., 1999, "Persistence of memory CD8 T cells in MHC class I-deficient mice", Science; 286:1377-1381.
Nasioulas et al., 1994, "Elements distinct from human immunodeficiency virus type 1 splice sites are responsible for the Rev dependence of *env* mRNA", J Virol, 68(5):2986-2993.
Nguyen et al., 2000, "TNF receptor 1 (TNFR1) and CD95 are not required for T cell deletion after virus infection but contribute to peptide-induced deletion under limited conditions", Eur J Immunol; 30:683-688.
Nishimura et al., 2005, "A novel autoregulatory mechanism for transcriptional activation of the IL-15 gene by a nonsecretable isoform of IL-15 generated by alternative splicing", FASEB J; 19:19-28.
Notice of Allowance and Fees Due of U.S. Appl. No. 11/435,497, dated Oct. 19, 2011.
Notice of Allowance and Fees Due of U.S. Appl. No. 13/368,605, dated Sep. 11, 2014.
Oehen et al., 1998, "Differentiation of naive CTL to effector and memory CTL: correlation of effector function with phenotype and cell division", J Immunol; 161;5338-5346.
Office Action of U.S. Appl. No. 11/435,497, dated Feb. 25, 2009.
Office Action of U.S. Appl. No. 11/435,497, dated Jan. 13, 2011.
Office Action of U.S. Appl. No. 11/435,497, dated Jun. 27, 2008.
Office Action of U.S. Appl. No. 11/435,497, dated Jun. 27, 2011.
Office Action of U.S. Appl. No. 11/435,497, dated Jun. 7, 2010.
Office Action of U.S. Appl. No. 11/435,497, dated Oct. 30, 2009.
Office Action of U.S. Appl. No. 13/368,605, dated Apr. 9, 2014.
Oh et al., 2003, "Coadministration of IIIVvaccine vectors with vaccinia viruses expressing IL-15 but not IL-2 induces long-lasting cellular immunity", PNAS; 100:3392-3397.
Oh et al., 2004, "IL-15/IL-15R{alpha}-mediated avidity maturation of memory CD8+ T cells", Proc Natl Acad Sci USA; 101:15154-15159.
Ohteki et al., 2001, "Critical role of IL-15-IL-15R for antigen-presenting cell functions in the innate immune response", Nat Immunol; 2:1138-1143.
Park et al., 2004, "Follicular dendritic cells produce IL-15 that enhances germinal center B cell proliferation in membrane-bound form", J Immunol; 173:6676-6683.
Pereno et al., 2000, "IL-15/IL-15Ralpha intracellular trafficking in human melanoma cells and signal transduction through the IL-15Ralpha", Oncogene. 19 (45):5153-5162.
Pettit et al., 1997, "Structure-function studies of interleukin 15 using site-specific mutagenesis, polyethylene glycol conjugation, and homology modeling", J Biol Chem; 272(4):2312-2318.
Pflanz et al., 1999, "A fusion protein of interleukin-11 and soluble interleukin-11 receptor acts as a superagonist on cells expressing gp130", FESB Lett; 450:117-122.
Porter et al., 2005, "T-cell reconstitution and expansion after hematopoietic stem cell transplantation: 'T' it up!", Bone Marrow Transplant; 35:935-942.
Prlic et al., 2003, "In vivo survival and homeostatic proliferation of natural killer cells", J Exp Med; 197:967-976.
Roychowdhury et al., 2004, "Failed adoptive immunotherapy with tumorspecific T cells: reversal with low-dose interleukin 15 but not low-dose interleukin 2", Cancer Res; 64:8062-8067.
Rubinstein et al., 2002, "Systemic administration of IL-15 augments the antigen-specific primary CD8+ T Cell response following vaccination with peptide-pulsed dendritic cells", J Immunol; 169:4928-4935.
Rubinstein et al., 2006, "Converting IL-15 to a superagonist by binding to soluble IL-15Rα," PNAS; 103(24):9166-9171.
Ruchatz et al., 1998, "Soluble IL-15 receptor alpha-chain administration prevents murine collagen-induced arthritis: a role for IL-15 in development of antigen-induced immunopathology", J Immunol; 160:5654-5660.
Ruckert et al., 2003, "Dendritic cell-derived IL-15 controls the induction of CD8 T cell immune responses", Eur J Immunol; 33:3493-3503.
Sandau et al., 2004, "Transpresentation of IL-15 by bone marrow-derived cells necessitates expression of IL-15 and IL-15R by the same cells", J Immunol; 173(11):6537-6541.
Sato et al., 2007, "The IL-15/IL-15 Rα on cell surfaces enables sustained IL-15 activity and contributes to the long survival of CD8 memory T cells", Proc Natl Acad Sci USA; 104(2):588-593.
Scheller et al., 2006, "Interleukin-6 and its receptor: from bench to bedside", Med Microbiol Immunol; 195:173-183.
Schluns et al., 2000, "Interleukin-7 mediates the homeostasis of naive and memory CD8 T cells in vivo", Nat Immunol; 1:426-432.
Schluns et al., 2002, "Cutting edge: requirement for IL-15 in the generation of primary and memory antigen specific CD8 T cells", J Immunol; 168:4827-4831.
Schluns et al., 2004, "Distinct cell types control lymphoid subset development by means of IL-15 and IL-15 receptor alpha expression", Proc Natl Acad Sci USA; 101:5616-5621.
Schluns et al., 2004, "Trans-regulation of memory CD8 T cell proliferation by IL-15Ra+ bone marrow-derived cells", Blood; 103(3):988-994.
Schluns et al., 2005, "The roles of interleukin-15 receptor α: Transpresentation, receptor component, or both?" Int J Biochem Cell Biol; 37:1567-1571.
Schneider et al., 1997, Inactivation of the human immunodeficiency virus type 1 inhibitory elements allows Rev-independent expression of Gag and Gag/protease and particle formation, J Virol, 71(7):4892-4903.
Schwartz et al., 1992, "Mutational inactivation of an inhibitory sequence in human immunodeficiency virus type 1 results in Rev-independent *gag* expression", J Virol, 66(12):7176-7182.

(56) References Cited

OTHER PUBLICATIONS

Smith et al., 2000, "Selective blockade of IL-15 by soluble IL-15 receptor alpha-chain enhances cardiac allograft survival", J Immunol; 165(6):3444-3450.
Southern and Berg, 1982, "Transformation of mammalian cells to antibiotic resistance with a bacterial gene under control of the SV40 early region promoter", J Mol Appl Genet, 1:327-341.
Stoklasek et al., 2006, "Combined IL-15/IL-15Rα immunotherapy maximizes IL-15 activity in vivo,", J of Immunol; 177(9):6072-6080.
Supplementary European Search Report of EP application No. 06784439.9-2401, dated Apr. 22, 2009.
Tagaya et al., 1997, "Generation of secretable and nonsecretable interleukin 15 isoforms through alternate usage of signal problems", Proc Natl Acad Sci USA, 94:14444-14449.
Tan et al., 2000, "Interleukin (IL)-15 and IL-7 jointly regulate homeostatic proliferation of memory phenotype CD8+ cells but are not required for memory phenotype CD4+ cells", J Exp Med; 195:1523-1532.
Tsunobuchi et al., 2000, "A protective role of interleukin-15 in a mouse model for systemic infection with herpes simplex virus," Virology, 275:57-66.
Umemura et al., 2001, "Overexpression of IL-15 in vivo enhances protection against *Mycobacterium bovis* bacillus Calmette-Guerin infection via augmentation of NK and T cytotoxic 1 responses", J Immunol; 167:946-956.
Van Belle et al., 2005, "IL-15 and IL-15Rα in CD4+ T cell immunity," Arch Immunol Ther Exp; 53(2):115-126.
Villinger et al., 2004, "IL-15 is superior to IL-2 in the generation of long-lived antigen specific memory CD4 and CD8 T cells in rhesus macaques", Vaccine; 22:3510-3521.
Waldmann et al., 1999, "The multifaceted regulation of interleukin-15 expression and the role of this cytokine in NK cell differentiation and host response to intracellular pathogens," Annu Rev Immunol., vol. 17:19-49.
Waldmann et al., 2001, "Contrasting roles of IL-2 and IL-15 in the life and death of lymphocytes: implications for immunotherapy," Immunity, vol. 14:105-110.
Waldmann, T.A., 2006, "The biology of interleukin-2 and interleukin-15: implications for cancer therapy and vaccine design," Nat Rev Immunol., vol. 6:595-601.
Wang et al., 1987, "The interleukin 2 receptor", Journal of Experimental Medicine; 166:1055-1069.
Warren et al., 1996, "Analysis of the costimulatory role of IL-2 and IL-15 in initiating proliferation of resting (CD56dim) human NK cells", J Immunol; 156:3254-3259.
Wei et al., 2001, "The Sushi domain of soluble IL-15 receptor α is essential for binding IL-15 and inhibiting inflammatory and allogenic responses in vitro and in vivo," J Immunol., vol. 167:277-282.
Williams et al., 2007, "T cell immune reconstitution following lymphodepletion", Seminars in Immunology; 19(5):318-330.
Written Opinion of International application No. PCT/US2006/19403, dated May 11, 2007.
Written Opinion of International application No. PCT/US2008/008084, dated Dec. 30, 2008.
Written Opinion on International application No. PCT/US2013/066424, dated May 8, 2014.
Wrzesinski et al., 2005, "Less is more: lymphodepletion followed by hematopoietic stem cell transplant augments adoptive T-cell-based antitumor immunotherapy", Curr Opin Immunol; 17:195-201.
Wysocka et al., 2004, "Enhancement of the host immune responses in cutaneous T-cell lymphoma by CpG oligodeoxynucleotides and IL-15", Blood; 104:4142-4149.
Zammit et al., 2005, "Dendritic cells maximize the memory CD8 T cell response to infection", Immunity 22(5):561-70.
Zeng et al., 2005, "Synergy of IL-21 and IL-15 in regulating CD8+ T cell expansion and Function", J Exp Med; 201:139-148.
Shanmugham et al., 2006, "IL-15 an immunoregulatory and anti-cancer cytokine. Recent advances", Journal of Experimental Cancer Research, 25(4):529-536.

Baker et al., 2001, "Metabolic control of recombinant protein N-glycan processing in NS0 and CHO cells", Biotechnol Bioeng, 73(3):188-202.
Bennett et al., 2012, "Control of mucin-type O-glycosylation: a classification of the polypeptide GaINAc-transferase gene family", Glycobiology, 22(6):736-756.
Beq et al., 2009, "Injection of glycosylated recombinant simian IL-7 provokes rapid and massive T-cell homing in rhesus macaques", Blood, 114(4):816-825.
Bergamaschi et al., 2009, "Secretion and biological activity of short signal peptide IL-15 is chaperoned by IL-15 receptor alpha in vivo", J Immunol, 183(5):3064-3072.
Bergamaschi et al., 2015, "Intramuscular delivery of heterodimeric IL-15 DNA in macaques produces systemic levels of bioactive cytokine inducing proliferation of NK and T cells", Gene Ther, 22(1):76-86.
Bosques et al., 2010, "Chinese hamster ovary cells can produce galactose-alpha-1,3-galactose antigens on proteins", Nat Biotechnol, 28(11):1153-1156.
Chamorey et al., 2002, "Impact of glycosylation on the effect of cytokines. A special focus on oncology", Eur Cytokine Netw, 13(2):154-160.
Chitlaru et al., 2002, "Overloading and removal of N-glycosylation targets on human acetylcholinesterase: effects on glycan composition and circulatory residence time", The Biochemical journal, 363(Pt 3):619-631.
Chitlaru et al., 1998, "Modulation of circulatory residence of recombinant acetylcholinesterase through biochemical or genetic manipulation of sialylation levels", The Biochemical journal, 336 (Pt 3):647-658.
Conlon, et al., 2015, Redistribution, hyperproliferation, activation of natural killer cells and CD8 T cells, and cytokine production during first-in-human clinical trial of recombinant human interleukin-15 in patients with cancer, J Clin Oncol, 33(1):74-82.
Croce et al., 2012, "Immunotherapeutic applications of IL-15", Immunotherapy 4(9):957-969.
Dissing-Olesen et al., 2008, "The function of the human interferon-beta 1a glycan determined in vivo", J Pharmacol Exp Ther, 326(1):338-347.
Diswall et al., 2010, "Structural characterization of alpha1,3-galactosyltransferase knockout pig heart and kidney glycolipids and their reactivity with human and baboon antibodies", Xenotransplantation, 17(1):48-60.
Eggleton et al., 2008, "Consequence of neo-antigenicity of the 'altered self'", Rheumatology (Oxford), 47(5):567-571.
Eisenman et al., 2002, "Interleukin-15 interactions with interleukin-15 receptor complexes: characterization and species specificity", Cytokine, 20(3):121-129 (2002).
Galili, 2005, "The alpha-gal epitope and the anti-Gal antibody in xenotransplantation and in cancer immunotherapy", Immunol Cell Biol, 83(6):674-686.
Geoghegan et al., 2013, "Unexpected mucin-type O-glycosylation and host-specific N-glycosylation of human recombinant interleukin-17A expressed in a human kidney cell line", Protein expression and purification, 87(1):27-34.
Harvey et al., 2009, "Application of negative ion MS/MS to the identification of N-glycans released from carcinoembryonic antigen cell adhesion molecule 1 (CEACAM1)", J Mass Spectrom, 44(1):50-60.
Lee et al., 2014, "Differential site accessibility mechanistically explains subcellular-specific N-glycosylation determinants", Frontiers in immunology, 5:1-13.
Leymarie et al., 2013, "Interlaboratory study on differential analysis of protein glycosylation by mass spectrometry: the ABRF glycoprotein research multi-institutional study 2012", Mol Cell Proteomics, 12(10):2935-2951.
Lugli et al., 2010, "Transient and persistent effects of IL-15 on lymphocyte homeostasis in nonhuman primates", Blood, 116(17):3238-3248.
Ma et al., 2006, Diverse functions of IL-2, IL-15, and IL-7 in lymphoid homeostasis, Annu Rev Immunol, 24:657-679.

(56) References Cited

OTHER PUBLICATIONS

Mysling et al., 2010, "Utilizing ion-pairing hydrophilic interaction chromatography solid phase extraction for efficient glycopeptide enrichment in glycoproteomics", Anal Chem, 82(13):5598-5609.
Nellis et al., 2012, "Characterization of recombinant human IL-15 deamidation and its practical elimination through substitution of asparagine 77", Pharm Res, 29(3):722-738.
Ring et al., 2012, "Mechanistic and structural insight into the functional dichotomy between IL-2 and IL-15", Nat Immunol, 13(12):1187-1195.
Rudd and Dwek, 1997, "Glycosylation: heterogeneity and the 3D structure of proteins", Critical reviews in biochemistry and molecular biology, 32(1):1-100.
Sethi et al., 2015, "In-depth N-glycome profiling of paired colorectal cancer and non-tumorigenic tissues reveals cancer-, stage- and EGFR-specific protein N-glycosylation", Glycobiology, 25(10):1064-78.
Sola and Griebenow, 2009, "Effects of glycosylation on the stability of protein pharmaceuticals", J Pharm Sci, 98(4):1223-1245.
Stavenhagen et al., 2013, "Quantitative mapping of glycoprotein micro-heterogeneity and macro-heterogeneity: an evaluation of mass spectrometry signal strengths using synthetic peptides and glycopeptides", J Mass Spectrom, 48(6):627-639.
Steentoft et al., 2013, "Precision mapping of the human O-GalNAc glycoproteome through SimpleCell technology", The EMBO journal, 32(10):1478-1488.
Sumer-Bayraktar et al., 2011, "N-glycans modulate the function of human corticosteroid-binding globulin", Mol Cell Proteomics, 10(8):M111.009100, doi:10.1074/mcp.M111.009100.
Sumer-Bayraktar et al., 2012, "Micro- and macroheterogeneity of N-glycosylation yields size and charge isoforms of human sex hormone binding globulin circulating in serum", Proteomics, 12(22):3315-3327.
Takahashi et al., 2009, "Core fucose and bisecting GlcNAc, the direct modifiers of the N-glycan core: their functions and target proteins", Carbohydrate research 344(12):1387-1390.
Takeuchi and Kobata, 1991, "Structures and functional roles of the sugar chains of human erythropoietins", Glycobiology, 1(4):337-346.
Thaysen-Andersen and Packer, 2012, "Site-specific glycoproteomics confirms that protein structure dictates formation of N-glycan type, core fucosylation and branching", Glycobiology, 22(11):1440-1452.
Thaysen-Andersen, et al., 2008, "Investigating the biomarker potential of glycoproteins using comparative glycoprofiling—application to tissue inhibitor of metalloproteinases-1", Biochim Biophys Acta, 1784(3):455-463.
Thaysen-Andersen et al., 2015, "Human neutrophils secrete bioactive paucimannosidic proteins from azurophilic granules into pathogen-infected sputum", J Biol Chem, 290(14):8789-8802.
Thaysen-Andersen et al., 2011, "Site-specific characterisation of densely O-glycosylated mucin-type peptides using electron transfer dissociation ESI-MS/MS", Electrophoresis, 32(24):3536-3545.
Tran and Ten Hagen, 2013, "Mucin-type O-glycosylation during development", J Biol Chem, 288(10):6921-6929.
Van Den Nieuwenhof et al., 2000, "Recombinant glycodelin carrying the same type of glycan structures as contraceptive glycodelin-A can be produced in human kidney 293 cells but not in chinese hamster ovary cells", Eur J Biochem, 267(15):4753-4762.
Venkatakrishnan et al., 2015, "Cystic fibrosis and bacterial colonization define the sputum N-glycosylation phenotype", Glycobiology, 25(1):88-100.
Vlasak et al., 2009, "Identification and characterization of asparagine deamidation in the light chain CDR1 of a humanized IgG1 antibody", Anal Biochem, 392(2):145-154.
Waldmann et al., 2011, "Safety (toxicity), pharmacokinetics, immunogenicity, and impact on elements of the normal immune system of recombinant human IL-15 in rhesus macaques", Blood, 117(18):4787-4795.
Weintraub and Deverman, 2007, "Chronoregulation by asparagine deamidation", Sci STKE, 2007(409):re7, doi:10.1126/stke.4092007re7.
Yan et al., 1993, "Novel Asn-linked oligosaccharides terminating in GalNAc beta (1→4)[Fuc alpha (1→3)]GlcNAc beta (1→•) are present in recombinant human protein C expressed in human kidney 293 cells", Glycobiology, 3(6):597-608.
Yang, et al., 2012, "Structures and biosynthesis of the N- and O-glycans of recombinant human oviduct-specific glycoprotein expressed in human embryonic kidney cells", Carbohydrate Research, 358, 47-55.
Yoo, et al., 2002, "Myeloma expression systems", J Immunol Methods 261(1-2):1-20.
Zeck, et al., 2011, "Cell type-specific and site directed N-glycosylation pattern of FcgammaRIIIa", Journal of Proteome Research, 10(7):3031-3039.
Zhang et al., 1998, "Potent and selective stimulation of memory-phenotype CD8+ T cells in vivo by IL-15", Immunity, 8(5):591-599.
Zhao et al., 2007, "DNA damage-induced Bcl-xL deamidation is mediated by NHE-1 antiport regulated intracellular pH", PLoS Biol, 5(1):e1, doi:10.1371/journal.pbio.0050001.

Figure 11.

Liver Nodule Counts

| | Control | IL-15 | IL-15 & IL-15Rα |
|---|---|---|---|
| m1 | 200+ | 34 | 2 |
| m2 | 91 | 74 | 19 |
| m3 | 200+ | 136 | 5 |
| m4 | 200+ | 23 | 6 |
| m5 | 105 | 33 | 6 |
| avg | ~160+ | ~60 | ~8 |

Spleen Weight (g)

| | Control | IL-15 | IL-15 & IL-15Rα |
|---|---|---|---|
| m1 | 1.73 | 1.67 | 0.24 |
| m2 | 1.18 | 1.55 | 0.45 |
| m3 | 0.80 | 0.43 | 0.49 |
| m4 | 1.50 | 1.18 | 0.56 |
| m5 | 2.17 | 1.14 | 0.43 |
| avg | ~1.50 | ~1.19 | ~0.43 |

COMPOSITIONS AND METHODS FOR IMMUNOMODULATION IN AN ORGANISM

CROSS-REFERENCE TO RELATED APPLICATIONS

This application is a divisional of U.S. application Ser. No. 13/368,605, filed Feb. 8, 2012, which is a divisional of U.S. application Ser. No. 11/435,497, filed May 17, 2006, now issued as U.S. Pat. No. 8,124,084, which claims the benefit under 35 U.S.C. §119(e) to of U.S. Provisional Patent Application No. 60/681,663, filed May 17, 2005, each of which is hereby incorporated by reference in its entirety.

STATEMENT REGARDING FEDERALLY SPONSORED RESEARCH

The U.S. Government has certain rights in this invention pursuant to Grant No.: R01-A151583 Role of IL-15 in CD8 T Cell Development and Response, awarded by the National Institutes of Health (NIH).

SEQUENCE LISTING

The present application hereby incorporates by reference, in its entirety, the Sequence Listing, and identical CRF of the Sequence Listing previously filed with the United States Patent and Trademark Office in association with U.S. Provisional Patent Application Ser. No. 60/681,663; filed: May 17, 2006; entitled: Compositions and Methods for Immunomodulation in an Organism. The CRF contains nucleotide and amino acid sequences, SEQ. ID NO. 1-16, in file: "IL-15_LLefrancois.txt;" created: May 17, 2005; OS: MS Windows XP; size: 31 KB. In accordance with 37 CFR 1.821(e) please use the earlier-filed computer readable form filed in that application as the computer readable form for the instant application. An identical paper copy of said Sequence Listing is submitted, herewith, in the instant application.

FIELD OF THE INVENTION

The present invention relates to a therapeutic polypeptide composition and methods of administration to an organism in need thereof for modulating immune function. In particular the invention relates to the administration of an effective amount of a therapeutic protein complex comprising a lymphokine polypeptide portion, and a lymphokine receptor portion that demonstrates improved in vivo half-life and efficacy when administered to an organism.

BACKGROUND

Lymphocytes are a type of white blood cell involved in immune system regulation. There are two broad categories of lymphocytes, namely T cells and B cells. T-cells are responsible for cell-mediated immunity whereas B-cells are responsible for humoral immunity (relating to antibodies). T-cells are named such because these lymphocytes mature in the thymus and B-cells mature in bone marrow. Lymphocytes are much more common in the lymphatic system, and include B cells, T cells, killer T-cells, and natural killer cells. B cells make antibodies that bind to pathogens to enable their destruction. CD4+ (helper) T cells co-ordinate the immune response (they are what become defective in an HIV infection). CD8+ (cytotoxic) T cells and Natural Killer (NK) cells are able to kill cells of the body that are infected by a virus or display an antigenic sequence.

Natural killer cells are CD56(+)CD3(−) large granular lymphocytes that constitute a key component of the human innate immune response. In addition to their potent cytolytic activity, NK cells express a host of immunoregulatory cytokines and chemokines that play a crucial role in pathogen clearance. Furthermore, interactions between NK and other immune cells are implicated in triggering the adaptive, or antigen-specific, immune response.

The interactions between immune and inflammatory cells are mediated in large part by cytokine proteins, for example, lymphokines such as interleukins (IL), which are able to promote cell growth, differentiation, and functional activation. Currently, at least twenty-three interleukins and their various splice variants have been described. Some of these cytokines mediate distinct biological effects but many have overlapping activities. The understanding of interleukin structure and function has led to new and important insights into the fundamental biology of immunity and inflammation. For example, Interleukin-2 (IL-2) and IL-15 are two distinct cytokines with partially overlapping properties that are implicated in the development, homeostasis, and function of T cells and NK cells.

IL-2, formerly referred to as T-cell growth factor, is a powerful immunoregulatory lymphokine that is produced by antigen-activated T cells. It is produced by mature T lymphocytes on stimulation but also constitutively by certain T-cell lymphoma cell lines. IL-2 is useful in the study of the molecular nature of T-cell differentiation, and because it augments natural killer cell activity, it can be useful in modulating the immune response to cancers, viral or bacterial infections. Also, IL-2 can act as a growth hormone for both B and T lymphocytes, and stimulates clonal expansion and maturation of these lymphocytes. IL-2 binds to its receptor (R) complex comprised of IL-2R alpha ("IL-2Ra"), IL-2R beta ("IL-2Rb"), and -gamma ("gC") chains, and exerts its effect via second messengers, mainly tyrosine kinases, which ultimately stimulate gene expression.

The heterotrimerization of the receptor chains leads to high affinity binding for IL-2. The functional importance of IL-2Ra in hematopoietic cell systems is well known. However, the potential role that IL-2Ra plays in tumorigenesis is still not fully elucidated. IL-2Ra expression has been found in many types of cancers, including leukemia, lymphoma, lung, breast, head-and-neck, and prostate. Also, high expression of IL-2Ra in tumors correlates with a poor prognosis for the patient.

IL-15 is a member of the four alpha-helix bundle family of lymphokines and its mRNA can be detected in a wide variety of tissues of both non-hematopoietic, and hematopoietic lineages but it is not produced by T cells. IL-15 is difficult to detect at the protein level in vivo perhaps due to short protein half-life and tight transcriptional and translational control. IL-15 is a soluble protein made by many cells in the body which play an important role in the development of the immune system. IL-15 was simultaneously discovered in an adult T-cell leukemia cell line and a simian kidney epithelial cell line as a 14 kDa-16 kDa protein able to stimulate cytotoxic T cell lymphocyte cell line (CTLL) and peripheral blood T cell proliferation, and to induce peripheral blood mononuclear cells to exhibit effector function.

IL-15 plays a multifaceted role in development and control of the immune system. More specifically, IL-15 influences the function, development, survival, and proliferation of CD8+ T cells, NK cells, killer T cells, B cells, intestinal intraepithelial lymphocytes (IEL) and antigen-presenting cells (APC). It has been demonstrated that both IL-15−/−, and IL-15Ra−/− transgenic mice lack peripheral NK and killer T cell populations, certain IEL subsets, and most memory phenotype CD8+ T cells. In addition, while antigen-specific memory CD8+ T cells can develop in response to pathogens in both types of knockout mice, the resulting memory CD8+ T cell pool undergoes dramatic erosion over time. Suggesting a crucial role for IL-15 in mediating long term memory CD8+ T cell proliferation and survival.

The IL-15 receptor (R) consists of three polypeptides, the type-specific IL-15R alpha ("IL-15Ra"), the IL-2/IL-15Rbeta ("IL-2Rb"), and the common gamma chain ("gC," which is shared by multiple cytokine receptors). The high affinity IL-15Ra chain ($K_d \approx 10^{11}$ M) is thought to form a heterotrimeric complex with the shared IL-2Rb, and the gC. Similar to IL-15, IL-15Ra is thought to be expressed by a wide variety of cell types but not necessarily in conjunction with IL-2Rb and gC. Although the IL-15Ra, the IL-2Rb, and the gC chains are believed to associate as a heterotrimeric receptor, whether this is the physiologically relevant form of the IL-15 receptor remains a matter of speculation. For example, the IL-15Ra chain does not co-precipitate with the IL-2Rb/gC in the presence of IL-15.

Moreover, unlike the IL-2Ra chain, the IL-15Ra chain apparently mediates signal transduction. IL-15Ra is a 58-60 kDa protein that shares structural similarities to the IL-2Ra protein. IL-15Ra and IL-2Ra genes also share similar intron-exon organization and are closely linked on human chromosome 10p14-p15. Human IL-15Ra shares about 45% amino acid (aa) homology with the mouse form of the receptor. Eight isoforms of IL-15Ra mRNA have been identified resulting from alternative splicing events involving different exons. The exclusion of exon 2 (ΔExon2) results in an IL-15Ra isoform that does not bind IL-15. Human IL-15Ra-ΔExon3 cDNA encodes a 267 amino acid (aa) protein that contains a 30 aa signal sequence, a 175 aa extracellular region containing one N-linked glycosylation site, a 21 aa transmembrane domain and a 41 aa cytoplasmic tail.

IL-15 signaling can occur through the heterotrimeric complex of IL-15Ra, IL-2Rb and gC; through the heterodimeric complex of IL-2Rb and gC; or through a novel 60-65 kDa IL-15RX subunit found on mast cells. (Anderson, D. M. et al., 1995, *J. Biol. Chem.* 270:29862-29869; Waldemann, T. A. and Y. Tagaya, 1999, *Ann. Rev. Immunol.*, 17:19-49; Dubois, S. et al., 1999, *J. Biol. Chem.* 274:26978-26984). Recently, the binding of IL-15 to IL-15Ra has been reported to antagonize the TNF-alpha-mediated apoptosis in fibroblasts by competing with TNFRI for TRAF2 binding (Bulfone-Paus, S. et al., 1999, *FASEB* 13:1575-1585).

Given the known effects of IL-15 on the immune system, a number of groups have proposed targeting IL-15, to manipulate the immune system for the hosts benefit. While IL-15 administration has been employed to bolster immune responses or augment immune system reconstitution, blockade of IL-15 activity can inhibit autoimmune responses. For example, administration of an IL-15-activity blocking mutant IL-15-Fc protein or a soluble form of the IL-15Ra has therapeutic potential in a mouse model of arthritis and allograft survival.

Conversely, IL-15 (protein or DNA-expression vector) administered as an adjuvant during vaccination or infection augments CD8+ T cell immunity, and IL-15 treatment can enhance protection of mice from lethal doses of *Mycobacterium tuberculosis* and *Escherichia coli*. Furthermore, IL-15 therapy stimulates anti-HIV immunity and increases survival of CD4+ and CD8+ lymphocytes from HIV-infected patients in vitro. IL-15 can also accelerate immune reconstitution after bone marrow transplant. Several groups have found that IL-15 therapy, in conjunction with chemotherapy, Toll-like receptor agonists, or adoptive transfer of tumor reactive CD8+ T cells, can result in increased survival or complete tumor regression in mouse tumor models, in contrast to each therapy alone. Thus, manipulation of IL-15 activity has potential as a therapeutic modality in a number of clinical situations.

IL-15 is currently being used in many studies in which augmentation of the immune response is desirable. These include increasing the efficacy of vaccines against tumors and infections as well as augmenting the ability of the body to remove cancers in the absence of overt vaccination. In addition, IL-15 may aid in regenerating the immune system following bone marrow transplant or in AIDS. However, the half-life of IL-15 in vivo is very short (minutes to 1 hour or so) and this is one reason for poor efficacy. At present the only way to obtain any effect of IL-15 activity is by using large doses, and IL-15 alone is not always effective. Researches have attempted to increase the half-life of IL-15 using molecular modifications but these have generally been ineffective. For example, PEGylation (a common technique to increase protein half-life) of IL-15 increases the half-life but destroys the majority of the activity of the cytokine, in fact, PEG-IL-15 is an antagonist of IL-15 activity.

Therefore, there exists an unmet need to provide a suitable therapeutic form of IL-15 that demonstrates a longer half-life, and a greater efficacy at lower dosages when administered to an organism in need thereof for purposes of modulating or enhancing immunity. Such a therapeutic would allow for the administration of less cytokine while simultaneously providing for the augmentation of the hosts immune system beyond the effects of IL-15 alone.

Our studies showed that the IL-15Ra acts to "transpresent" IL-15 to opposing cells expressing the IL-2/15Rb/gC complex without a requirement for IL-15Ra expression. In addition, in vitro, IL-15 bound to a chimera comprised of the soluble portion of the IL-15Ra covalently linked to an antibody Fc region (IL-15Ra-Fc) (R&D Systems, Inc., Minneapolis, Minn.), supports the survival of IL-15Ra−/− memory CD8 T cells, in contrast to either component alone.

It is generally perceived by those in the pertinent art that the soluble portion of the IL-15Ra is an inhibitor of IL-15 action. In fact, published research has demonstrated that IL-15Ra can inhibit IL-15 activity in vitro and in vivo. Presently, no one has yet devised a system in which IL-15 and IL-15Ra are pre-coupled prior to administration as an in vivo treatment.

SUMMARY OF THE INVENTION

The present invention relates generally to a therapeutic polypeptide composition and methods for its administration to an individual in need thereof. The present invention provides nucleic acids and polypeptides encoded thereby, as well as related compositions including nucleic acid vectors containing the nucleic acids of the invention, cell lines containing the nucleic acids of the invention, and antibodies (e.g., polyclonal, monoclonal, chimeric, etc. . . . ) which bind to the therapeutic polypeptide of the invention. The present invention also relates to methods for generating a therapeutic agent comprising at least one lymphokine or portion thereof, in a pre-coupled complex with at least one lymphokine receptor or portion thereof. It was surprisingly and unexpectedly observed that the pre-coupled combination of the invention demonstrates a longer half-life in vivo, and greater therapeutic efficacy than observed with administration of IL-15 alone.

The invention further encompasses nucleic acid molecules that have at least 25% homology to the nucleotide sequences shown in SEQ ID NOS: 1-4, and 13-16. It will be appreciated by those skilled in the art that DNA sequence polymorphisms that lead to changes in the amino acid sequences of the NOVX polypeptides may exist within a population (e.g., the human population). Such genetic polymorphism in the NOVX genes may exist among individuals within a population due to natural allelic variation. As used herein, the terms "gene" and "recombinant gene" refer to nucleic acid molecules comprising an open reading frame (ORF) encoding an interleukin and/or interleukin receptor polypeptide, preferably from a vertebrate. Such natural allelic variations can typically result in 1-5% variance in the nucleotide sequence. Any and all such nucleotide variations and resulting amino acid polymorphisms in the polypeptides of SEQ ID NOs: 5-12, which are the result of natural allelic variation and that do not alter the functional activity of the polypeptides, are intended to be within the scope of the invention.

In one aspect, the invention relates to nucleic acids and polynucleotide molecules that encode a lymphokine or portions thereof. In addition, the invention relates to nucleic acids and polynucleotide molecules that encode a lymphokine receptor or portions thereof. This aspect of the invention contemplates the use of polynucleotides that encode substantially the full length protein, wild type or mutant polypeptides; discrete segments, domains, subdomains, fragments, deletion or insertion mutations; chimeras; and isoforms and splice variants. This aspect of the invention also includes nucleic acids comprising a segment encoding at least one lymphokine or portion thereof, contiguous with a segment encoding at least one lymphokine receptor or portions thereof within a single open-reading-frame (ORF). In certain embodiments, the nucleic acids of the invention comprise at least one additional polynucleotide segment corresponding to transcription regulator sequences (e.g., promoters, inducible promoters, enhancers, and the like); fusion protein sequences (e.g., His-tag, GST, GFP, antibody Fc portions, antibiotic resistance, signal peptides, and the like); and/or linker sequences disposed at the 5' end, 3' end or at a location within the polypeptide encoding sequences; and/or combinations thereof. In any of the embodiments described herein, the polynucleotides of the invention may also be disposed in a suitable viral vector, bacterial plasmid, or artificial chromosome suitable for cloning and/or expression in a eukaryotic cell or cell extract, prokaryotic cell or cell extract, and/or combinations thereof.

In certain aspects, the present invention relates to a therapeutic composition comprising an interleukin polypeptide, for example IL-2 (SEQ ID NO: 10 and 12), or IL-15 (SEQ ID NO: 5 and 6), including portions and combinations thereof, in a pre-coupled protein complex with an interleukin receptor polypeptide, for example IL-2Ra (SEQ ID NO: 9 and 11), or IL-15Ra (SEQ ID NO: 7 and 8), including portions and combinations thereof. In certain embodiments, the invention relates to a therapeutic polypeptide composition comprising a polypeptide having at least 40% homology to SEQ ID NO.s: 5, 6, 10, 12, portions or combinations thereof, in a pre-coupled complex with a polypeptide having at least 40% homology to SEQ ID NO.s: 7, 8, 9, 11, portions or combinations thereof. In certain other embodiments, the invention relates to a therapeutic polypeptide composition comprising a polypeptide having at least 80% homology to SEQ ID NO.s: 5, 6, 10, 12, portions or combinations thereof, in a pre-coupled complex with a polypeptide having at least 80% homology to SEQ ID NO.s: 7, 8, 9, 11, portions or combinations thereof.

In another aspect, the invention relates to the use of a chimeric polypeptides in the polypeptide complex of the invention. In certain embodiments, the invention comprises chimeric polypeptides comprising one or more interleukins, interleukin receptor, portions and combinations thereof. In other embodiments, the invention comprises chimeric polypeptides comprising at least one interleukin receptor polypeptide or portion thereof, for example, the soluble portion of an interleukin receptor and/or the ligand binding domain, covalently linked and contiguous with the Fc portion of an antibody. The chimeric molecules of the invention may be synthesized recombinantly by expressing a polynucleotide containing the desired elements within a single ORF in any number of combinations, which will be recognized by one of ordinary skill in the art. Other chimeric polypeptides, for example, a human IL-15Ra (1Met-94Ile)-K-(129Pro-205Thr)-linker-Fc polypeptide, are commercially available from R&D Systems (Minneapolis, Minn.).

In another aspect the chimeric polynucleotide molecules are contained in a nucleic acid vector, such as for example a plasmid or viral DNA construct, for subcloning, expression, purification or other routine genetic manipulation suitable for use in a eukaryotic or prokaryotic cell or organism. In addition, the chimeric polynucleotide molecules may optionally contain additional coding or non-coding sequences, inserted by genetic manipulation in between regions coding for lymphokine or lymphokine receptor portions. In one embodiment, the nucleic acid encoding the interleukin or portion thereof, is disposed in tandem linkage with a interleukin receptor portion. In still further embodiments, a linker sequence is inserted between the terminal codon of the first nucleic acid and the first codon of the second nucleic acid. These linkers may be of any length and type suitable, and may be used, for example, to reduce steric constraints on polypeptide folding, introduce a protease or nuclease cleavage site, provide a convenient site for chemical modification, conjugation or other functional element.

In preferred embodiments, the candidate protein is a human protein. In other embodiments, the candidate protein is a eukaryotic protein, for example, a mammalian protein, or a mouse protein. In another aspect, the invention features a transgenic cell or organism that contains a transgene encoding a an interleukin, an interleukin receptor or portion thereof, and/or a chimeric interleukin/interleukin receptor polypeptide. In another aspect, the invention relates to one or more genetically altered cell lines that contain the polynucleotide constructs of the invention, such as, for example, by incorporation into the genomic DNA of the cell, retention episomally or as part of an artificial chromosome. In a related aspect, the present invention relates to the expression by a modified host cell of a nucleic acid encoding individual components or the entire polypeptide complex of the invention. In some embodiments, the transgene encodes a protein that is normally exogenous to the transgenic cell. In some embodiments, the transgene encodes a human protein. In some embodiments, the transgene is linked to a heterologous promoter. In other embodiments, the transgene is linked to its native promoter.

In another aspect, the invention relates to antibodies, for example, polyclonal, monoclonal, or chimeric, that recognize and bind to discrete epitopes of the polypeptide complex of the invention or components thereof. In certain aspects, the invention relates to the administration of antibodies specific to the components of the complex of the invention, the complex of the invention, to other lymphokines, other lymphokine receptors or combinations thereof. In one embodiment, the invention comprises an interleukin, for example IL-2, IL-7, or IL-15, pre-coupled to a antibody specific for said interleukin. In other embodiments, the methods of the invention include method for treating a disease in an individual comprising administering an effective amount of a pre-coupled complex comprising an interleukin and an antibody specific for said interleukin to an individual in need thereof.

In another aspect, the present invention relates to methods for producing an immunomodulatory therapeutic comprising a pre-coupled complex of at least one lymphokine polypeptide or portion thereof, and at least one lymphokine receptor polypeptide or portion thereof. In certain embodiments, the invention includes methods for creating the complex of the invention in vitro comprising expressing or synthesizing of component polypeptides, isolating the polypeptides, purifying and/or concentrating the polypeptides, and forming of the complex. In this aspect, the invention relates to creating the pre-coupled polypeptide complex of the invention from polypeptides isolated from a host cell or cell extract in which each polypeptide component of the complex is expressed from two discrete nucleid acids or as a single open reading from comprising a chimera comprising the interleukin and interleukin receptor linked, in frame, in tandem. The purification can be performed by chromatographic means known to one of ordinary skill in the art and may include, for example, affinity purification, size exclusion, ion exchange, hydroxyapatite, HPLC, and the like.

In another aspect, the invention relates to methods for inducing, enhancing or inhibiting immune cell activity and proliferation comprising administering an effective amount of a pre-coupled polypeptide complex to an individual in need thereof, wherein the pre-coupled polypeptide complex comprises at least one lymphokine or portion thereof and at least one lymphokine receptor or portion thereof. In a related aspect of the invention, the complex may be used to augment a host organism's immunity or immune response to antigen, such as for example, a bacteria, a virus, a protein, a peptide, a nucleic acid, and the like. All of the preceding objects of the invention contemplate the use of IL-15, IL-2, IL-15Ra, or IL-2Ra polypeptides, portions, and combinations thereof. In yet another aspect, the invention includes methods of treating an organism, comprising administering to an organism a vector encoding one or more of SEQ ID NO: 1-4, and 13-16.

In another aspect, the invention relates to a pre-coupled polypeptide complex useful for increasing the proliferation and survival of memory T cells, B cells, and NK cells. As such, administration of the therapeutic of the present invention can also be used to enhance pre-existing immunity (e.g. previously vaccinated individuals) without the need for an actual vaccine booster. In certain aspects the therapeutic of the invention is administered, for example, for the augmentation of vaccination, for enhancing immunity in SCID or AIDS patients, and for the treatment of cancers.

In still other aspects, the pre-coupled polypeptide complex of the invention is useful for inhibiting a host organism's immune response in cases where it is a detriment to the organism. For example, the complex of the invention may be used to inhibit a host organism's immunity or immune response to antigen, for example an auto-antigen, as observed in individuals suffering from autoimmune diseases and conditions like rheumatoid arthritis or Lupus. In certain embodiments of this aspect of the invention the pre-coupled polypeptide complex comprises lymphokine and lymphokine receptor polypeptides or portions thereof; which are unable to activate immune cells or stimulate their proliferation. For example, the polypeptide components of the complex may contain mutations, deletions, insertions or chemical modifications that inhibit signaling via the IL-2 or IL-15 pathways.

In any of the above-described aspects, the pre-coupled polypeptide complex can be administered in any pharmaceutically acceptable form (e.g., liquid, powder, pill, controlled release formula, etc. . . . ), via any suitable route (e.g., intravenous, oral, parenteral, subdermal, topical, anal, nasal, etc. . . . ), and optionally with any pharmaceutically acceptable excipients, carriers, and/or in combination with other active ingredients (e.g., NSAIDS, Immunosuppressants, Anti-histamines, Anti-oncogenics, Antibiotics, Sulfonamides, etc. . . . ). The preceeding are given by way of non-limiting example, and the particular formulation may vary in any number of ways, which are expressly incorporated herein, depending on a multitude of factors which will be recognizable by one of ordinary skill in the art.

In yet another aspect the present invention relates to a kit comprising a suitable container, the pre-coupled polypeptide complex of the invention or the components therefore in a pharmaceutically acceptable form disposed therein, and instructions for its use.

In another aspect, the current invention relates to the production of libraries containing mutated and modified nucleic acids for use in the methods described, and the nucleic acids identified therein.

In another aspect, the invention relates to a method of detecting the presence of a lymphokine-lymphokine receptor polypeptide complex in a sample. In the method, a sample is contacted with a compound or antibody that selectively binds under conditions allowing for formation of a complex between the polypeptide. The complex is detected, if present, thereby identifying the polypeptide complex within the sample. Also included in the invention is a method of detecting the presence of a lymphokine-lymphokine receptor chimeric nucleic acid molecule in a sample by contacting the sample with a lymphokine or lymphokine receptor nucleic acid probe or primer, and detecting whether the nucleic acid probe or primer bound to a lymphokine-lymphokine receptor chimeric nucleic acid molecule the sample.

Additional advantageous features and functionalities associated with the systems, methods and processes of the present invention will be apparent from the detailed description which follows. The publications and other materials used herein to illuminate the background of the invention, and in particular cases, to provide additional details respecting the practice, are incorporated by reference, and for convenience are listed in the appended bibliography.

DESCRIPTION OF THE DRAWINGS

FIG. 11. Liver Cancer Burden Reduced by IL-15+IL-15Ra Protein Complex in Mice. About $1 \times 10^5$ B6-F1 melanoma cells were injected intrasplenically (which directs tumors to the liver). On days 1 and 7 days later mice were treated with PBS (control), 2.5 μg IL-15 or 2.5 μg IL-15+IL-15Ra complex. Fourteen days after inoculation tumors were counted in the liver and the spleens were weighed.

DETAILED DESCRIPTION OF THE INVENTION

In examples of the compositions and methods of preferred embodiments, the useful and advantageous generation of therapeutic polypeptides is presented. In a preferred embodiment, the invention relates to a therapeutic polypeptide complex comprising a lymphokine or portions thereof, and a lymphokine receptor or portions thereof. The term "lymphokine receptor" or "interleukin receptor" refers to the transmembrane receptors for a respective lymphokine or interleukin, and in some embodiments may comprise an antibody capable of binding said lymphokine or interleukin. In this context the antibody functions effectively as the "receptor" for the lymphokine or interleukin polypeptide.

Figure 1:
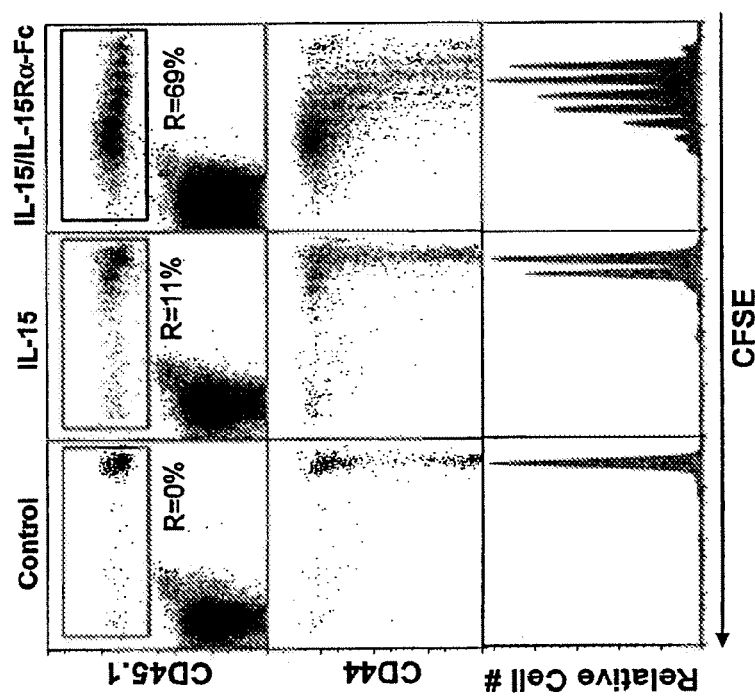
FIG. 1. Co-administration of pre-coupled IL-15+IL-15Ra-Fc enhances CD8+ T cell proliferative response to exogenous IL-15. On day −1 mice received about $1 \times 10^7$ congenic CFSE-labeled, CD8-enriched lymphocytes i.v. and were treated i.p. on day 0 with PBS; IL-15 (about 2.5 μg); or IL-15Ra-Fc (about 15 μg) with IL-15 (2.5 μg). CD8+ splenocytes were analyzed on day 4 by flow cytometry for CFSE fluorescence and CD45.1 expression (top panels); or CD45.1+ CD8+ cells were analyzed for CFSE fluorescence and CD44 expression (middle panels). Bottom panels: On day −1 mice received CFSE-labeled CD8+ T cell enriched splenocytes containing about $6.5 \times 10^5$ tetramer+OVA-specific memory CD8+ T cells and were treated on day 0 with PBS, IL-15 (about 2.5 μg) or IL-15Ra-Fc (about 15 μg) with IL-15 (about 2.5 μg). Donor tetramer+splenocytes were analyzed by flow cytometry on day 4 for CFSE fluorescence. IL-15Ra-Fc treatment alone had no effect on proliferation (data not shown). Data are representative of 3 similar experiments with 3 mice per group.

Without being restricted to any particular theory, the inventors hypothesize that the activity of the therapeutic of the invention results from a process termed, "trans-presentation" in which the receptor portion of the polypeptide complex functions to present the signaling molecule portion to its respective receptor(s) on the target cell's surface. For example, experimental evidence indicates that IL-15Ra trans-presents IL-15 to T cells and other cells in vivo through the beta and gamma chains of the IL-15 receptor. The theory is supported by in vivo results in mice that show IL-15 alone had little activity but the pre-coupled IL-15+IL-15Ra complex had substantial activity on driving memory T cell proliferation (one of the hallmarks of IL-15 activity) as shown in FIG. 1, and reducing tumor burden Table 1. By pre-coupling IL-15 to the IL-15Ra chain the biological activity of IL-15 was greatly augmented in mice (FIGS. 1-8, and 10-12).

Unless clearly indicated to the contrary, the following definitions supplement definitions of terms known in the art.

The term "nucleic acid" refers to deoxyribonucleotides, deoxyribonucleic acids, ribonucleotides, and ribonucleic acids, and polymeric forms thereof, and includes either single- or double-stranded forms. Also, unless expressly limited, the term "nucleic acid" includes known analogues of natural nucleotides, for example, peptide nucleic acids ("PNA"s), that have similar binding properties as the reference nucleic acid. In addition, in any of the preferred embodiments, a particular nucleotide or nucleic acid sequence includes conservative variations (e.g. degenerate codon substitutions; see below), complementary sequences, as well as the sequence explicitly indicated. A degenerate codon substitution is one in which the third position of one or more selected codons is substituted with any nucleotide which results in the same amino acid. The term nucleic acid is generic to the terms "gene," "DNA," "cDNA," "oligonucleotide," "RNA," "mRNA," "nucleotide," "polynucleotide," and the like.

As used herein, the term "oligonucleotide" refers to a series of linked nucleotide residues. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise a nucleic acid sequence having about 10 nt, 50 nt, or 100 nt in length, preferably about 15 nt to 30 nt in length. In one embodiment of the invention, an oligonucleotide comprising a nucleic acid molecule less than 100 nt in length would further comprise at least 6 contiguous nucleotides of SEQ ID NOS: 1-4, or 13-16. Oligonucleotides may be chemically synthesized and may also be used as probes.

A "recombinant" nucleic acid is any nucleic acid produced by an in vitro or artificial (meaning not naturally occurring) process or by recombination of two or more nucleic acids.

The term "gene" is used broadly to refer to any segment of nucleic acid associated with expression of a given RNA or protein. Thus, genes include regions encoding expressed RNAs (which typically include polypeptide coding sequences) and, often, the regulatory sequences required for their expression. Genes can be obtained from a variety of sources, including cloning from a source of interest or synthesizing from known or predicted sequence information, and may include sequences designed to have specifically desired parameters.

In another embodiment, an isolated nucleic acid molecule of the invention comprises a nucleic acid molecule that is a complement of the nucleotide sequence shown in SEQ ID NOs: 1-4, and 13-16. As used herein, the term "complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates. "Fragments" provided herein are defined as sequences of at least 6 (contiguous) nucleic acids or at least 4 (contiguous) amino acids, a length sufficient to allow for specific hybridization in the case of nucleic acids or for specific recognition of an epitope in the case of amino acids, and are at most some portion less than a full length sequence. Fragments may be derived from any contiguous portion of a nucleic acid or amino acid sequence of choice. A full-length clone is identified as containing an ATG translation start codon and an in-frame stop codon. Any disclosed NOVX nucleotide sequence lacking an ATG start codon therefore encodes a truncated C-terminal fragment of the respective polypeptide, and requires that the corresponding full-length cDNA extend in the 5' direction of the disclosed sequence. Any disclosed nucleotide sequence lacking an in-frame stop codon similarly encodes a truncated N-terminal fragment of the respective polypeptide, and requires that the corresponding full-length cDNA extend in the 3' direction of the disclosed sequence.

The term "host cell" includes a cell that might be used to carry a heterologous nucleic acid, or expresses a peptide or protein encoded by a heterologous nucleic acid. A host cell can contain genes that are not found within the native (non-recombinant) form of the cell, genes found in the native form of the cell where the genes are modified and re-introduced into the cell by artificial means, or a nucleic acid endogenous to the cell that has been artificially modified without removing the nucleic acid from the cell. A host cell may be eukaryotic or prokaryotic. For example, bacteria cells may be used to carry or clone nucleic acid sequences or express polypeptides. General growth conditions necessary for the culture of bacteria can be found in texts such as BERGEY'S MANUAL OF SYSTEMATIC BACTERIOLOGY, Vol. 1, N. R. Krieg, ed., Williams and Wilkins, Baltimore/London (1984). A "host cell" can also be one in which the endogenous genes or promoters or both have been modified to produce one or more of the polypeptide components of the complex of the invention.

"Derivatives" are nucleic acid sequences or amino acid sequences formed from the native compounds either directly, by modification, or by partial substitution. "Analogs" are nucleic acid sequences or amino acid sequences that have a structure similar to, but not identical to, the native compound, e.g. they differ from it in respect to certain components or side chains. Analogs may be synthetic or derived from a different evolutionary origin and may have a similar or opposite metabolic activity compared to wild type. Homologs are nucleic acid sequences or amino acid sequences of a particular gene that are derived from different species.

Derivatives and analogs may be full length or other than full length. Derivatives or analogs of the nucleic acids or proteins of the invention include, but are not limited to, molecules comprising regions that are substantially homologous to the nucleic acids or proteins of the invention, in various embodiments, by at least about 30%, 45%, 70%, 80%, or 95% identity (with a preferred identity of 80-95%) over a nucleic acid or amino acid sequence of identical size or when compared to an aligned sequence in which the alignment is done by a computer homology program known in the art, or whose encoding nucleic acid is capable of hybridizing to the complement of a sequence encoding the proteins of the invention under stringent, moderately stringent, or low stringent conditions. See e.g. Ausubel, et al., CURRENT PROTOCOLS IN MOLECULAR BIOLOGY, John Wiley & Sons, New York, N.Y., 1993. Nucleic acid derivatives and modifications include those obtained by gene replacement, site-specific mutation, deletion, insertion, recombination, repair, shuffling, endonuclease digestion, PCR, subcloning, and related techniques.

"Homologs" can be naturally occurring, or created by artificial synthesis of one or more nucleic acids having related sequences, or by modification of one or more nucleic acid to produce related nucleic acids. Nucleic acids are homologous when they are derived, naturally or artificially, from a common ancestor sequence (e.g., orthologs or paralogs). If the homology between two nucleic acids is not expressly described, homology can be inferred by a nucleic acid comparison between two or more sequences. If the sequences demonstrate some degree of sequence similarity, for example, greater than about 30% at the primary amino acid structure level, it is concluded that they share a common ancestor. The degree of similarity will vary and important factors include for example, the degree of overall similarity, the degree of similarity within specific regions of the coding sequence, the similarity of noncoding sequence, and the activity of the polypeptide. For purposes of the present invention, genes are homologous if the nucleic acid sequences are sufficiently similar to allow recombination.

The terms "homology" or "identity," in the context of two or more nucleic acid or polypeptide sequences, refer to two or more sequences or subsequences that are the same or similar, and have a specified percentage of amino acid residues or nucleotides that are the same, when compared and aligned for maximum correspondence, as measured using one of the sequence comparison algorithms such as BLAST, ClustalW, or other algorithms available to persons of skill or by visual inspection. For sequence comparison and homology determination, typically one sequence acts as a reference sequence to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters. Other determinations of homology include hybridization of nucleic acids under stringent conditions.

The phrase "hybridizing," refers to the binding, duplexing, or hybridizing of a molecule only to a particular nucleotide sequence under stringent conditions, including when that sequence is present in a complex mixture (e.g., total cellular) DNA or RNA.

The term "pre-coupled" as used herein, refers to a situation where individual polypeptide components are combined to form the active complex prior to activation or binding at the target site, for example, an immune cell. This includes the situation where the individual polypeptide complex components are synthesized or recombinantly expressed and subsequently isolated and combined to form a complex, in vitro, prior to administration to an organism; the situation where a chimeric or fusion polypeptide (i.e., each discrete protein component of the complex is contained in a single polypeptide chain) is synthesized or recombinantly expressed as an intact complex; and/or the situation where individual polypeptide complex components are administered simultaneously to an individual, for example, intravenously, and form complexes in situ or in vivo.

"Conservative mutations" of a nucleic acid sequence refers to those nucleotides that encode identical or essentially identical amino acid sequences, or where the nucleotide does not encode an amino acid sequence, to essentially identical sequences. This is based on the fact that the genetic code is "degenerate," that is to say a number of distinct nucleic acids encode for the same amino acid. For instance, the codons GTT, GTA, OTC, and GTG all encode the amino acid valine. Thus, at every position where a valine is specified by a codon, the codon can be altered to any of the corresponding codons described without altering the encoded polypeptide. Such nucleic acid variations are "silent mutations," which are one species of "conservative mutation." Unless otherwise described every nucleotide sequence described herein which encodes an amino acid also includes every possible silent variation. One of ordinary skill will recognize that each codon in a nucleic acid (except ATG, which is ordinarily the only codon for methionine) can be modified to yield a functionally identical molecule by standard techniques. Accordingly, in each instance where mutagenesis is used each "silent mutation" of a nucleic acid, which encodes an amino acid, is implicitly included.

Furthermore, one of ordinary skill will recognize that "conservative mutations" also include the substitution, deletion or addition of nucleic acids that alter, add or delete a single amino acid or a small number of amino acids in a coding sequence where the nucleic acid alterations result in the substitution of a chemically similar amino acid. Amino acids that may serve as conservative substitutions for each other include the following: Basic: Arginine (R), Lysine (K), Histidine (H); Acidic: Aspartic acid (D), Glutamic acid (E), Asparagine (N), Glutamine (Q); hydrophilic: Glycine (G), Alanine (A), Valine (V), Leucine (L), Isoleucine (I); Hydrophobic: Phenylalanine (F), Tyrosine (Y), Tryptophan (W); Sulfur-containing: Methionine (M), Cysteine (C). In addition, sequences that differ by conservative variations are generally homologous.

A "subsequence" refers to a sequence of nucleic acids or amino acids that comprise a part of a longer sequence of nucleic acids or amino acids (e.g., polypeptide) respectively.

A nucleic acid "operon" includes a gene that is situated in a functional relationship with other nucleic acid sequences, for example, a promoter, an enhancer, termination signals, or another gene if it increases the transcription of the coding sequence.

"Mutagenesis" as used herein includes such techniques known in the art as PCR mutagenesis, oligonucleotide-directed mutagenesis, site-directed mutagenesis, random mutagenesis, error-prone PCR mutagenesis, etc., and reiterative sequence recombination by any of the techniques described herein.

Descriptions of the molecular biological techniques useful to the practice of the invention including mutagenesis, PCR, cloning, and the like include Berger and Kimmel, GUIDE TO MOLECULAR CLONING TECHNIQUES, METHODS IN ENZYMOLOGY, volume 152, Academic Press, Inc., San Diego, Calif. (Berger); Sambrook et al., MOLECULAR CLONING—A LABORATORY MANUAL (2nd Ed.), Vol. 1-3, Cold Spring Harbor Laboratory, Cold Spring Harbor, N.Y., 1989, and CURRENT PROTOCOLS IN MOLECULAR BIOLOGY, F. M. Ausubel et al., eds., Current Protocols, a joint venture between Greene Publishing Associates, Inc. and John Wiley & Sons, Inc.; Berger, Sambrook, and Ausubel, as well as Mullis et al., U.S. Pat. No. 4,683,202

(1987); PCR PROTOCOLS A GUIDE TO METHODS AND APPLICATIONS (Innis et al. eds), Academic Press, Inc., San Diego, Calif. (1990) (Innis); Arnheim & Levinson (Oct. 1, 1990) C&EN 36-47; Lueng, et al., A method for random mutagenesis of a defined DNA segment using a modified polymerase chain reaction. *Technique: J Methods Cell Molec Biol* 1(1):11-15 (1989), which are incorporated herein by reference in their entirety for all purposes. Exemplary methods of the present invention include performing sequence mutagenesis, recombination, or both, and screening or selection of individual genes.

As used herein, the terms "lymphokine," "interleukin," "IL-15," or "IL-2" is used to refer collectively to all forms of the corresponding polynucleotide or polypeptide sequences including, for example the full length sequence, segments, domains or discrete portions, substitutions, insertion and deletion mutants, chimeras with the same or other lymphokines, isoforms, splice variants, and any combinations thereof.

As used herein, the terms "IL-15Ra," or "IL-2Ra" is used to refer collectively to all forms of the corresponding polynucleotide or polypeptide sequences including, for example the full length sequence, segments, domains or discrete portions, substitutions, insertion and deletion mutants, chimeras with the same or other lymphokine receptors, isoforms, splice variants, and any combinations thereof.

Nucleic Acid Molecules

In some embodiments, the invention comprises nucleic acids and polynucleotide molecules that encode a lymphokine or portions thereof; and nucleic acids and polynucleotide molecules that encode a lymphokine receptor or portions thereof. In any of the nucleic acid embodiments, the invention contemplates the use of polynucleotides that encode substantially the full length protein, wild type or mutant polypeptides; discrete segments, domains, subdomains, fragments, deletion or insertion mutations; chimeras; and isoforms and splice variants. In certain of the preferred embodiments, the invention comprises nucleic acids comprising a polynucleotide segment encoding at least one lymphokine or portion thereof; contiguous with a polynucleotide segment encoding at least one lymphokine receptor or portion thereof within a single open-reading-frame or ORF (i.e., start codon to stop codon). In certain embodiments, the nucleic acids of the invention comprise at least one additional polynucleotide segment comprising a transcription regulatory sequences (e.g., promoters, inducible promoters, enhancers, and the like); fusion protein sequences (e.g., His-tag, GST, GFP, antibody Fc portions, antibiotic resistance, signal peptides, and the like); and/or linker sequences disposed at the 5' end, 3' end or at a location within the polypeptide encoding sequences; and/or combinations thereof. In any of the embodiments described herein, the polynucleotides of the invention may also be disposed in a suitable viral vector, bacterial plasmid, or artificial chromosome suitable for cloning and/or expression in a eukaryotic cell or cell extract, prokaryotic cell or cell extract, and/or combinations thereof.

Many techniques for the cloning, subcloning, and transfer of recombinant nucleic acids into a plasmid vector or a host cell or both, and techniques for library screening and selection, are known in the art, and each of these formats and/or techniques is generally applicable to the present invention. For example, texts that disclose general techniques for manipulating nucleic acids of use in this invention include "Current Protocols in Molecular Biology" (Ausubel et al., eds., 1994)); Sambrook et al., "Molecular Cloning, A Laboratory Manual" (2nd ed. 1989); and Kriegler, "Gene Transfer and Expression: A Laboratory Manual" (1990), the contents and relevant teachings of which are hereby incorporated by reference.

Another aspect of the invention pertains to vectors, preferably expression vectors, containing a nucleic acid encoding SEQ ID NOs: 5-12, or derivatives, fragments or homologs thereof. As used herein, the term "vector" refers to a nucleic acid molecule capable of transporting another nucleic acid to which it has been "operably linked." One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively-linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise a nucleic acid of the invention in a form suitable for expression of the nucleic acid in a host cell, which means that the recombinant expression vectors include one or more regulatory sequences, selected on the basis of the host cells to be used for expression, that is operatively-linked to the nucleic acid sequence to be expressed. Within a recombinant expression vector, "operably-linked" is intended to mean that the nucleotide sequence of interest is linked to the regulatory sequence(s) in a manner that allows for expression of the nucleotide sequence (e.g., in an in vitro transcription/translation system or in a host cell when the vector is introduced into the host cell).

The term "regulatory sequence" is intended to include promoters, enhancers and other expression control elements (e.g., polyadenylation signals). Such regulatory sequences are described, for example, in Goeddel, GENE EXPRESSION TECHNOLOGY: METHODS IN ENZYMOLOGY 185, Academic Press, San Diego, Calif. (1990). Regulatory sequences include those that direct constitutive expression of a nucleotide sequence in many types of host cell and those that direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, etc. The expression vectors of the invention can be introduced into host cells to thereby produce proteins or peptides, including fusion proteins or peptides, encoded by nucleic acids as described herein. The recombinant expression vectors of the invention can be designed for expression of proteins in prokaryotic or eukaryotic cells. For example, proteins can be expressed in bacterial cells such as *Escherichia coli*, insect cells (using baculovirus expression vectors) yeast cells or mammalian cells. Suitable host cells are discussed further in Goeddel, GENE EXPRESSION TECHNOLOGY: METHODS IN ENZYMOLOGY 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *Escherichia coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: (i) to increase expression of recombinant protein; (ii) to increase the solubility of the recombinant protein; and (iii) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith and Johnson, 1988. Gene 67: 31-40), pMAL (New England Biolabs, Beverly, Mass.) and pRITS (Pharmacia, Piscataway, N.J.) that fuse glutathione S-transferase (GST), maltose E binding protein, or protein A, respectively, to the target recombinant protein.

Examples of suitable inducible non-fusion *E. coli* expression vectors include pTrc (Amrann et al., (1988) Gene 69:301-315) and pET lid (Studier et al., GENE EXPRESSION TECHNOLOGY: METHODS IN ENZYMOLOGY 185, Academic Press, San Diego, Calif. (1990) 60-89).

One strategy to maximize recombinant protein expression in *E. coli* is to express the protein in a host bacteria with an impaired capacity to proteolytically cleave the recombinant protein. See, e.g., Gottesman, GENE EXPRESSION TECHNOLOGY: METHODS IN ENZYMOLOGY 185, Academic Press, San Diego, Calif. (1990) 119-128. Another strategy is to alter the nucleic acid sequence of the nucleic acid to be inserted into an expression vector so that the individual codons for each amino acid are those preferentially utilized in *E. coli* (see, e.g., Wada, et al., 1992. Nucl. Acids Res. 20: 2111-2118). Such alteration of nucleic acid sequences of the invention can be carried out by standard DNA synthesis techniques. In another embodiment, the expression vector is a yeast expression vector. Examples of vectors for expression in yeast *Saccharomyces cerivisae* include pYepSec (Baldari, et al., 1987. EMBO J. 6: 229-234), pMFa (Kurjan and Herskowitz, 1982. Cell 30: 933-943), pJRY88 (Schultz et al., 1987. Gene 54; 113-123), pYES2 (Invitrogen Corporation, San Diego, Calif.), and picZ (InVitrogen Corp, San Diego, Calif.). Alternatively, the polypeptides can be expressed in insect cells using baculovirus expression vectors. Baculovirus vectors available for expression of proteins in cultured insect cells (e.g., SF9 cells) include the pAc series (Smith, et al., 1983. Mol. Cell. Biol. 3: 2156-2165) and the pVL series (Lucklow and Summers, 1989. Virology 170: 31-39).

In yet another embodiment, a nucleic acid of the invention is expressed in mammalian cells using a mammalian expression vector. Examples of mammalian expression vectors include pCDM8 (Seed, 1987. Nature 329: 840) and pMT2PC (Kaufmnan, et al., 1987. EMBO J. 6: 187-195). When used in mammalian cells, the expression vector's control functions are often provided by viral regulatory elements. For example, commonly used promoters are derived from polyoma, adenovirus 2, cytomegalovirus, and simian virus 40. For other suitable expression systems for both prokaryotic and eukaryotic cells see, e.g., Chapters 16 and 17 of Sambrook, et al., MOLECULAR CLONING: A LABORATORY MANUAL. 2nd ed., Cold Spring Harbor Laboratory, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert, et al., 1987. Genes Dev. 1: 268-277), lymphoid-specific promoters (Calame and Eaton, 1988. Adv. Immunol. 43: 235-275), in particular promoters of T cell receptors (Winoto and Baltimore, 1989. EMBO J. 8: 729-733) and immunoglobulins (Banerji, et al., 1983. Cell 33: 729-740; Queen and Baltimore, 1983. Cell 33: 741-748), neuron-specific promoters (e.g., the neurofilament promoter; Byrne and Ruddle, 1989. Proc. Natl. Acad. Sci. USA 86: 5473-5477), pancreas-specific promoters (Edlund, et al., 1985. Science 230: 912-916), and mammary gland-specific promoters (e.g., milk whey promoter; U.S. Pat. No. 4,873,316 and European Application Publication No. 264,166). Developmentally-regulated promoters are also encompassed, e.g., the murine hox promoters (Kessel and Gruss, 1990. Science 249: 374-379) and the alpha-fetoprotein promoter (Campes and Tilghman, 1989. Genes Dev. 3: 537-546).

In one embodiment of the present invention, the starting nucleic acid segments are first recombined by any of the formats referenced herein to generate a library of recombinant nucleic acids. The library can vary in size, e.g., ranging from about 10 to about $10^9$ members. In general, the initial nucleic acid segments, and the recombinant libraries of nucleic acids generated include full-length coding sequences (i.e., open reading frame (ORF), which includes the start codon, coding sequence, and stop codon), and any essential regulatory sequences, for example, a promoter and polyadenylation sequence, required for expression. However, in the event that the recombinant nucleic acid does not contain these elements, the recombinant nucleic acids in the library can be inserted into a vector that includes the missing sequences prior to screening and selection of recombinant clones.

The recombinant nucleic acid sequences may be combined in an in vivo format which results in a library of recombinant segments capable of expression. Alternatively, the recombination may be performed in vitro, and the recombinant library is introduced into the desired cell type prior to the step of screening and selection. In some embodiments of the invention, the recombinant nucleic acid library is amplified in a first host, and is then recovered from that host and introduced to a second host for reason of expression, selection, or screening, or any other desirable parameter. The manner by which the recombinant nucleic acid is introduced into the host cell depends on the nucleic acid-uptake characteristics of the cell type (e.g., having viral receptors, being capable of conjugation, being naturally competent, and/or requiring DNA-gun or electropulse). After introduction of the library of recombinant DNA genes, the cells may be propagated to allow expression of genes to occur.

In any of the embodiments, the nucleic acids encoding the lymphokine or lymphokine receptor can be present as: one or more naked DNAs; one or more nucleic acids disposed in an appropriate expression vector and maintained episomally; one or more nucleic acids incorporated into the host cell's genome; a modified version of an endogenous gene encoding the components of the complex; one or more nucleic acids in combination with one or more regulatory nucleic acid sequences; or combinations thereof. In one embodiment, the host cell's endogenous interleukin and/or interleukin receptor genes are modified using homologous recombination techniques such that the cell produces a combination of interleukin polypeptide, a soluble interleukin receptor polypeptide, and interleukin/interleukin receptor complex polypeptides, which can be isolated and purified using standard techniques. In any of the embodiments, a nucleic acid encoding the lymphokine component comprises a member selected from the group consisting of SEQ ID NOs.: 1, 2, 14, 15, portions and combinations thereof. In addition, in any of the embodiments, a nucleic acid encoding the lymphokine receptor component comprises a member selected from the group consisting of SEQ ID NOs.: 3, 4, 13, 16, portions and combinations thereof. The nucleic acid encoding the lymphokine, lymphokine receptor portion, and/or lymphokine/lymphokine receptor chimera may optionally comprise a linker peptide or fusion protein component, for example, His-Tag, FLAG-Tag, GFP, GST, antibody portion, a signal peptide, and the like, at the 5' end, the 3' end, or at any location within the ORF.

In a preferred embodiment, the nucleic acid of the invention comprises a polynucleotide encoding the soluble (i.e., the extracellular) portion of a lymphokine receptor. In a particularly preferred embodiment, the invention comprises a contiguous nucleic acid encoding a signal peptide, a lypmphokine, a linker peptide, and the soluble portion of a lymphokine receptor, and the Fc portion of an antibody. Any of the embodiments described herein, can be achieved using standard molecular biological and genetic approaches well known to those of ordinary skill in the art. In any of the embodiments a cDNA encoding the open reading frame of SEQ ID NOs: 1-4, and 13-16 or portions thereof can be incorporated into commercially available bacterial expression plasmids such as the pGEM (Promega) or pBluescript (Stratagene) vectors, or eukaryotic expression vectors such as the baculovirus system, pCEP, pcDNA vectors or one of their derivatives.

In certain embodiments, the invention comprises an isolated polynucleotide sequence encoding the polypeptide of SEQ ID NOs: 5-12 or portions thereof. By "isolated nucleic acid sequence" is meant a polynucleotide that is not immediately contiguous with either of the coding sequences with which it is immediately contiguous (one on the 5' end and one on the 3' end) in the naturally occurring genome of the organism from which it is derived. The term therefore includes, for example, a recombinant DNA which is incorporated into a vector; into an automatically replicating plasmid or virus; or into the genomic DNA of a prokaryote or eukaryote, or which exists as a separate molecule (e.g., a cDNA) independent of other sequences. The nucleotides can be modified forms of DNA or RNA. Modifications include but are not limited to known substitutions of a naturally-occurring base, sugar or internucleoside (backbone) linkage with a modified base such as 5-methylcytosine, a modified sugar such as 2'-methoxy and 2'-fluoro sugars, and modified backbones such as phosphorothioate and methyl phosphonate.

A polynucleotide can be a DNA molecule, a cDNA molecule, genomic DNA molecule, or an RNA molecule. A polynucleotide as DNA or RNA can include a sequence wherein T (thymidine) can also be U (uracil). The polynucleotide can be complementary to SEQ ID NOs: 1-4, and 13-16, wherein complementary refers to the capacity for precise pairing between two nucleotides. For example, if a nucleotide at a certain position of a polynucleotide is capable of forming a Watson-Crick pairing with a nucleotide at the same position in an anti-parallel DNA or RNA strand, then the polynucleotide and the DNA or RNA molecule are complementary to each other at that position. The polynucleotide and the DNA or RNA molecule are substantially complementary to each other when a sufficient number of corresponding positions in each molecule are occupied by nucleotides that can hybridize with each other in order to effect the desired process. As used herein, hybridization means Watson-Crick hydrogen bonding between complementary nucleoside or nucleotide bases.

In addition, polynucleotides encoding all or a portion of SEQ ID NOs: 1-4, and 13-16 are included. Such polynucleotides include naturally occurring, synthetic and intentionally manipulated DNA molecules. For example, the polynucleotides may be subjected to site-directed mutagenesis by techniques known in the molecular biology art. There are 20 naturally occurring amino acids, most of which are specified by more than one codon. Therefore, degenerate nucleotide sequences are included. The polynucleotides also include polynucleotides coding for polypeptide analogs, fragments or derivatives of antigenic polypeptides which differ from naturally-occurring forms in terms of the identity or location of one or more amino acid residues (deletion analogs containing less than all of the residues specified for the polypeptide, substitution analogs wherein one or more residues specified are replaced by other residues and addition analogs where in one or more amino acid residues is added to a terminal or medial portion of the polypeptide) and which share some or all properties of naturally-occurring forms. These molecules include the incorporation of codons suitable for expression by selected non-mammalian hosts; the provision of sites for cleavage by restriction endonuclease enzymes; and the provision of additional initial, terminal or intermediate DNA sequences that facilitate construction of readily expressed vectors.

The polynucleotides include polynucleotides that encode polypeptides or full-length proteins that contain substitutions, insertions, or deletions into the protein backbone. Related polypeptides are aligned with by assigning degrees of homology to various deletions, substitutions and other modifications. Homology can be determined along the entire polypeptide or polynucleotide or along subsets of contiguous residues. The percent identity is the percentage of amino acids or nucleotides that are identical when the two sequences are compared. The percent similarity is the percentage of amino acids or nucleotides that are chemically similar when the two sequences are compared. Homologous polypeptides are preferably greater than or equal to 25%, preferably greater than or equal to 30%, more preferably greater than or equal to 35% or most preferably greater than or equal to 40% identical.

Plasmids disclosed herein are either commercially available, publicly available on an unrestricted basis, or can be constructed from available plasmids by routine application of well-known, published procedures. Many plasmids and other cloning and expression vectors are well known and readily available, or those of ordinary skill in the art may readily construct any number of other plasmids suitable for use. These vectors may be transformed into a suitable host cell to form a host cell vector system for the production of a polypeptide having the biological activity of a cellular transporter. Suitable hosts include microbes such as bacteria, yeast, insect or mammalian organisms or cell lines. Examples of suitable bacteria are *E. coli* and *B. subtilis*. A preferred yeast vector is pRS426-Gal. Examples of suitable yeast are *Saccharomyces* and *Pichia*. Suitable amphibian cells are *Xenopus* cells. Suitable vectors for insect cell lines include baculovirus vectors. Rat or human cells are preferred mammalian cells.

Transformation of a host cell with recombinant DNA may be carried out by conventional techniques as are well known to those skilled in the art. By "transformation" is meant a permanent or transient genetic change induced in a cell following incorporation of new DNA (i.e., DNA exogenous to the cell). Where the cell is a mammalian cell, a permanent genetic change is generally achieved by introduction of the DNA into the genome of the cell. By "transformed cell" or "host cell" is meant a cell (e.g., prokaryotic or eukaryotic) into which (or into an ancestor of which) has been introduced, by means of recombinant DNA techniques, a DNA molecule encoding a polypeptide of the invention (i.e., an INDY polypeptide), or fragment thereof.

Where the host is prokaryotic, such as *E. coli*, competent cells which are capable of DNA uptake can be prepared from cells harvested after exponential growth phase and subsequently treated by the $CaCl_2$ method by procedures well known in the art. Alternatively, $MgCl_2$ or RbCl can be used. Transformation can also be performed after forming a protoplast of the host cell or by electroporation.

When the host is a eukaryote, such methods of transfection with DNA include calcium phosphate co-precipitates, conventional mechanical procedures such as microinjection, electroporation, insertion of a plasmid encased in liposomes, or virus vectors, as well as others known in the art, may be used. Eukaryotic cells can also be cotransfected with DNA sequences encoding a polypeptide of this disclosure, and a second foreign DNA molecule encoding a selectable phenotype, such as the herpes simplex thymidine kinase gene. Another method is to use a eukaryotic viral vector, such as simian virus 40 (SV40) or bovine papilloma virus, to transiently infect or transform eukaryotic cells and express the protein. (Eukaryotic Viral Vectors, Cold Spring Harbor Laboratory, Gluzman ed., 1982). Preferably, a eukaryotic host is utilized as the host cell as described herein. The eukaryotic cell may be a yeast cell (e.g., *Saccharomyces cerevisiae*) or may be a mammalian cell, including a human cell.

Mammalian cell systems that utilize recombinant viruses or viral elements to direct expression may be engineered. For example, when using adenovirus expression vectors, the nucleic acid sequences encoding a foreign protein may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the polypeptides in infected hosts (e.g., Logan & Shenk, Proc. Natl. Acad. Sci. U.S.A. 81:3655-3659, 1984).

For long-term, high-yield production of recombinant proteins, stable expression is preferred. Rather than using expression vectors that contain viral origins of replication, host cells can be transformed with the cDNA encoding an interleukin/interleukin receptor fusion protein controlled by appropriate expression control elements (e.g., promoter, enhancer, sequences, transcription terminators, polyadenylation sites, etc.), and a selectable marker. The selectable marker in the recombinant plasmid confers resistance to the selection and allows cells to stably integrate the plasmid into their chromosomes and grow to form foci, which in turn can be cloned and expanded into cell lines. For example, following the introduction of foreign DNA, engineered cells may be allowed to grow for 1 to 2 days in an enriched media, and then are switched to a selective media. A number of selection systems may be used, including but not limited to the herpes simplex virus thymidine kinase (Wigler et al., Cell 11: 233, 1977), hypoxanthine-guanine phosphoribosyltransferase (Szybalska & Szybalski, Proc. Natl. Sci. U.S.A. 48: 2026, 1962), and adenine phosphoribosyltransferase (Lowy et al., Cell 22: 817, 1980) genes can be employed.

In other embodiments, the invention pertains to isolated nucleic acid molecules that encode interleukin polypeptides, interleukin receptor polypeptides, antibody polypeptides, and chimeric interleukin/interleukin receptor polypeptides or biologically active portions thereof. Also included in the invention are nucleic acid fragments sufficient for use as hybridization probes to identify chimeric interleukin/interleukin receptor-encoding nucleic acids and fragments for use as PCR primers for the amplification and/or mutation of chimeric interleukin/interleukin receptor nucleic acid molecules. As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule may be single-stranded or double-stranded, but preferably is comprised double-stranded DNA.

In yet another preferred embodiment, the invention includes a method for isolating a nucleic acid of the invention that includes one or more of: (a) recombining nucleic acids from at least two lymphokines or lymphokine receptors to create a library of nucleic acids; (b) transforming the recombinant genes into a competent cell; (c) screening the cells; (d) isolating the desired nucleic acid for further cycles of recombination with another nucleic acid. The method of this invention may also involve the construction of recombinant nucleic acids, plasmid vectors, or both, and the expression of genes in transformed host cells. The molecular cloning techniques required to achieve these goals are well known in the art.

An interleukin encoding nucleic acid can encode a mature interleukin polypeptide. As used herein, a "mature" form of a polypeptide or protein disclosed in the present invention is the product of a naturally occurring polypeptide, precursor form, preproprotein or proprotein. The naturally occurring polypeptide, precursor or proprotein includes, by way of non-limiting example, the full-length gene product encoded by the corresponding gene. Alternatively, it may be defined as the polypeptide, precursor or proprotein encoded by an ORF described herein. The product "mature" form arises, by way of nonlimiting example, as a result of one or more naturally occurring processing steps that may take place within the cell (host cell) in which the gene product arises. Examples of such processing steps leading to a "mature" form of a polypeptide or protein include the cleavage of the N-terminal methionine (Met) residue encoded by the initiation codon of an ORF or the proteolytic cleavage of a signal peptide or leader sequence. Thus a mature form arising from a precursor polypeptide or protein that has residues 1 to n, where residue 1 is the N-terminal methionine, would have residues 2 through n remaining after removal of the N-terminal methionine. Alternatively, a mature form arising from a precursor polypeptide or protein having residues 1 to n, in which an N-terminal signal sequence from residue 1 to residue Met is cleaved, would have the residues from residue Met+1 to residue n remaining. Further as used herein, a "mature" form of a polypeptide or protein may arise from a post-translational modification other than a proteolytic cleavage event. Such additional processes include, by way of non-limiting example, glycosylation, myristoylation, oligomerization or phosphorylation. In general, a mature polypeptide or protein may result from the operation of only one of these processes, or a combination of any of them.

A nucleic acid of the invention can be amplified using cDNA, mRNA or, alternatively, genomic DNA as a template with appropriate oligonucleotide primers according to standard PCR amplification techniques. Furthermore, oligonucleotides corresponding to SEQ ID NOs: 1-4, and 13-16 and portions and combinations thereof can be prepared by standard synthetic techniques, e.g., using an automated DNA synthesizer.

Polypeptides

The present invention is based on the surprising and unexpected discovery that the therapeutic efficacy of interleukins can be enhanced by precoupling or complexing the interleukin to an interleukin receptor or soluble portion thereof. In certain embodiments, the invention includes methods for forming the therapeutic polypeptide complex of the invention. In one embodiment, the method comprises providing a suitable amount of at least one lymphokine polypeptide or portion thereof, providing a suitable amount of at least one lymphokine receptor polypeptide or portion thereof, admixing the lymphokine and lymphokine receptor polypeptides under suitable pH and ionic conditions for a duration sufficient to allow complex formation, and optionally concentrating or purifying the complex. The polypeptides of the complex can be formed, for example, using a peptide synthesizer according to standard methods; by expressing each component polypeptide separately in a cell or cell extract, then isolating and purifying the polypeptide. Optionally, the therapeutic polypeptide complex of the invention can be formed by expressing both polypeptide components of the complex of the invention in the same cell or cell extract, then isolating and purifying the complexes, for example, using chromatographic techniques, such as affinity chromatography with antibodies to the lymphokine portion, the lymphokine receptor portion, or to the complex. In addition, the invention includes the expression of a chimera or fusion protein comprising an interleukin, in-frame and contiguous with an interleukin receptor or portion thereof.

Figure 12:
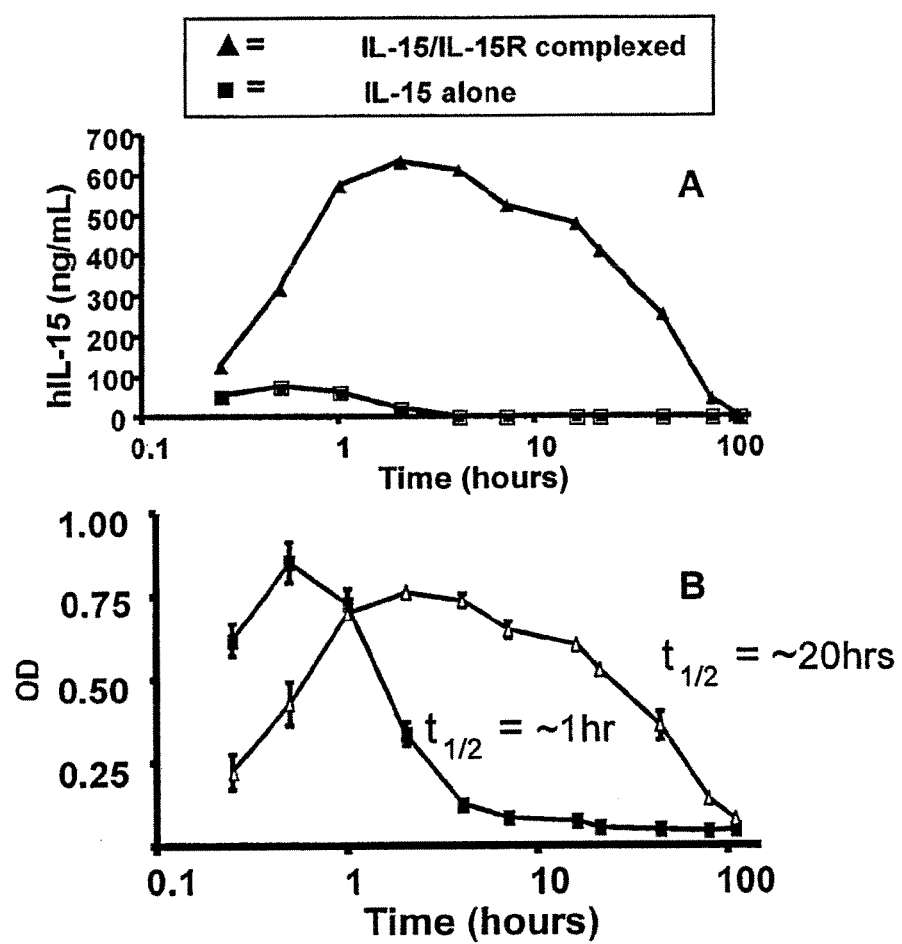
FIG. 12. Complexing IL-15 to IL-15Ra greatly enhances half-life and bioavailability in vivo. (A) 2.5 μg of human IL-15 alone or pre-complexed to IL-15Ra was administered to mice by intraperitoneal injection. At the indicated times, serum was obtained and tested by ELISA for the presence of IL-15. The total IL-15 present was calculated from a standard concentration curve. (B) Half-life was calculated from the linear portion of the decay curve in A.

FIG. 12 demonstrates that the complex of the invention results in a therapeutic composition that exhibits longer half-life in vivo relative to administration of IL-15 alone. Thus, in a preferred embodiment, the therapeutic polypeptide complex of the invention comprises at least one lymphokine polypeptide or portion thereof, pre-coupled or complexed with at least one lymphokine receptor, wherein the complex demonstrates an in vivo half-life and efficacy greater than IL-15 alone. In another embodiment, the complex demonstrates an in vivo half-life of greater than about an hour. In one aspect of this embodiment the therapeutic complex of the invention is formed from recombinant polypeptides expressed in a bacterial or eukaryotic cell or through the use of chemically synthesized peptides. In certain embodiments, the lymphokine polypeptide or portion thereof is a member selected from the group consisting of SEQ ID NOs.: 5, 6, 10, 12, and combinations thereof. In certain embodiments, the lymphokine receptor polypeptide or portion thereof is a member selected from the group consisting of SEQ ID NOs.: 7, 8, 9, 11, and combinations thereof. In another embodiment, the therapeutic complex of the invention demonstrates increased efficacy when administered to an organism in need thereof, compared to the delivery of lymphokine, for example, IL-15 or IL-2, alone.

In another of the preferred embodiments, the invention relates to a method of creating a pre-coupled therapeutic polypeptide complex comprising at least one interleukin, for example, IL-15, IL-2, portions or combinations thereof, pre-coupled or complexed with at least one interleukin receptor, for example, IL-15Ra, IL-2Ra, portions or combinations thereof, generated by incubating the interleukin polypeptide with a soluble interleukin receptor domain or by expressing a novel chimeric nucleic acid molecule comprising the lymphokine polynucleotide segment and the lymphokine receptor polynucleotide segment. In a preferred embodiment, the invention provides a method for pre-coupling a lymphokine and a lymphokine receptor comprising providing a lymphokine portion, and a lymphokine receptor portion, and combining for a suitable amount of time under ionic and pH buffered conditions to allow complex formation. In a particularly preferred embodiment, the lymphokine polypeptide is selected from the group consisting of SEQ ID NOs.: 5, 6, portions or combinations thereof, and the lymphokine receptor polypeptide is selected from the group consisting of SEQ ID NOs.: 7, 8, portions or combinations thereof. In one embodiment, the invention includes a method for forming the complex comprising providing the isolated polypeptide components resuspended in a buffer, for example PBS, admixing the polypeptides, and incubating for from about 1 minute to about 60 minutes at from about 26° C. to about 40° C. In a further embodiment, the lymphokine receptor polypeptide comprises a chimera of a lymphokine binding portion and an antibody Fc portion. In a preferred embodiment, SEQ ID NO.: 6 or portions thereof, and SEQ ID NO.: 8-Fc chimeric molecule are both suspended in PBS, mixed, and incubated for from about 20 minutes to about 40 minutes at from about 35° C. to about 39° C.

In another embodiment, there is provided substantially pure polypeptides homologous to SEQ ID NOs: 5-12. A "substantially pure polypeptide" is an interleukin or interleukin receptor polypeptide, or portion thereof that has been separated from components that naturally accompany it. Typically, the polypeptide is substantially pure when it is at least 60%, by weight, free from the proteins and naturally-occurring organic molecules with which it is naturally associated. Preferably, the preparation is at least 75%, more preferably at least 90%, and most preferably at least 99%, by weight, interleukin and/or interleukin receptor polypeptides. A substantially pure polypeptide may be obtained, for example, by extraction from a natural source (e.g., a eukaryotic cell); by expression of a recombinant nucleic acid encoding a polypeptide; or by chemically synthesizing the protein. Purity can be measured by any appropriate method, e.g., by column chromatography, polyacrylamide gel electrophoresis, or by HPLC analysis.

Amino acids essential for the function of interleukin and interleukin receptor polypeptides can be identified according to procedures known in the art, such as site-directed mutagenesis or alanine-scanning mutagenesis (Cunningham and Wells, Science 244: 1081-1085, 1989; Bass et al., Proc. Natl. Acad. Sci. USA 88: 4498-4502, 1991). In the latter technique, single alanine mutations are introduced at different residues in the molecule, and the resultant mutant molecules are tested for biological activity (e.g., ligand binding and signal transduction) to identify amino acid residues that are critical to the activity of the molecule. Sites of ligand-protein interaction can also be determined by analysis of crystal structure as determined by such techniques as nuclear magnetic resonance, crystallography or photoaffinity labeling. (See, for example, de Vos et al., Science 255: 306-312, 1992; Smith et al., J. Mol. Biol. 224: 899-904, 1992; Wlodaver et al., FEBS Lett. 309: 59-64, 1992). The identities of essential amino acids can also be inferred from analysis of homologies with related proteins.

Multiple amino acid substitutions can be made and tested using known methods of mutagenesis and screening, such as those disclosed by Reidhaar-Olson and Sauer (Science 241: 53-57, 1988; or Bowie and Sauer, Proc. Natl. Acad. Sci. USA 86: 2152-2156, 1989). Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display (e.g., Lowman et al., Biochem. 30: 10832-10837, 1991; Ladner et al., U.S. Pat. No. 5,223,409; Huse, WIPO Publication WO 92/06204) and region-directed mutagenesis (Derbyshire et al., Gene 46: 145, 1986; Ner et al., DNA 7: 127, 1988). Mutagenesis methods as disclosed above can be combined with high-throughput screening methods to detect the activity of cloned, mutagenized proteins in host cells. Mutagenized DNA molecules that encode active proteins or portions thereof (e.g., ligand-binding fragments) can be recovered from the host cells and rapidly sequenced using modern equipment. These methods allow the rapid determination of the importance of individual amino acid residues in a polypeptide of interest, and can be applied to polypeptides of unknown structure.

Using the methods discussed above, one of ordinary skill in the art can prepare a variety of polypeptides that are substantially homologous to SEQ ID NO: 5-12 or allelic variants thereof and retain the properties of the wild-type polypeptides. As expressed and claimed herein the language, "a polypeptide as defined by SEQ ID NO: 5-12" includes all allelic variants and species orthologs of the polypeptides. The term "polypeptide" as used herein includes modified sequences such as glycoproteins, and is specifically intended to cover naturally occurring polypeptides or proteins, as well as those that are recombinantly or synthetically synthesized, which occur in at least two different conformations wherein both conformations have the same or substantially the same amino acid sequence but have different three dimensional structures. "Fragments" are a portion of a naturally occurring protein. Fragments can have the same or substantially the same amino acid sequence as the naturally occurring protein.

The disclosure also encompasses proteins that are functionally equivalent to the interleukin and interleukin receptor gene product, as judged by any of a number of criteria, including but not limited to the resulting biological effect, for example, a change in phenotype such as proliferation of immune cells, changes in gene expression, for example, specific biomarkers which confirm activation of the IL-15 and/or IL-2 signaling pathways. Such functionally equivalent proteins include additions or substitutions of amino acid residues within the amino acid sequence encoded by the nucleotide sequences described, but which result in a silent change or "conservative mutation", thus producing a functionally equivalent gene product. In the case of polypeptide sequences that are less than 100% identical to a reference sequence, the non-identical positions are preferably, but not necessarily, conservative substitutions for the reference sequence. Preferably, conservative amino acid substitutions are made at one or more predicted, non-essential amino acid residues. A "conservative amino acid substitution" is one in which the amino acid residue is replaced with an amino acid residue having a similar side chain. Families of amino acid residues having similar side chains have been defined within the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted non-essential amino acid residue in the protein is replaced with another amino acid residue from the same side chain family. Alternatively, in another embodiment, mutations can be introduced randomly along all or part of the coding sequence, such as by saturation mutagenesis, and the resultant mutants can be screened for biological activity to identify mutants that retain activity. Following mutagenesis, the encoded protein can be expressed by any recombinant technology known in the art and the activity of the protein can be determined.

The polynucleotides can also be designed to provide additional sequences, such as, for example, the addition of coding sequences for added C-terminal or N-terminal amino acids that would facilitate purification by trapping on columns or use of antibodies. Such tags include, for example, histidine-rich tags that allow purification of polypeptides on Nickel columns. Such gene modification techniques and suitable additional sequences are well known in the molecular biology arts.

In another embodiment, the invention relates to a peptide complex comprising a polypeptide having at least 30% homology to a member selected from the group consisting of SEQ ID NOs.: 5, 6, 10, 12, portions and combinations thereof, with a polypeptide having at least 30% homology to a member selected from the group consisting of SEQ ID NOs.: 7, 8, 9, 11, portions and combinations thereof. In another embodiment, the invention relates to a peptide complex comprising a polypeptide having at least 80% homology to a member selected from the group consisting of SEQ ID NOs.: 5, 6, 10, 12, portions and combinations thereof, with a polypeptide having at least 80% homology to a member selected from the group consisting of SEQ ID NOs.: 7, 8, 9, 11, portions and combinations thereof. In another embodiment, the invention comprises a member selected from the group consisting of SEQ ID NOs.: 5, 6, 10, 12, portions and combinations thereof, coupled or complexed with a member selected from the group consisting of SEQ ID NOs.: 7, 8, 9, 11, portions and combinations thereof.

Cellular proliferation, for example, immune cell proliferation, decrease in tumor burden or formation or increase in tumor resistance, are parameters that can be used to evaluate the efficacy of the complex of the invention. It will be understood by one skilled in the art that there are many methods for evaluating the proliferative capacity of cells that are suitable for use in the methods of the invention. For example, cells can be labeled in vitro (or in vivo) with BrdU to determine the percent of dividing cells or evaluated using a colony forming assay, as described in Li et al. (1997), supra. Cell suitable for the analysis of proliferative capacity include cells grown in tissue culture, cells isolated from an animal that has been treated with a test compound, cells that are part of a live animal, or cells that are part of a tissue section obtained from an animal.

In more than one embodiment of the above assay methods of the invention, it may be desirable to immobilize either the interleukin, interleukin receptor, or interleukin/interleukin receptor complex to facilitate separation of complexed from uncomplexed forms the proteins. In one embodiment, a interleukin or interleukin receptor fusion protein can be provided that adds a domain that allows one or both of the proteins to be bound to a matrix. For example, GST-fusion proteins or GST-target fusion proteins can be adsorbed onto glutathione sepharose beads (Sigma Chemical, St. Louis, Mo.) or glutathione derivatized microtiter plates, and the mixture of interleukin and interleukin receptor is incubated under conditions conducive to complex formation (e.g., at physiological conditions for salt and pH). Following incubation, the beads or microtiter plate wells are washed to remove any unbound components, the matrix immobilized in the case of beads, and amount of complex determined either directly or indirectly. Alternatively, the complexes can be dissociated from the matrix, and the amount or activity determined using standard techniques.

Other techniques for immobilizing proteins on matrices can also be used in the invention. For example, either the proteins can be immobilized utilizing conjugation of biotin and streptavidin. Biotinylated protein molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, antibodies reactive with the interleukin or interleukin receptor polypeptides, but which do not interfere with binding, can be derivatized to the wells of the plate, and protein complexes trapped in the wells by antibody conjugation. Methods for detecting such complexes, in addition to those described above for the GST-immobilized complexes, include immunodetection of complexes using antibodies reactive with the interleukin or interleukin receptor polypeptides, as well as enzyme-linked assays that rely on detecting an enzymatic activity associated with the interleukin or interleukin receptor polypeptides.

Another preferred embodiment relates to methods for modulating, inhibiting or augmenting an immune response comprising administering an effective amount of the therapeutic polypeptide complex of the invention to an individual. Other aspects of this method include the administration of an effective amount of the therapeutic polypeptide complex in combination with at least one pharmaceutically acceptable excipient, adjuvant, biologically active agent or a combination thereof.

In another embodiment the invention provides a method for augmenting the immunity of an organism in need thereof by the administration of a pre-coupled complex of a lymphokine and lymphokine receptor that demonstrates a substantially longer in vivo half-life, and substantially greater efficacy than the lymphokine alone. In addition, this embodiment also includes a method of driving homeostatic proliferation of lymphokine responsive immune cells, for example, T cells, B cells, NK cells or the like. In certain of the preferred embodiments, the present embodiment includes the use of a lymphokine receptor molecule which contains a human immunoglobulin Fc fragment. For example, an IL-15Ra-Fc construct is commercially available from R&D Systems (Minneapolis, Minn.). Additionally, it will be recognized by one of ordinary skill in the art that the lymphokine receptor domain of the complex of the invention may optionally have the immunoglobulin Fc fragment removed.

In another embodiment, the present invention includes a method for applying the complex as an adjuvant to increase immune responses to cancer, infection, or to augment vaccination of any kind. In one aspect of this embodiment the complex of the invention is used to enhance immune system reconstitution following bone marrow, stem cell transplantation or in cases of immunodeficiency such as AIDS. The present invention also includes a method of using the complex of the invention to assist in the growth of lymphocytes in vitro which may then be used for adoptive immunotherapy comprising providing a patient; removing a volume of blood from the patient and isolating the patient's lymphocytes; treating the lymphocytes with an effective amount of the complex of the invention; and administering the treated lymphocytes back into the patient.

In still another of the preferred embodiments, the invention includes a method of using the complex modified to be used as an antagonist of lymphokine activity, for example, IL-15. For example, through sequence modifications of a lymphokine or lymphokine receptor, for example, IL-15 or IL-15Ra, the combined complex could be rendered an inhibitor of the lymphokine activity in vivo. Such a molecule could have potential therapeutic effects in inhibiting autoimmunity, transplant rejection or graft-versus host disease.

In any of the preferred embodiments, any of the possible recombinant forms of the lymphokine/lymphokine receptor complex molecule are contemplated. For example, a single chain polypeptide molecule produced from a genetic construct containing the lymphokine gene, for example, IL-2, IL-15, portions or combinations thereof, fused to the lymphokine receptor gene, for example, IL-2Ra, IL-15Ra, portions or combinations thereof, and optionally the Fc portion of an antibody. In certain embodiments the genetic construct can further include one or more nucleic acid sequences that encode a linker polypeptides. In addition to serving to relieve steric or conformational restraints in the complex, it is conceivable that the linker sequence could impart other qualities, for example, a nuclease recognition sequence, a protease recognition sequence, a photo-reactive domain, a hydrophobic domain, hydrophilic domain, an active domain, enzymatic function, a site for chemical modification or conjugation, purification or the like. In further embodiments, the invention provides chimeric molecules comprised of at least one lymphokine gene and at least one lymphokine receptor gene ligated in tandem such that would allow expression of multimeric forms of the complex, for example, dimers, trimers, and the like. These proteins could also be produced in eukaryotic or prokaryotic cells.

Chimeric and Fusion Proteins

As described supra, the invention also provides chimeric or fusion proteins. As used herein, A "chimeric protein" or "fusion protein" comprises a polypeptide operatively-linked to another polypeptide, for example, one or more of the polypeptides chosen from SEQ ID NOs: 5-12, or portions thereof. Whereas the polypeptides chosen from SEQ ID NOs: 5-12 include polypeptides having an amino acid sequence with at least 30% homology. Within the fusion protein the polypeptide can correspond to all or a portion of a polypeptide chosen from SEQ ID NOs: 5-12. In one embodiment, the fusion protein comprises at least one biologically active portion of the protein. In another embodiment, the fusion protein comprises at least two biologically active portions of at least one protein chosen from SEQ ID NOs: 5-12. In yet another embodiment, the fusion protein comprises at least three biologically active portions of at least one protein chosen from SEQ ID NOs: 5-12. Within the fusion protein, the term "operatively-linked" is intended to indicate that the discrete polypeptides are fused in-frame with one another at the N-terminus or C-terminus.

In more than one embodiment of the above assay methods, it may be desirable to immobilize the chimeric polypeptides of the invention to facilitate separation of the proteins. In one embodiment, a fusion protein can be provided which adds a domain that allows the proteins to be bound to a matrix. For example, glutathione-S-transferase fusion proteins or conjugation of biotin and streptavidin.

In one embodiment, the fusion protein is a GST-fusion protein in which the polypeptide sequences are fused to the C-terminus or N-terminus of the GST (glutathione S-transferase) sequences. In another embodiment, the fusion protein contains a heterologous signal sequence at its N-terminus. In certain host cells (e.g., mammalian host cells), expression and/or secretion can be increased through use of a heterologous signal sequence. In yet another embodiment, the fusion protein is immunoglobulin fusion protein in which the polypeptides or polypeptide complex of the invention is fused to sequences derived from a member of the immunoglobulin protein family. In one embodiment, the immunoglobulin fusion proteins of the invention can be incorporated into pharmaceutical compositions and administered to a subject to modulate an interaction between a ligand and a protein on the surface of a cell. The immunoglobulin fusion proteins can be used to affect the bioavailability of a cognate ligand. Inhibition of the ligand interaction may be useful therapeutically for both the treatment of proliferative and differentiative disorders, as well as modulating (e.g. promoting or inhibiting) cell survival. Moreover, the immunoglobulin fusion proteins of the invention can be used as immunogens to produce antibodies in a subject, to purify ligands, and in screening assays to identify molecules that inhibit the interaction.

A chimeric or fusion protein of the invention can be produced by standard recombinant DNA techniques. For example, DNA fragments coding for the different polypeptide sequences are ligated together in-frame in accordance with conventional techniques, e.g., by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers that give rise to complementary overhangs between two consecutive gene fragments that can subsequently be annealed and reamplified to generate a chimeric gene sequence (see, e.g., Ausubel, et al. (eds.) CURRENT PROTOCOLS IN MOLECULAR BIOLOGY, John Wiley & Sons, 1992). Moreover, many expression vectors are commercially available that already encode a fusion moiety (e.g., a GST polypeptide). One or more of SEQ ID NOs: 1-4, and 13-16 can be cloned into such an expression vector such that the fusion moiety is linked in-frame to the desired polypeptide.

Antibodies

The term "antibody" as used herein refers to immunoglobulin molecules and immunologically active portions of immunoglobulin (Ig) molecules, i.e., molecules that contain an antigen-binding site that specifically binds (immunoreacts with) an antigen, comprising at least one, and preferably two, heavy (H) chain variable regions (abbreviated herein as VH), and at least one and preferably two light (L) chain variable regions (abbreviated herein as VL). Such antibodies include, but are not limited to, polyclonal, monoclonal, chimeric, single chain, Fab, Fab' and F(ab')2 fragments, and an Fab expression library. The VH and VL regions can be further subdivided into regions of hypervariability, termed "complementarity determining regions" ("CDR"), interspersed with regions that are more conserved, termed "framework regions" (FR). The extent of the framework region and CDR's has been precisely defined (see, Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917, which are incorporated herein by reference). Each VH and VL is composed of three CDR's and four FRs, arranged from amino-terminus to carboxy-terminus in the following order: FR1, CDR1, FR2, CDR2, FR3, CDR3, FR4. In general, antibody molecules obtained from humans relates to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies can be prepared from the intact polypeptide or fragments containing peptides of interest as the immunizing agent. A preferred antigenic polypeptide fragment is 15-100 contiguous amino acids of SEQ ID NOs: 5-12. In one embodiment, the peptide is located in a non-transmembrane domain of the polypeptide, e.g., in an extracellular or intracellular domain. An exemplary antibody or antibody fragment binds to an epitope that is accessible from the extracellular milieu and that alters the functionality of the protein. In certain embodiments, the present invention comprises antibodies that recognize and are specific for one or more epitopes of any of SEQ ID NOs: 5-12, variants, portions and/or combinations thereof. In other embodiments, the antibodies of the invention may be specific for the interleukin/interleukin receptor complex itself. In still other embodiments an antibody specific for an interleukin may function as the "interleukin receptor"—i.e., functioning in a transpresentation mechanism similar to that observed with a complex involving the soluble portion of the interleukin receptor polypeptides, i.e., IL-15Ra and/or IL-2Ra. In alternative embodiments antibodies of the invention may target and interfere with the interleukin/interleukin receptor interaction to inhibit interleukin signaling.

The preparation of polyclonal antibodies is well known in the molecular biology art; see for example, Production of Polyclonal Antisera in Immunochemical Processes (Manson, ed.), pages 1-5 (Humana Press 1992) and Coligan et al., Production of Polyclonal Antisera in Rabbits, Rats, Mice and Hamsters in Current Protocols in Immunology, section 2.4.1 (1992), The preparation of monoclonal antibodies is also well known in the art; see for example, Harlow et al., Antibodies: A Laboratory Manual, page 726 (Cold Spring Harbor Pub. 1988).

Monoclonal antibodies can be obtained by injecting mice or rabbits with a composition comprising an antigen, verifying the presence of antibody production by removing a serum sample, removing the spleen to obtain B lymphocytes, fusing the lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by techniques well known in the art.

In other embodiments, the antibody can be recombinantly produced, e.g., produced by phage display or by combinatorial methods. Phage display and combinatorial methods can be used to isolate recombinant antibodies that bind to SEQ ID NOs: 5-12 or fragments thereof (as described in, e.g., Ladner et al. U.S. Pat. No. 5,223,409; Kang et al. International Publication No. WO 92/18619; Dower et al. International Publication No. WO 91/17271; Winter et al. International Publication WO 92/20791; Markland et al. International Publication No. WO 92/15679; Breitling et al. International Publication WO 93/01288; McCafferty et al. International Publication No. WO 92/01047; Garrard et al. International Publication No. WO 92/09690; Ladner et al. International Publication No. WO 90/02809; Fuchs et al. (1991) Bio/Technology 9:1370-1372; Hay et al. (1992) Hum Antibod Hybridomas 3:81-85; Huse et al. (1989) Science 246:1275-1281; Griffths et al. (1993) EMBO J. 12:725-734; Hawkins et al. (1992) J Mol Biol 226:889-896; Clackson et al. (1991) Nature 352: 624-628; Gram et al. (1992) PNAS 89:3576-3580; Garrad et al. (1991) Bio/Technology 9:1373-1377; Hoogenboom et al. (1991) Nuc Acid Res 19:4133-4137; and Barbas et al. (1991) PNAS 88:7978-7982).

Human monoclonal antibodies can also be generated using transgenic mice carrying the human immunoglobulin genes rather than the mouse system. Splenocytes from these transgenic mice immunized with the antigen of interest are used to produce hybridomas that secrete human mAbs with specific affinities for epitopes from a human protein (see, e.g., Wood et al. International Application WO 91/00906, Kucherlapati et al. PCT publication WO 91/10741; Lonberg et al. International Application WO 92/03918; Kay et al. International Application 92/03917; Lonberg, N. et al. 1994 Nature 368: 856-859; Green, L. L. et al. 1994 Nature Genet. 7:13-21; Morrison, S. L. et al. 1994 Proc. Natl. Acad. Sci. USA 81:6851-6855; Bruggeman et al. 1993 Year Immunol 7:33-40; Tuaillon et al. 1993 PNAS 90:3720-3724; Bruggeman et al. 1991 Eur J Immunol 21:1323-1326).

A therapeutically useful antibody to the components of the complex of the invention or the complex itself may be derived from a "humanized" monoclonal antibody. Humanized monoclonal antibodies are produced by transferring mouse complementarity determining regions from heavy and light variable chains of the mouse immunoglobulin into a human variable domain, then substituting human residues into the framework regions of the murine counterparts. The use of antibody components derived from humanized monoclonal antibodies obviates potential problems associated with immunogenicity of murine constant regions. Techniques for producing humanized monoclonal antibodies can be found in Jones et al., Nature 321: 522, 1986 and Singer et al., J. Immunol. 150: 2844, 1993. The antibodies can also be derived from human antibody fragments isolated from a combinatorial immunoglobulin library; see, for example, Barbas et al., Methods: A Companion to Methods in Enzymology 2, 119, 1991.

In addition, chimeric antibodies can be obtained by splicing the genes from a mouse antibody molecule with appropriate antigen specificity together with genes from a human antibody molecule of appropriate biological specificity; see, for example, Takeda et al., Nature 314: 544-546, 1985. A chimeric antibody is one in which different portions are derived from different animal species.

Anti-idiotype technology can be used to produce monoclonal antibodies that mimic an epitope. An anti-idiotypic monoclonal antibody made to a first monoclonal antibody will have a binding domain in the hypervariable region that is the "image" of the epitope bound by the first monoclonal antibody. Alternatively, techniques used to produce single chain antibodies can be used to produce single chain antibodies. Single chain antibodies are formed by linking the heavy and light chain fragments of the Fv region via an amino acid bridge, resulting in a single chain polypeptide. Antibody fragments that recognize specific epitopes, e.g., extracellular epitopes, can be generated by techniques well known in the art. Such fragments include Fab fragments produced by proteolytic digestion, and Fab fragments generated by reducing disulfide bridges. When used for immunotherapy, the monoclonal antibodies, fragments thereof, or both may be unlabelled or labeled with a therapeutic agent. These agents can be coupled directly or indirectly to the monoclonal antibody by techniques well known in the art, and include such agents as drugs, radioisotopes, lectins and toxins.

The dosage ranges for the administration of monoclonal antibodies are large enough to produce the desired effect, and will vary with age, condition, weight, sex, age and the extent of the condition to be treated, and can readily be determined by one skilled in the art. Dosages can be about 0.1 mg/kg to about 2000 mg/kg. The monoclonal antibodies can be administered intravenously, intraperitoneally, intramuscularly, and/or subcutaneously.

In certain embodiments of the invention, at least one epitope encompassed by the antigenic peptide is a region of SEQ ID NOs: 5-12 that is located on the surface of the protein, e.g., a hydrophilic region. A hydrophobicity analysis of the protein sequence will indicate which regions of a polypeptide are particularly hydrophilic and, therefore, are likely to encode surface residues useful for targeting antibody production. As a means for targeting antibody production, hydropathy plots showing regions of hydrophilicity and hydrophobicity may be generated by any method well known in the art, including, for example, the Kyte Doolittle or the Hopp Woods methods, either with or without Fourier transformation. See, e.g., Hopp and Woods, 1981, Proc. Nat. Acad. Sci. USA 78: 3824-3828; Kyte and Doolittle 1982, J. Mol. Biol. 157: 105-142, each incorporated herein by reference in their entirety. Antibodies that are specific for one or more domains within an antigenic protein, or derivatives, fragments, analogs or homologs thereof, are also provided herein. A protein of the invention, or a derivative, fragment, analog, homolog or ortholog thereof, may be utilized as an immunogen in the generation of antibodies that immunospecifically bind these protein components.

Human Antibodies

Fully human antibodies essentially relate to antibody molecules in which the entire sequence of both the light chain and the heavy chain, including the CDRs, arise from human genes. Such antibodies are termed "human antibodies", or "fully human antibodies" herein. Human monoclonal antibodies can be prepared by the trioma technique; the human B-cell hybridoma technique (see Kozbor, et al., 1983 Immunol Today 4: 72) and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized in the practice of the present invention and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries (Hoogenboom and Winter, J. Mol. Biol. 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al. (Bio/Technology 10, 779-783 (1992)); Lonberg et al. (Nature 368 856-859 (1994)); Morrison (Nature 368, 812-13 (1994)); Fishwild et al, (Nature Biotechnology 14, 845-51 (1996)); Neuberger (Nature Biotechnology 14, 826 (1996)); and Lonberg and Huszar (Intern. Rev. Immunol. 13 65-93 (1995)).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv molecules.

Fab Fragments and Single Chain Antibodies

According to the invention, techniques can be adapted for the production of single-chain antibodies specific to an antigenic protein of the invention (see e.g., U.S. Pat. No. 4,946,778). In addition, methods can be adapted for the construction of Fab expression libraries (see e.g., Huse, et al., 1989 Science 246: 1275-1281) to allow rapid and effective identification of monoclonal Fab fragments with the desired specificity for a protein or derivatives, fragments, analogs or homologs thereof. Antibody fragments that contain the idiotypes to a protein antigen may be produced by techniques known in the art including, but not limited to: (i) an F(ab')2 fragment produced by pepsin digestion of an antibody molecule; (ii) an Fab fragment generated by reducing the disulfide bridges of an F(ab')2 fragment; (iii) an Fab fragment generated by the treatment of the antibody molecule with papain and a reducing agent and (iv) Fv fragments.

Bispecific Antibodies

Bispecific antibodies are monoclonal, preferably human or humanized, antibodies that have binding specificities for at least two different antigens. In the present case, one of the binding specificities is for an antigenic protein of the invention. The second binding target is any other antigen, and advantageously is a cell-surface protein or receptor or receptor subunit.

Methods for making bispecific antibodies are known in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Because of the random assortment of immunoglobulin heavy and light chains, these hybridomas (quadromas) produce a potential mixture of ten different antibody molecules, of which only one has the correct bispecific structure. The purification of the correct molecule is usually accomplished by affinity chromatography steps. Similar procedures are disclosed in WO 93/08829, published May 13, 1993, and in Traunecker et al., EMBO J., 10:3655-3659 (1991).

Antibody variable domains with the desired binding specificities (antibody-antigen combining sites) can be fused to immunoglobulin constant domain sequences. The fusion preferably is with an immunoglobulin heavy-chain constant domain, comprising at least part of the hinge, CH2, and CH3 regions. It is preferred to have the first heavy-chain constant region (CH1) containing the site necessary for light-chain binding present in at least one of the fusions. DNAs encoding the immunoglobulin heavy-chain fusions and, if desired, the immunoglobulin light chain, are inserted into separate expression vectors, and are co-transfected into a suitable host organism. For further details of generating bispecific antibodies see, for example, Suresh et al., Methods in Enzymology, 121:210 (1986).

According to another approach described in WO 96/27011, the interface between a pair of antibody molecules can be engineered to maximize the percentage of heterodimers which are recovered from recombinant cell culture. The preferred interface comprises at least a part of the CH3 region of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies can be prepared as full length antibodies or antibody fragments (e.g. F(ab')2 bispecific antibodies). Techniques for generating bispecific antibodies from antibody fragments have been described in the literature. For example, bispecific antibodies can be prepared using chemical linkage. Brennan et al., Science 229:81 (1985) describe a procedure wherein intact antibodies are proteolytically cleaved to generate F(ab')2 fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Additionally, Fab' fragments can be directly recovered from E. coli and chemically coupled to form bispecific antibodies. Shalaby et al., J. Exp. Med. 175:217-225 (1992) describe the production of a fully humanized bispecific antibody F(ab')2 molecule. Each Fab' fragment was separately secreted from E. coli and subjected to directed chemical coupling in vitro to form the bispecific antibody. The bispecific antibody thus formed was able to bind to cells overexpressing the ErbB2 receptor and normal human T cells, as well as trigger the lytic activity of human cytotoxic lymphocytes against human breast tumor targets.

Various techniques for making and isolating bispecific antibody fragments directly from recombinant cell culture have also been described. For example, bispecific antibodies have been produced using leucine zippers. Kostelny et al., J. Immunol. 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., Proc. Natl. Acad. Sci. USA 90:6444-6448 (1993) has provided an alternative mechanism for making bispecific antibody fragments. The fragments comprise a heavy-chain variable domain (VH) connected to a light-chain variable domain (VL) by a linker which is too short to allow pairing between the two domains on the same chain. Accordingly, the VH and VL domains of one fragment are forced to pair with the complementary VL and VH domains of another fragment, thereby forming two antigen-binding sites. Another strategy for making bispecific antibody fragments by the use of single-chain Fv (sFv) dimers has also been reported. See, Gruber et al., J. Immunol. 152:5368 (1994). Antibodies with more than two valencies are contemplated. For example, trispecific antibodies can be prepared. Tutt et al., J. Immunol. 147:60 (1991).

Exemplary bispecific antibodies can bind to two different epitopes, at least one of which originates in the protein antigen of the invention. Alternatively, an anti-antigenic arm of an immunoglobulin molecule can be combined with an arm which binds to a triggering molecule on a leukocyte such as a T-cell receptor molecule (e.g. CD2, CD3, CD28, or B7), or Fc receptors for IgG (FcgammaR), such as FcgammaRI (CD64), FcgammaRII (CD32) and FcgammaRIII (CD16) so as to focus cellular defense mechanisms to the cell expressing the particular antigen. Bispecific antibodies can also be used to direct cytotoxic agents to cells which express a particular antigen. These antibodies possess an antigen-binding arm and an arm which binds a cytotoxic agent or a radionuclide chelator, such as EOTUBE, DPTA, DOTA, or TETA.

Heteroconjugate Antibodies

Heteroconjugate antibodies are also within the scope of the present invention. Heteroconjugate antibodies are composed of two covalently joined antibodies. Such antibodies have, for example, been proposed to target immune system cells to unwanted cells (U.S. Pat. No. 4,676,980), and for treatment of HIV infection (WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

Immunoconjugates

The invention also pertains to immunoconjugates comprising an antibody conjugated to a cytotoxic agent such as a chemotherapeutic agent, toxin (e.g., an enzymatically active toxin of bacterial, fungal, plant, or animal origin, or fragments thereof), or a radioactive isotope (i.e., a radioconjugate). Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science, 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026.

In another embodiment, the antibody can be conjugated to a "receptor" for utilization in tumor pretargeting wherein the antibody-receptor conjugate is administered to the patient, followed by removal of unbound conjugate from the circulation using a clearing agent and then administration of a "ligand" that is in turn conjugated to a cytotoxic agent.

Immunoliposomes

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of Chem. 257: 286-288 (1982) via a disulfide-interchange reaction. A chemotherapeutic agent (such as Doxorubicin) is optionally contained within the liposome. See Gabizon et al., J. National Cancer Inst., 81(19): 1484 (1989).

A therapeutically effective amount of an antibody of the invention relates generally to the amount needed to achieve a therapeutic objective. As noted above, this may be a binding interaction between the antibody and its target antigen that, in certain cases, interferes with the functioning of the target, and in other cases, promotes a physiological response. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight.— Common dosing frequencies may range, for example, from twice daily to once a week.

Antibodies specifically binding a protein of the invention, as well as other molecules identified by the screening assays disclosed herein, can be administered for the treatment of various disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Germain, et al., editors) Mack Pub. Co., Easton, Pa.: 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions. The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and gamma-ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid. While polymers such as ethylene-vinyl acetate and lactic acid-glycolic acid enable release of molecules for over 100 days, certain hydrogels release proteins for shorter time periods.

ELISA Assay

An agent for detecting an analyte protein is an antibody capable of binding to an analyte protein, preferably an antibody with a detectable label. Antibodies can be polyclonal, or more preferably, monoclonal. An intact antibody, or a fragment thereof (e.g., Fab or F(ab)2) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Thory of Enzyme Immunoassays", P. Tijssen, Elsevier Science Publishers, Amsterdam, 1985. Furthermore, in vivo techniques for detection of an analyte protein include introducing into a subject a labeled anti-an analyte protein antibody. For example, the antibody can be labeled with a radioactive marker whose presence and location in a subject can be detected by standard imaging techniques intracavity, or transdermally, alone or with effector cells.

Therapeutic Uses and Formulations

The nucleic acids and proteins of the invention are useful in potential prophylactic and therapeutic applications implicated in a variety of disorders including, but not limited to: metabolic disorders, diabetes, obesity, infectious disease, anorexia, cancer, neurodegenerative disorders, Alzheimer's Disease, Parkinson's Disorder, immune disorders, hematopoictic disorders, and the various dyslipidemias, metabolic disturbances associated with obesity, the metabolic syndrome X and wasting disorders associated with chronic diseases and various cancers, cardiomyopathy, atherosclerosis, hypertension, congenital heart defects, aortic stenosis, atrial septal defect (ASD), atrioventricular (A-V) canal defect, ductus arteriosus, pulmonary stenosis, subaortic stenosis, ventricular septal defect (VSD), valve diseases, tuberous sclerosis, scleroderma, lupus erythematosus, obesity, transplantation, adrenoleukodystrophy, congenital adrenal hyperplasia, prostate cancer, neoplasm; adenocarcinoma, lymphoma, uterus cancer, fertility, leukemia, hemophilia, hypercoagulation, idiopathic thrombocytopenic purpura, immunodeficiencies, graft versus host disease, AIDS, bronchial asthma, rheumatoid and osteoarthritis, Crohn's disease; multiple sclerosis, treatment of Albright Hereditary Ostoeodystrophy, and other diseases, disorders and conditions of the like.

Preparations for administration of the therapeutic complex of the invention include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Vehicles include sodium chloride solution, Ringer's dextrose, dextrose and sodium chloride, lactated Ringer's intravenous vehicles including fluid and nutrient replenishers, electrolyte replenishers, and the like. Preservatives and other additives may be added such as, for example, antimicrobial agents, anti-oxidants, chelating agents and inert gases and the like.

The nucleic acid molecules, polypeptides, and antibodies (also referred to herein "active compounds") of the invention, and derivatives, fragments, analogs and homologs thereof, can be incorporated into pharmaceutical compositions suitable for administration. Such compositions typically comprise the nucleic acid molecule, protein, or antibody and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, intraperitoneal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor™. (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., the therapeutic complex of the invention) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For oral administration, the pharmaceutical compositions may take the form for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups, or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring, and sweetening agents as appropriate.

Preparations for oral administration may be suitably formulated to give controlled release of the active compound. For buccal administration the compositions may take the form of tablets or lozenges formulated in conventional manner. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch. The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions, or emulsions in oily or aqueous vehicles, and may contain formulatory agents such as suspending, stabilizing, and/or dispersing agents. Alternatively, the active ingredient may be in powder form for constitution with a suitable vehicle, e.g., sterile pyrogen-free water, before use. The compounds may also be formulated in rectal compositions such as suppositories or retention enemas, e.g., containing conventional suppository bases such as cocoa butter or other glycerides. In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen, et al., 1994. Proc. Natl. Acad. Sci. USA 91: 3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells that produce the gene delivery system. The pharmaceutical compositions can be included in a container, pack, or dispenser together with instructions for administration.

A therapeutically effective dose refers to that amount of the therapeutic complex sufficient to result in amelioration or delay of symptoms. Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects. The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Pharmaceutical compositions may be formulated in conventional manner using one or more physiologically acceptable carriers or excipients. Thus, the compounds and their physiologically acceptable salts and solvates may be formulated for administration by inhalation or insufflation (either through the mouth or the nose) or oral, buccal, intravenous, intraperitoneal, parenteral or rectal administration.

Also disclosed according to the present invention is a kit or system utilizing any one of the methods, selection strategies, materials, or components described herein. Exemplary kits according to the present disclosure will optionally, additionally include instructions for performing methods or assays, packaging materials, one or more containers which contain an assay, a device or system components, or the like.

In an additional aspect, the present invention provides kits embodying the complex and methods of using disclosed herein. Kits of the invention optionally include one or more of the following: (1) polypeptide or nucleic acid components described herein; (2) instructions for practicing the methods described herein, and/or for operating the selection procedure herein; (3) one or more detection assay components; (4) a container for holding nucleic acids or polypeptides, other nucleic acids, transgenic plants, animals, cells, or the like and, (5) packaging materials.

Transgenic Organisms

A transgenic cell or animal used in the methods of the invention can include a transgene that encodes, e.g., a copy of a chimeric polypeptide comprising an interleukin and interleukin receptor. The transgene can encode a protein that is normally exogenous to the transgenic cell or animal, including a human protein. The transgene can be linked to a heterologous or a native promoter.

This disclosure further relates to a method of producing transgenic animals. Techniques known in the art may be used to introduce the transgene into animals to produce the founder line of animals. Such techniques include, but are not limited to: pronuclear microinjection; retrovirus mediated gene transfer into germ lines (Van der Putten et al., Proc. Natl. Acad. Sci. USA 82: 6148-6152, 1985; gene targeting in embryonic stem cells (Thompson et al., Cell 56: 313-321, 1989; electroporation of embryos (Lo, Mol. Cell. Biol. 3: 1803-1814, 1983; and sperm-mediated gene transfer (Lavitrano, et al., Cell 57: 717-723, 1989; etc. For a review of such techniques, see Gordon, Intl. Rev. Cytol. 115: 171-229, 1989. Accordingly, the invention features a transgenic organism that contains a transgene encoding a chimeric interleukin/interleukin receptor polypeptide. The transgenic organism can be a eukaryotic cell, for example, a yeast cell, an insect, e.g., a worm or a fly, a fish, a reptile, a bird, or a mammal, e.g., a rodent. The transgenic organism can further comprise a genetic alteration, e.g., a point mutation, insertion, or deficiency, in an endogenous gene.

A host cell of the invention, such as a prokaryotic or eukaryotic host cell in culture, can be used to produce (i.e., express) the polypeptide components or complex of the invention. Accordingly, the invention further provides methods for producing protein using the host cells of the invention. In one embodiment, the method comprises culturing the host cell of invention (into which a recombinant expression vector encoding the protein has been introduced) in a suitable medium such that the protein is produced. In another embodiment, the method further comprises isolating the protein from the medium or the host cell.

Another aspect of the invention pertains to host cells into which a recombinant expression vector of the invention has been introduced. The terms "host cell" and "recombinant host cell" are used interchangeably herein. It is understood that such terms refer not only to the particular subject cell but also to the progeny or potential progeny of such a cell. Because certain modifications may occur in succeeding generations due to either mutation or environmental influences, such progeny may not, in fact, be identical to the parent cell, but are still included within the scope of the term as used herein. A host cell can be any prokaryotic or eukaryotic cell. For example, protein can be expressed in bacterial cells such as E. coli, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (MOLECULAR CLONING: A LABORATORY MANUAL. 2nd ed., Cold Spring Harbor Laboratory, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Various selectable markers include those that confer resistance to drugs, such as G418, hygromycin and methotrexate. Nucleic acid encoding a selectable marker can be introduced into a host cell on the same vector as that encoding the protein or can be introduced on a separate vector. Cells stably transfected with the introduced nucleic acid can be identified by drug selection (e.g., cells that have incorporated the selectable marker gene will survive, while the other cells die).

The host cells of the invention can also be used to produce non-human transgenic animals. For example, in one embodiment, a host cell of the invention is a fertilized oocyte or an embryonic stem cell into which the protein-coding sequences have been introduced. Such host cells can then be used to create non-human transgenic animals in which exogenous polypeptide sequences have been introduced into their genome or homologous recombinant animals in which endogenous polypeptide sequences have been altered. Such animals are useful for studying the function and/or activity of proteins and for identifying and/or evaluating modulators of protein activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, etc. A transgene is exogenous DNA that is integrated into the genome of a cell from which a transgenic animal develops and that remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous gene has been altered by homologous recombination between the endogenous gene and an exogenous DNA molecule introduced into a cell of the animal, e.g., an embryonic cell of the animal, prior to development of the animal.

An example of a preferred embodiment of the invention is provided below. As will be understood by one of ordinary skill in the art, the techniques described and hereby incorporated into the present invention are generally applicable and may be varied in any number of ways without departing from the general scope of the invention. The following example is given by way of example of the preferred embodiments, and is in no way considered to be limiting to the invention. For example, the relative quantities of the ingredients may be varied to achieve different desired effects, additional ingredients may be added, and/or similar ingredients may be substituted for one or more of the ingredients described.

Example 1

Co-Administration of IL-15 and IL-15Ra Drives CD8 Memory T Cell and NK Cell Proliferation In Vivo In order to determine whether co-administration of IL-15 and recombinant mouse IL-15Ra-Fc (rmIL-15Ra-Fc) could mediate IL-15 activity in vivo, we utilized an adoptive transfer model to gage the effect of IL-15 on the proliferation of CD8+ T cells. CD45.1 CFSE labeled enriched splenic CD8+ T cells were transferred to normal CD45.2 mice and rmIL-15Ra-Fc (about 15 µg). Four days after treatment with IL-15 alone, about 11% of the donor CD8+ T cell population had divided (FIG. 1a, top panels), in agreement with our previous results. In dramatic contrast, the coadministration of the same amount of IL-15 bound to rmIL-15Ra-Fc resulted in the proliferation of about 69% of the donor CD8+ T cells (FIG. 1). Furthermore, while the majority of CD8 T cells responding to IL-15 alone divided once, the cells responding to combination treatment underwent 5-7 divisions, resulting in a substantial increase in cell numbers (data not shown). The bulk of the dividing cells expressed high levels of CD44, suggesting that the responding cells were primarily memory CD8+ T cells or that CD44 had been upregulated (FIG. 1a, bottom panels). Importantly, administration of rmIL-15Ra-Fc alone did not induce proliferation of CD8+ T cells (data not shown). Of note, co-administration of a soluble form of rmIL-15Ra with IL-15 also resulted in enhanced proliferation of donor CD8+ T cells albeit to a level intermediate to IL-15 alone and IL-15 combined with rmIL-15Ra-Fc (data not shown). In order to test the action of combined therapy on bona-fide memory CD8 T cells, we adoptively transferred CFSE-labeled ovalbumin (OVA)-specific CD8+ memory T cells that had been generated by infection with recombinant vesicular stomatitis virus expressing OVA (VSV-OVA). Similar to the above results, antigen-specific memory CD8+ T cells responding to combined IL-15/IL-15Ra-Fc treatment proliferated to a much greater extent than those provided IL-15 alone (FIG. 1b).

Figure 2:
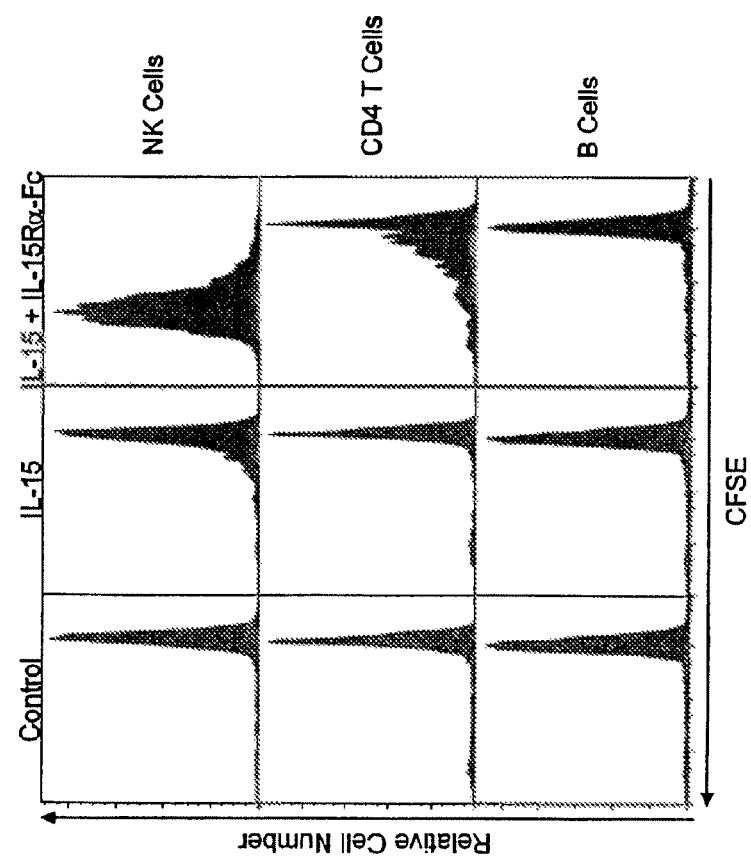
FIG. 2. NK cells are highly responsive to pre-coupled IL-15+IL-15Ra-Fc. On day −1, mice received about $1.5 \times 10^7$ congenic CFSE-labeled lymphocytes i.v. and on day 0 were treated with PBS, IL-15 (about 2.5 μg), or IL-15 (about 2.5 μg)+IL-15Ra-Fc (about 15 μg) i.p. Spleen cells were analyzed by flow cytometry on day 4. Samples were gated on the indicated in the donor population. Data is representative of 2 experiments with 3 mice per group.

Past studies have implicated IL-15 as an inducer of B cell, NK cell and NK T cell proliferation, but not of CD4+ T cell proliferation. Therefore, we examined the ability of IL-15 and receptor-complexed IL-15 to induce proliferation of these cell types using the adoptive transfer system. CD4+ T cells and B cells did not proliferate in response to about 2.5 µg of IL-15, while NK cells proliferated very little (FIG. 2). In contrast, coadministration of rmIL-15Ra-Fc with IL-15 induced extensive proliferation of NK cells while B cells did not respond. The response of NK-T cells was similar to that of NK cells (data not shown). Interestingly, although IL-15 is not thought to mediate proliferation of mouse CD4+ T cells, CD4+ T cells illustrated an intermediate response to the administered complex.

Example 2

Complexed IL-15/IL-15Ra Greatly Enhances IL-15 Activity In Vivo

Figure 3:
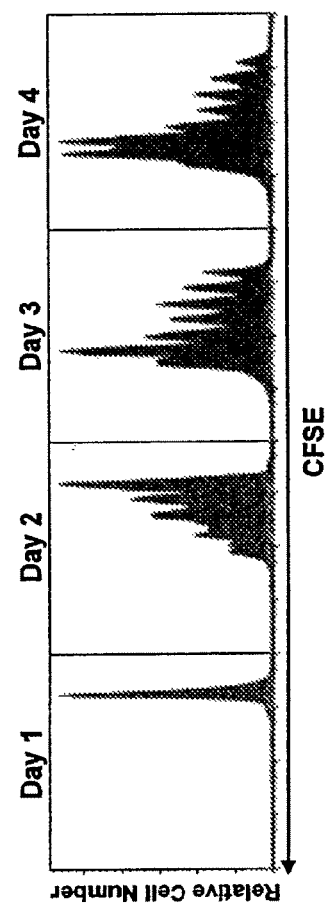
FIG. 3. CD8+ T cells rapidly divide in response to pre-coupled IL-15+IL-15Ra-Fc treatment. On day −1 mice received about $1 \times 10^7$ congenic CFSE-labeled, CD8 enriched lymphocytes i.v. and were treated with PBS or IL-15 (about 2.5 μg)+IL-15Ra-Fc (about 15 μg) on day 0. Peripheral blood lymphocytes were analyzed by flow cytometry on days 1-4. Samples shown are gated on live donor CD8 T cells. Data are representative of 2 experiments with at least 3 mice per group. PBS treatment had no effect on cell division (data not shown).
Figure 4:
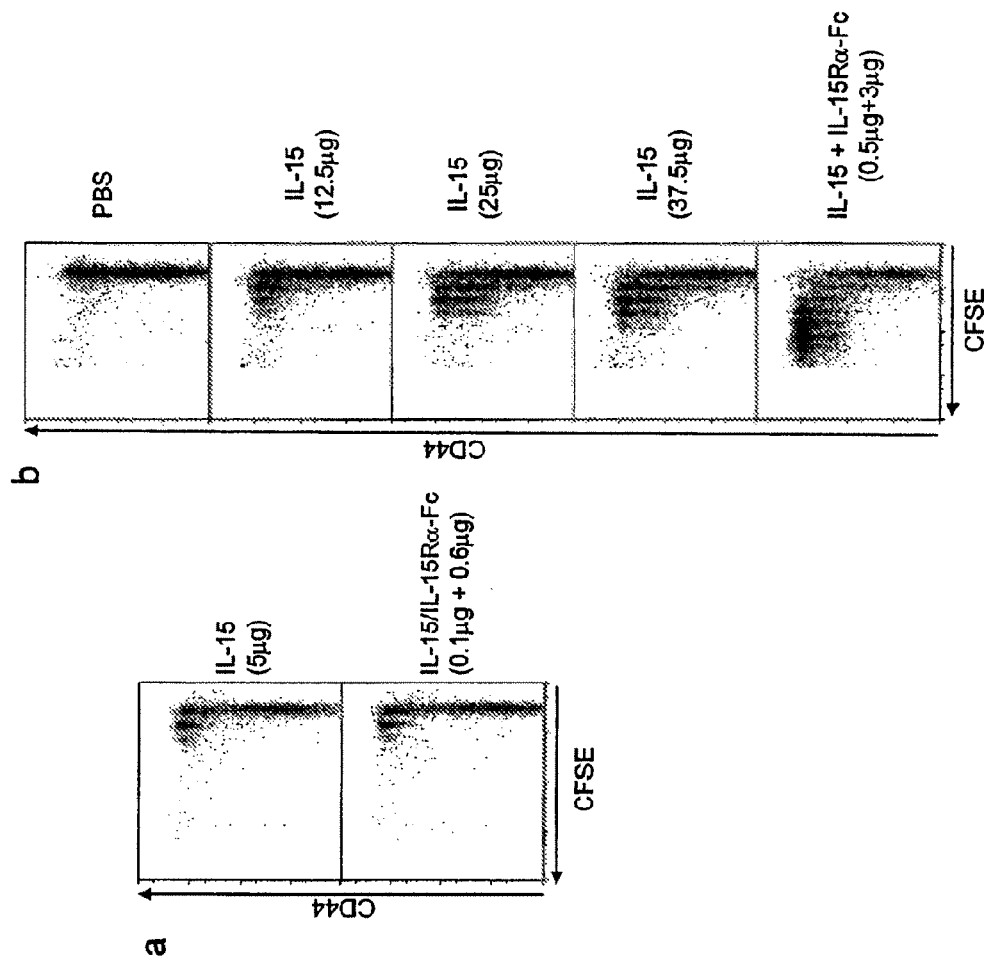
FIG. 4. Coadministration of IL-15Ra-Fc with IL-15 greatly enhances IL-15 potency. (a) On day −1 mice received about $1.5 \times 10^6$ congenic CFSE-labeled, CD8 enriched lymphocytes i.v. and on day 0 received either PBS (not shown), IL-15 (about 5 μg) or varying doses of IL-15 with IL-15Ra-Fc (about 2.5 μg+15 μg, about 0.5 μg+3 μg, about 0.1 μg+0.6 μg, or about 0.02 μg+0.12 μg) i.p. (b) On day −1 each mouse received about $4.5 \times 10^6$ congenic CFSE-labeled, CD8 enriched lymphocytes i.v. and on day 0 received either PBS (not shown), IL-15 (about 0.5 μg)+IL-15Ra-Fc (about 3 μg), or varying doses of IL-15 (about 12.5 μg, 25 μg, or 37.5 μg) i.p. CD8+ splenocytes were analyzed on day 4 for CFSE dilution by flow cytometry.

We next examined the early kinetics of the proliferative response to the coadministration of rmIL-15Ra-Fc with IL-15. CFSE dilution was negligible one day after treatment, but by day two about 36% of the donor CD8+ T cell population had divided, with an appreciable number of cells in the third and fourth rounds of division (FIG. 3). By day three about 59% of donor CD8+ T cells had divided with many cells in divisions 5-6, while about 73% had divided by day four with some cells in the seventh round of division. These results and others showed that the maximum effect of a single dose of IL-15/mL-15Ra-Fc was achieved by approximately 4 days post-treatment, followed by the donor CD8+ T cells entering a protracted rate of proliferation characteristic of memory CD8+ T cells (data not shown).

In order to obtain an approximation of the enhancement of activity obtained by combined treatment over that of IL-15 alone we performed titrations of IL-15 and IL-15/rmIL-15Ra-Fc using the adoptive transfer model. Comparisons were based on the extent of donor CD8+ T cell proliferation as assessed by CFSE dilution. A dose of about 0.1 µg of IL-15 combined with about 0.6 µg of IL-15Ra-Fc induced a level of proliferation similar to that of about 5 µg of IL-15 (FIG. 4a). Thus, in this type of experiment, IL-15 activity was enhanced ~50-fold by coadministration with rmIL-15Ra-Fc. Considering this substantial enhancement, we questioned whether IL-15 alone could achieve this level of activity. Even with the administration of about 37.5 µg of IL-15, the level of proliferation obtained with about 0.5 µg of receptor complexed IL-15 could not be achieved (FIG. 4b). These results suggested that IL-15Ra availability may be limiting in vivo since increasing IL-15 levels did not result in further augmentation of activity.

Example 3

Complexed IL-15/IL-15Ra Operates Via Transpresentation Requiring IL-15Rb

The effects of complexed IL-15/IL-15Ra could either be mediated by direct or indirect effects on the responding cell types. If direct, then it might be expected that the target cells would be required to express IL-15R component(s). To test this, we transferred CFSE-labeled IL-15Ra-/- CD8+ T cells into IL-15Ra-/- hosts and treated the mice with either IL-15 or complexed IL-15/IL-15Ra. IL-15 could not be transpresented in the absence of IL-15Ra, and did not induce proliferation (FIG. 5a). On the other hand, donor CD8+ T cells from IL-15/mL-15Ra-Fc treated mice proliferated extensively. Furthermore, the IL-15Ra-/- donor cells, which primarily consisted of naïve phenotype CD8+ T cells, progressively increased their expression of CD44 and CD122 with division. Since responding T cells did not require IL-15Ra to respond to complexed IL-15/IL-15Ra, we examined the role of IL-15Rb (CD122) in mediating this effect. To this end, we transferred CFSE-labeled CD122+/+ or CD122-/- CD8+ T cells into normal mice and analyzed the donor cells for CFSE dilution 4 days after treatment. While control cells proliferated vigorously in response to IL-15/rmIL-15Ra-Fc treatment, CD122-/- donor CD8+ T cells did not proliferate in response to coadministration (FIG. 5b). Taken together, the results indicated that IL-15/IL-15Ra-Fc operated via direct transpresentation through interaction with the IL-15Rb likely in conjunction with gammaC.

Example 4

Proliferation Induced by Forced IL-15 Transpresentation Requires MHC Class I but not IL-7 or Dendritic Cells While naïve T cells require MHC class I and endogenous peptide for their survival, memory CD8 T cell survival and proliferation is thought to be MHC class I-independent. Homeostatic proliferation of these subsets in empty hosts exhibits similar MHC requirements. Given these results, it was important to determine the MHC requirement for proliferation induced by co-administration of rmIL-15Ra-Fc with IL-15. Thus, we cotransferred naïve TCR transgenic CD8+ T cells (OT-I) and enriched B6 CD8+ T cells (which contain memory cells) to normal or MHC class I deficient (b2-microglobulin-/-) mice. Interestingly, naïve OT-IRAG-/- CD8 T cells proliferated robustly in response to treatment with the complex in a MHC class I sufficient host. In contrast, in MHC class I-/- hosts, naïve T cell proliferation did not occur (FIG. 6a). Similarly, B6 CD8 T cells proliferated in normal hosts but surprisingly proliferation was virtually absent in MHC class I-/- hosts. These data indicated that induction of proliferation by IL-15/IL-15Ra was MHC class I dependent for both naïve and memory CD8+ T cells. Since the proliferative response induced by the coadministration of rmIL-15Ra-Fc with IL-15 was dependent on host expression of MHC class I we wished to investigate other criteria that might also play a role. We examined the involvement of IL-7, since this cytokine is essential for homeostatic proliferation of CD8 T cells in immunodeficient hosts. CFSE-labeled CD8+ T cells were transferred to control or IL-7-/- mice and combined IL-15/mL-15Ra-Fc was administered. In the presence or absence of IL-7 CD8+ T cells proliferated equally well in response to IL-15 with IL-15Ra-Fc (FIG. 6b), indicating that IL-7 was not involved in IL-15 mediated proliferation in our system. Previous studies have highlighted the potential of dendritic cells (DC) in mediating IL-15 activity and MHC expression by DC can be important in T cell homeostasis. To test what role DC play in the proliferative response induced by IL-15/IL-15Ra coadministration we utilized a system in which DC can be conditionally depleted. CD11c-DTR mice express the simian diptheria toxin receptor under the control of the CD11c promoter, making CD11c+ cells susceptible to DT, which removes >95% of DC. Due to the toxicity of DT to intact CD11c-DTR mice as a result of effects on non-hematopoietic cells, we generated chimeras using CD11c-DTR bone marrow and normal B6 hosts. CFSE-labeled CD8+ T cells were then transferred to the chimeras which were treated with DT prior to administration of the IL-15/IL-15Ra complex. Interestingly, we found no difference in CD8+ T cell proliferation between DT treated control or CD11c-DTR chimeras (FIG.

6c). Thus, although MHC class I was essential for IL-15 mediated proliferation, DC were not required.

Example 5

Figure 5:
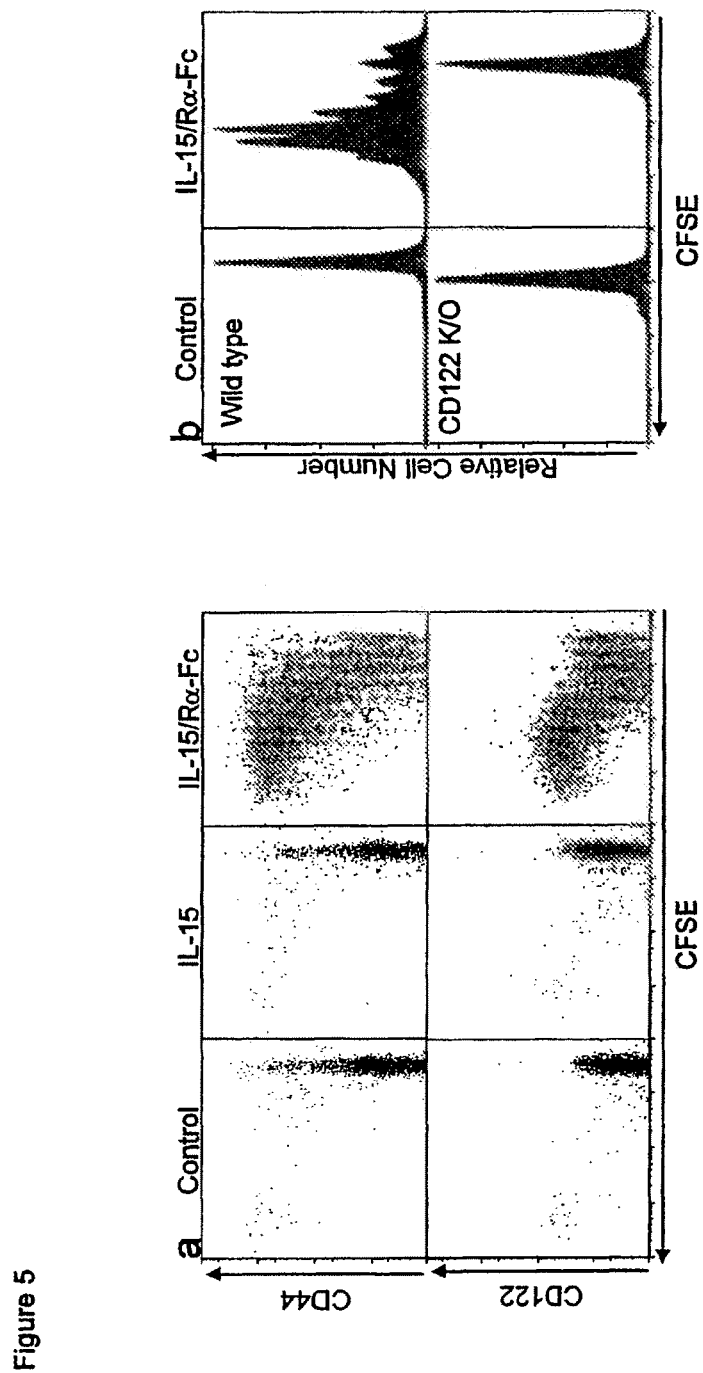
FIG. 5. Activity of complexed IL-15+IL-15Ra-Fc requires IL-2Ra but not IL-15Ra expression by responding cells. (a) On day −1 IL-15Ra−/− mice received congenic CFSE-labeled, CD8 enriched IL-15Ra−/− lymphocytes i.v. and on day 0 were treated with PBS, IL-15 (about 2.5 μg) or IL-15 (about 2.5 μg)+IL-15Ra-Fc (about 15 μg) i.p. On day 4 CD8+ donor splenocytes were analyzed for CFSE fluorescence and CD44 and CD122 expression. (b) On day −1 normal mice received congenic CFSE-labeled wild type or IL-2/IL-15Ra −/− splenocytes i.v. and on day 0 were treated with either PBS or IL-15 (about 2.5 μg)+IL-15Ra-Fc (about 15 μg) i.p. CD8+ donor splenocytes were analyzed for CFSE dilution on day 4 by flow cytometry.
Figure 6:
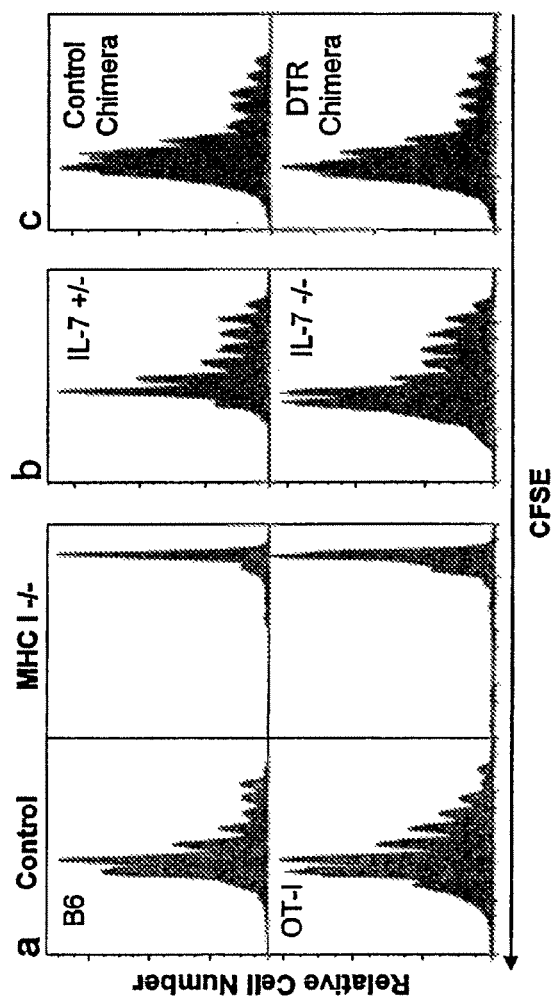
FIG. 6. Pre-coupled IL-15+IL-15Ra-Fc driven proliferation of CD8+ T cells requires MHC class I expression, but does not require IL-7 or DC. (a) On day −1 B6 and beta2m−/− mice received a mixture of normal B6 and naïve OT-I-RAG−/− CFSE-labeled CD8+ T cells and on day 0 were treated with either PBS or IL-15 (about 2.5 μg)+IL-15Ra-Fc (about 15 μg). (b) On day −1 IL-7+/− or IL-7−/− mice received congenic CFSE-labeled CD8-enriched lymphocytes. On day 0, mice received IL-15 (about 2.5 μg)+IL-15Ra-Fc (about 15 μg) i.p. (c) On day −1 chimeras produced with B6 or CD11c-DTR bone marrow received splenocytes i.v and on day 0 were treated with either PBS or IL-15Ra-Fc (about 15 μg)+IL-15 (about 2.5 μg) i.p. All mice were treated with DT on days 0, 1, and 3. In all cases donor CD8+ splenocytes were analyzed for CFSE dilution on day 4.
Figure 7:
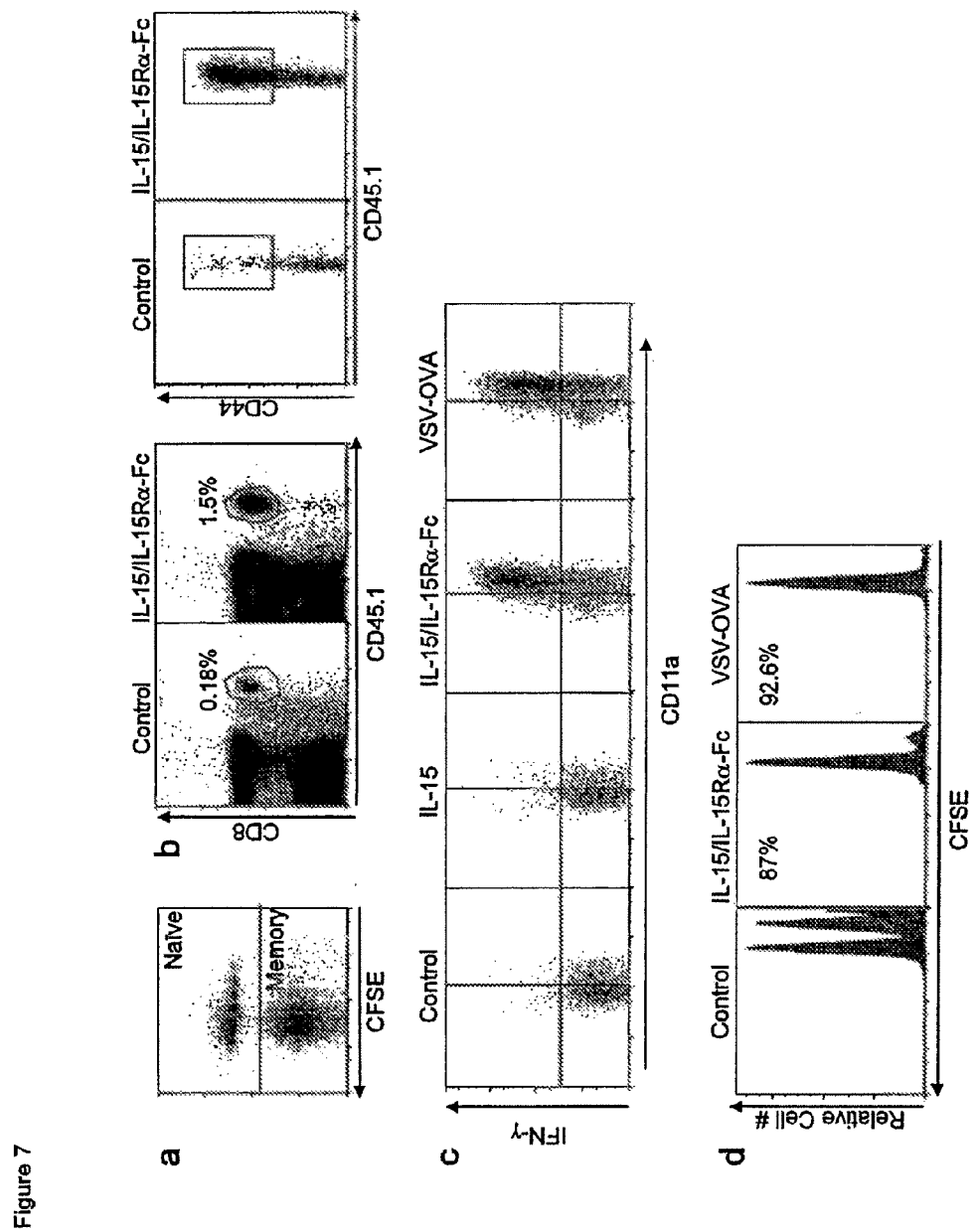
FIG. 7. Naïve CD8+ T cells acquire effector phenotype and function in response to pre-coupled IL-15+IL-15Ra-Fc treatment. On day −1 mice received a mixture of naïve and memory OT-I-RAG−/− cells (a) or only naïve OT-I-RAG−/− cells (b-d), and were treated with either PBS or rmIL-15Ra-Fc (about 15 μg) with IL-15 (about 2.5 μg) on day 0. Four days later splenocytes were examined for (a) CFSE intensity, (b) percentage of donor OT-I and CD44 expression. (c) On day −1 mice received about $7 \times 10^5$ naïve OT-I-RAG−/− cells and on day 0 were treated with PBS, IL-15 (about 2.5 μg), IL-15 (about 2.5 μg)+IL-15Ra-Fc (about 15 μg), or about $1 \times 10^5$ pfu VSV-OVA. On day 4 splenocytes were incubated in vitro with or without SIINFEKL peptide for about 5 hours and the production of IFN-a was analyzed by intracellular staining. (d) On day −1 mice received about $2 \times 10^5$ naïve OT-I-RAG−/− cells and were treated with PBS or IL-15 (about 2.5 μg)+IL-15Ra-Fc (about 15 μg) i.p or about $1 \times 10^5$ pfu of VSV-OVA i.v. On day 4 posttreatment each mouse received a mixture of CFSE-labeled (about 0.25 μM) non-peptide pulsed splenocytes and CFSE-labeled (about 2.5 μM) SIINFEKL peptide pulsed splenocytes. Four hours later splenocytes were analyzed for the presence of the CFSE-labeled target populations.

IL-15/IL-15Ra Immunotherapy Induces Naïve T Cell Activation and Effector Function In previous experiments we noted that CD44low polyclonal CD8 T cells as well as naïve TCR transgenic T cells responded to IL-15 when co-administered with IL-15Ra-Fc (FIGS. 5 and 6). Considering that under homeostatic conditions, CD8 memory T cells exhibit much greater responsiveness to IL-15 than do naïve CD8+ T cells, we wished to directly compare the responsiveness of these two subsets to complexed IL-15/rmIL-15Ra-Fc. To do so, CFSE-labeled memory OT-I and naïve OT-I CD8+ T cells were adoptively transferred into the same congenic C57BL/6 hosts and proliferation was analyzed 4 days after treatment with IL-15/IL-15Ra-Fc. Surprisingly, naïve OT-I CD8 T cells proliferated almost as well as memory UT-I CD8+ T cells (FIG. 7a). The naïve OT-I cells also expanded-10-fold in response to the complex as compared to controls and upregulated CD44 (FIG. 7b). In light of the robust proliferation induced in naïve T cells, it was of interest to establish whether effector function was concomitantly induced. To test this question we adoptively transferred naïve OT-I CD8+ T cells into congenic C57BL/6 hosts and, using an in vivo killing assay, measured antigen specific lytic activity four days after treatment with IL-15/mL-15Ra-Fc or after infection with recombinant vesicular stomatitis virus expressing ovalbumin (VSV-OVA) for comparison. Interestingly, IL-15/rmIL-15Ra-Fc treatment resulted in induction of robust antigen-specific lytic activity, similar to the level obtained with virus infection (FIG. 7c). In addition to lytic activity, the majority of naïve OT-I CD8+ T cells activated by IL-15/IL-15Ra-Fc or VSV-OVA infection produced high levels of IFNg following in vitro restimulation with peptide (FIG. 7d). This result was in contrast to the negligible frequency of OT-I cells producing IFNg from control (PBS) and IL-15 treated mice (FIG. 7d). Thus, the induction of effector function in naïve CD8+ T cells by co-administration of IL-15Ra-Fc with IL-15 paralleled the activation obtained by infection.

Example 6

Figure 8:
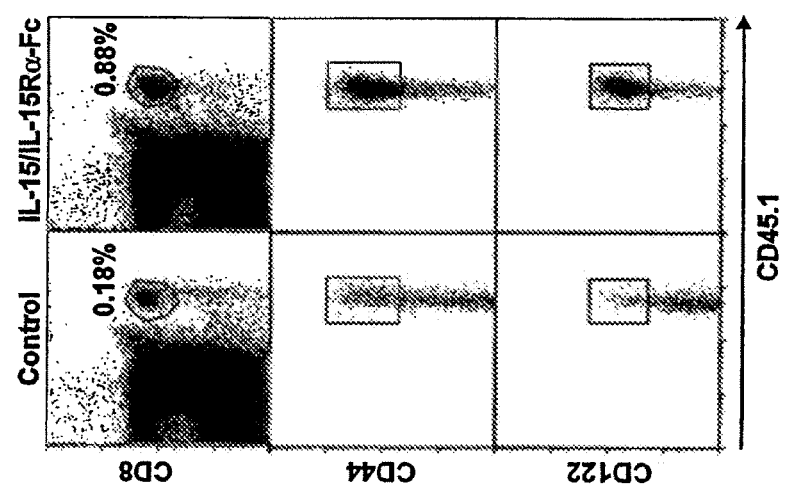
FIG. 8. Pre-coupled IL-15+IL-15Ra-Fc treatment generates memory cells from naïve CD8+ T cells. On day one, B6 mice received about $6 \times 10^6$ CFSE-labeled naïve OT-I-RAG−/− cells and on day 0 were treated i.p. with PBS or IL-15 (about 2.5 μg)+IL-15Ra-Fc (about 15 μg). 44 days later splenocytes were analyzed for percentage of donor OT-I CD8+ T cells (top panels) and OT-I expression of CD44 and CD122 (middle and bottom panels).
Figure 9:
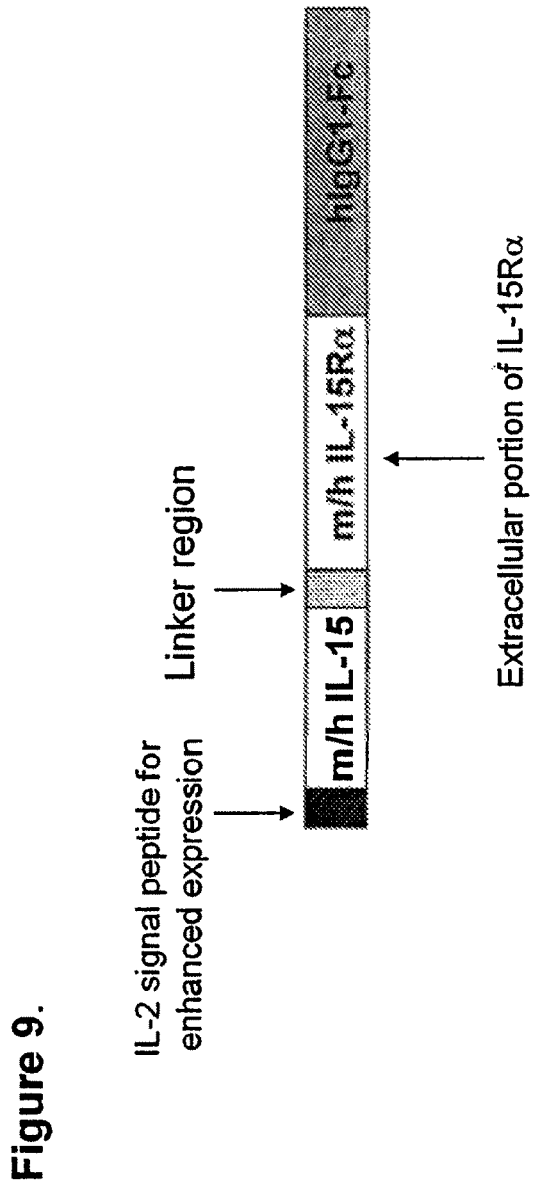
FIG. 9. Example of a IL-15+IL-15Ra-Fc fusion protein of the Invention—mouse version of the fusion protein. In this example, the general construct includes an IL-2 signal peptide for enhanced expression and processing, the IL-15 gene or portion thereof, a variable linker region to promote steric freedom and protein folding (may be of any desired length or sequence), the soluble or extracellular portion of the IL-15Ra gene, and the Fc portion of a human IgG. The genes or portions thereof of the human homologs can be substituted in a similar fashion. Similarly, IL-2 and IL-2Ra genes or portions thereof can be substituted in a chimeric construct, which also includes combinations with IL-15 or IL-15Ra genes or portions thereof.
Figure 10:
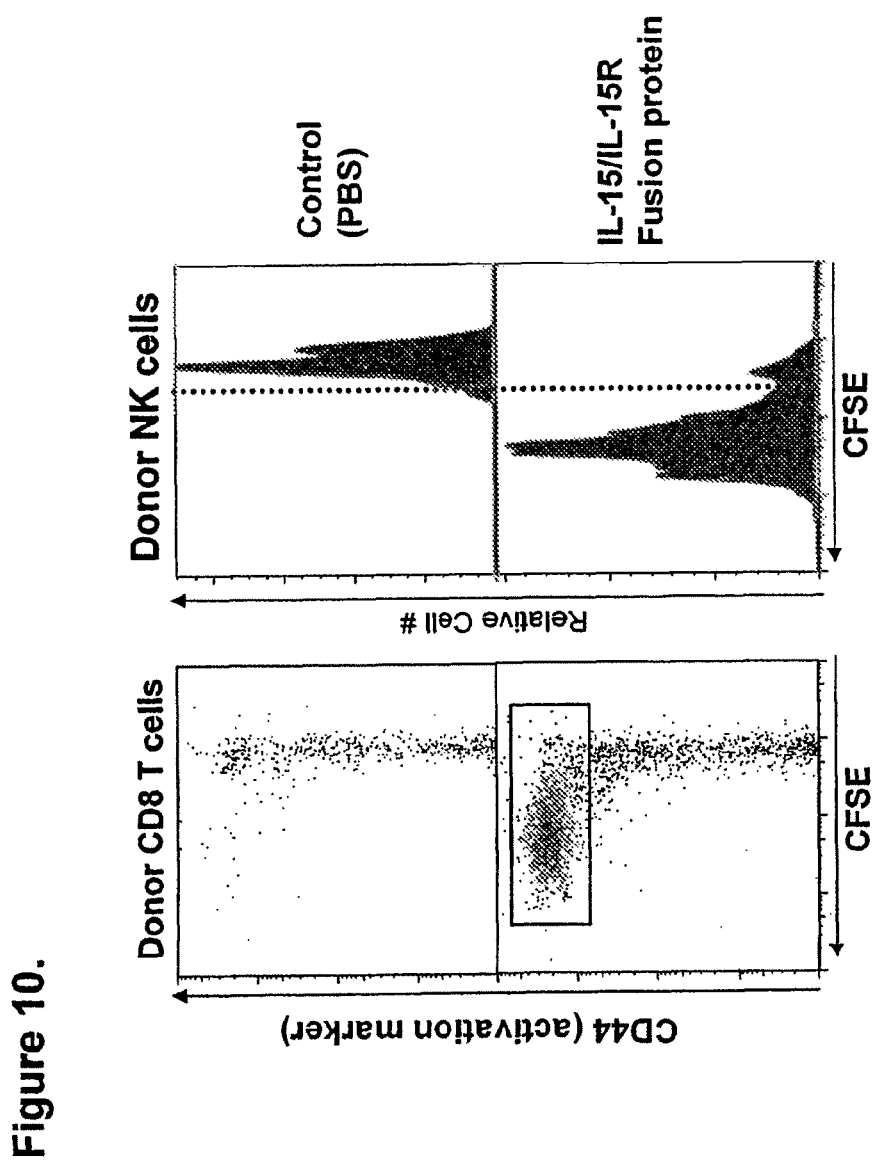
FIG. 10. The IL-15+IL-15Ra fusion protein elicits proliferation of CD8+ T cells and NK Cells. CFSE-labeled lymphocytes were transferred to normal mice that were then treated with ~10 μg of the Il-15+IL-15Ra fusion protein. Four days later, spleen cells were isolated and analyzed by flow cytometry.

Treatment of Naïve T Cells with Complexed IL-15/IL-15Ra-Fc Generates Memory CD8+ T Cells Although naïve T cells developed into effector cells in response to transpresented IL-15, it remained to be seen whether this was a transient effect or resulted in memory T cell development. Therefore, we analyzed the number and phenotype of OT-I T cells 44 days after naïve OT-I T cell transfer and IL-15/IL-15Ra-Fc treatment. At this time point a ~5-fold higher percentage of OT-I cells was present following IL-15/IL-15Ra administration as compared to untreated mice (FIG. 8, top panels). Moreover, nearly all of these cells expressed high levels of CD44 and CD122 (FIG. 8, middle and bottom panels). Thus, even in the absence of antigen, IL-15/IL-15Ra-Fc treatment was able to induce the development of memory CD8+ T cells.

Recent findings support the use of IL-15 as an adjuvant for vaccination, tumor immunotherapy, and immune system reconstitution in immunodeficiency. In the case of cancer treatment, induction of lymphopenia is now being employed to enhance the functional activity of adoptively transferred lymphocytes. This modality is based on the finding that CD8+ T cells undergoing lymphopenia-driven homeostatic proliferation differentiate into effector cells with lytic and cytokine producing activities. The differentiation of CD8+ T cells to effector and memory phenotype cells also requires MHC class I expression. Thus, the proliferation and functional activities induced by the IL-15/IL-15Ra-Fc complex in intact hosts mimicked homeostatic proliferation triggered by lymphopenia. Moreover, the level of proliferation obtained by treatment with the complex could not be achieved by high doses of IL-15 alone. Since the same cell producing IL-15 may also transpresent the cytokine, the availability of free IL-15Ra may be limited. In addition, the short half-life of IL-15 may be extended when complexed to the receptor. Therefore, treatment with IL-15 alone is unlikely to achieve the full therapeutic potential of the cytokine. The combined administration of IL-15/IL-15Ra may circumvent these problems and provide improved efficacy.

The mechanism of action of complexed IL-15/IL-15Ra was of particular interest given the current paradigm regarding the requirements for naïve and memory T cell homeostatic survival and proliferation. Under normal conditions, survival of both naïve and memory CD8+ T cells requires IL-7, while IL-15 is essential for homeostatic proliferation of memory CD8+ T cells and NK cells. In a lymphopenic environment, IL-7 is required for homeostatic proliferation of naïve CD8+ and CD4+ T cells, and plays a role, along with IL-15, in mediating CD8+ memory T cell homeostatic proliferation. Thus, it was unexpected that naïve CD8+ T cells responded vigorously to the IL-15/IL-15Ra complex. It should be noted however that in IL-15-/- mice, the naïve CD8+ T cell pool is decreased by about 50%, suggesting that either naïve CD8+ T cell development and/or survival requires IL-15. In any case, proliferation of naïve CD8+ T cells driven by receptor-bound IL-15/IL-15Ra was IL-7 independent and required IL-15Ra expression. This result indicated that naïve CD8+ T cells expressed sufficient levels of IL-15Ra to respond to IL-15/IL-15Ra but not to soluble IL-15 alone. In addition, naïve CD8+ T cells acquired effector function and subsequently developed into long-lived memory CD8+ T cells expressing high levels of CD44 and CD122. Interestingly, IL-15/IL-15Ra triggered activation of naïve or memory CD8+ T cells required MHC class I expression. While the survival of naïve CD8+ T cells is dependent on MHC, the survival of CD8 memory T cells is believed to be MHC independent. Thus, a requirement for MHC class I in memory cell proliferation induced by receptor complexed IL-15 was somewhat unexpected but supports a role for MHC in aspects of memory cell function, as has been previously demonstrated. Our findings illustrate the potential power of IL-15 in driving robust NK and CD8+ T cell expansion and effector differentiation in intact hosts. As with any adjuvant, it will be necessary to determine whether such activation may also enhance autoimmunity. Nevertheless, this system may provide the means to bolster immune reconstitution in immunodeficiencies or after bone marrow or stem cell transplantation. Moreover, while adoptive immunotherapy in the treatment of cancer may also be augmented by administration of IL-15/IL-15Ra, it is also possible that treatment with the complex alone could drive sufficient expansion of endogenous antigen-specific T cells, as well as NK/NKT cells, to provide some level of protection. Further studies are needed to determine the potential for this novel complex in immunotherapy.

TABLE 1

Combined IL-15Ra/IL-15 treatment is an effective anti-tumor therapy.[†]

| Tissue | Tumor Dose | Treatment PBS | IL-15 | IL-15Ra/IL-15 |
|---|---|---|---|---|
| Liver | $1 \times 10^5$ | 2-l; 0; 2-l; 3-l [‡] | 0; 3-l; 3-l; 2-l; 0 | 0; 0; 0; 0; 0 |
|  | $2 \times 10^5$ | 2-l; 4-l; 2-l; 1-m; 2-m | 11-m; 0; 1-s; 3-l; 5-l | 0; 0; 0; 0; 0 |
|  | $1 \times 10^6$ | 24-l; 14; 9-l; 4-l | ND | 0; 2-s; 2-s; 0 |
| Lung | $1 \times 10^5$ | 0; 0; 0; 2-l [‡] | 0; 1-s; 23-s; 4-m; 100-s | 0; 0; 0; 0; 0 |
|  | $2 \times 10^5$ | 2-m; 2-m; 2-m; 6 (1-l; 5-s); 52 (2-l; 50-s) | 2-m; 3-m; 13 (1-l; 12-s); 2-m; 50-s | 1-s; 3-s; 100-s; 0; 0 |
|  | $1 \times 10^6$ | 65-l; 61-l; 81-l; 65-l | ND[£] | 28-s; 33-s; 22-s; 42-s |
| Other tumors* | $1 \times 10^5$ | +++ 5/5 | +++ 5/5 | § 5/5 |
|  | $2 \times 10^5$ | +++ 3/5; § 2/5 | +++ 4/5; § 1/5 | + 1/5; § 4/5 |
|  | $1 \times 10^6$ | ++++ 4/4 | ND | + 1/4; § 3/4 |

[†]The indicated dose of B16-F1 melanoma was given intravenously, and one and 10 days later mice were treated intraperitoneally. with PBS, 2.5 ug IL-15 or 2.5 ug IL-15 + 15 ug sIL-15Ra-Fc. 21 days after tumor inoculation the tumor burden was assessed.
Tumor size: (s) ≈ microscopic to 2 mm; (m) ≈ 2-5 mm; (l) > 5 mm
[‡] Died before analysis
[£]Not done
*Includes tumors in the body cavity including in kidney, pancreas, lymph nodes and other tissues. § = no tumors observed; + = 1 small tumor; +++ = multiple medium to large tumors; ++++ = large tumor masses.

Exemplary Methods

Mice. C57BL/6-Ly 5.1 mice were purchased from The Jackson Laboratory (B Harbor, Me.). C57BL/6-Ly 5.2 mice were purchased from Charles River. The OT-I mouse line was generously provided by Dr. W. R. Heath (WEHI, Parkville, Australia) and Dr. F. Carbone (Monash Medical School, Prahan, Victoria, Australia) and was maintained as a C57BL/6-Ly5.2 line on a RAG−/− background.

IL-15Ra−/− mice22 were generously provided by Dr. Averil Ma (UCSF). Spleen cells from IL-2Rb−/− mice were generously provided by Dr. Michael Farrar (UMINN). DTR transgenic mice were a gift from Dr. D. Littman (Skirball Institute, NY, N.Y.). The mice were backcrossed 10 times to C57BL/6 at the UCONN Health Center facilities. DTR Tg+ mice were screened by PCR of tail DNA as previously described. IL-7−/− mice were originally obtained from DNAX Research Institute of Molecular and Cellular Biology (Palo Alto, Calif.) and were maintained on a C57BL/6×129/Ola hybrid background.

IL-15 treatment. Recombinant mouse IL-15Ra-Fc chimeric molecule was purchased from R&D Systems, Inc. (Minneapolis, Minn.). hIL-15 and rmIL-15Ra-Fc, both suspended in PBS, were mixed and incubated for about 30 min at about 37° C. Each mouse, unless specifically noted, received 2.5 µg IL-15 and 15 µg rmIL-15Ra-Fc in 200 ul PBS i.p.

Human. A DNA sequence encoding the extracellular domain of human IL-15 Ra-E3, which lacks exon 3, (Anderson, D. et al., 1995, J. Biol. Chem. 270:29862-29869) was fused to the 6× histidine tagged Fc of human IgG1 via a polypeptide linker. The chimeric protein was expressed in St 21 cells using a baculovirus expression system. Molecular Mass. The recombinant mature human IL-15 Ra/Fc is a disulfide-linked homodimeric protein. Based on N-terminal sequencing, the recombinant human IL-15Ra protein has Ile 31 at the amino-terminus. The reduced human IL-15 Ra/Fc monomer has a calculated molecular mass of approximately 42.6 kDa. As a result of glycosylation, the recombinant monomer migrates as an approximately 60-70 kDa protein in SDS-PAGE under reducing conditions.

Mouse. A DNA sequence encoding the signal peptide from human CD33, joined with amino acid residues 33-205 of the extracellular domain of mouse IL-15 Ra (Giri, J. G. et al., 1995, EMBO. 14:3654-3663) was fused to the Fc region of human IgG1 via a polypeptide linker. The chimeric protein was expressed in a mouse myeloma cell line, NS0. Molecular Mass. The recombinant mature mouse IL-15 Ra-Fc is a disulfide-linked homodimeric protein. Based on N-terminal sequencing, the recombinant mouse IL-15 Ra-Fc protein has Gly 33 at the amino-terminus. The reduced mouse IL-15 Ra-Fc monomer has a calculated molecular mass of 44.9 kDa. As a result of glycosylation, the recombinant protein migrates as an approximately 80-90 kDa protein in SDS-PAGE under reducing conditions. In addition to the full-length IL-15 Ra-Fc, this preparation also contains a small amount (10%) of free IL-15 Ra and Fc generated by proteolytic cleavage. Free IL-15 Ra and Fc migrate as approximately 42 kDa and 35 kDa proteins, respectively, in SDS-PAGE under reducing conditions.

CFSE labeling of cells and adoptive transfer. Lymphocytes were isolated from spleen and/or peripheral lymph nodes (as described in Isolation of lymphocyte populations) and resuspended in HBSS (about 1% HGPG) at 10×10$^6$ cells/ml and then warmed to 37° C. Cells were incubated for about 10 min with CFSE (0.01 mM; Molecular Probes, Eugene, Oreg.) and the reaction was squelched with HBSS with about 1% HGPG and about 5% FCS. Cells were washed twice with HBSS (about 1% HGPG). CFSE-labeled cells were resuspended (1-20×10$^6$ cells) in PBS and injected i.v. into congenic mice. Cells were isolated at the indicated times and analyzed for the presence of donor cells using CD45 allele status and their expression of surface markers and CFSE intensity.

Isolation of lymphocyte populations and immunofluorescence analysis. Single-cell suspensions were created in HBSS (with about 1% HGPG) by homogenizing spleens using frosted glass slides. Red blood cells were lysed and splenocytes were filtered through Nitex. At the indicated time points, lymphocytes were isolated and donor CFSE-labeled cells were detected using their CD45 allele status or OVA-specific donor cells were detected using an H-2 Kb tetramer containing the OVA-derived peptide SIINFEKL produced as previously described. For staining, lymphocytes were suspended in PBS/about 0.2% BSA/about 0.1% NaN3 (FACS buffer) at a concentration of about 3-15×10$^6$/200 µl. When staining for tetramer, cells were incubated at room temperature for about 1 h with OVA-tetramer APC plus the appropriate dilution of anti-CD8 PerCp. Cells were washed with FACS buffer and stained with anti-CD44 PE at about 4° C. for about 20 min, washed and then fixed in PBS with about 3% paraformaldehyde. Relative fluorescence intensities were measured with a FACScalibur (BD Biosciences, San Jose, Calif.). Data were analyzed using FlowJo Software (Tree Star, San Carlos, Calif.).

In vivo cytotoxicity assay. This assay was performed essentially as previously described. Normal spleen cells were labeled to low (about 0.25 um) or high (about 2.5 um) CFSE levels and CFSE high cells were incubated with about 1 µg/ml SIINFEKL peptide for about 45 min at about 37° C. Equal numbers ($10 \times 10^6$) of each population were mixed and injected i.v. into OT-I transferred mice that were either untreated or that were treated with IL-15/IL-15Ra or were infected with $1 \times 10^5$ pfu of vesicular stomatitis virus expressing chicken ovalbumin four days earlier. Four hours later, spleen cells were analyzed for the presence of CFSEhigh and CFSElow populations Percent lysis=[1−(ratio unprimed/ratio primed)]×100. Ratio=percent CFSElow/percent CFSEhigh.

Intracellular detection of IFN-g. Lymphocytes were isolated from the spleen and cultured for about 5 h with about 1 µg/ml Golgistop (BD PharMingen), with or without about 1 µg/ml of the OVA-derived peptide SIINFEKL. After culture, cells were stained for surface molecules, then fixed, and cell membranes were permeabilized in cytofix/cytoperm solution (BD PharMingen) and stained with anti-IFN-gPE or control rat IgG1 PE. Cells were then washed and the fluorescence intensity was measured on a FACScalibur.

Bone marrow chimeras. Femurs and tibias were taken from CD11c-DTR Tg+ mice or non-Tg littermates. The bone marrow (BM) was flushed out with a syringe and passed through a 70 um nylon mesh to generate a single cell suspension. Red blood cells (RBC) were lysed and the cells resuspended in HBSS supplemented with HEPES, L-glutamine, penicillin, streptomycin, gentamycin sulphate (HBSS-HGPG). To remove mature T cells from the BM, cells were incubated with anti-Thy1 ascites fluid (T24), washed once in HBSS-HGPG then incubated with Low-Tox-M rabbit complement (Cedarlane Laboratories, Ontario, Canada) for about 45 min, at about 37° C. CD45.1 recipient B6 mice were irradiated (about 1,000 rad) before about $2$-$5 \times 10^6$ bone marrow cells were transferred i.v. The mice were allowed to rest 8 weeks before use. Diphtheria toxin (Sigma, St Louis, Mo.) in PBS was administered i.p. to mice at about 4 ng/g bodyweight. Chimeras received DT one day prior to cytokine treatment, a dose just prior to cytokine treatment and a final dose on day three post cytokine treatment.

REFERENCES

The following references are hereby incorporated by reference in their entirety for all purposes.

1. Grabstein, K. H. et al. Cloning of a T cell growth factor that interacts with the beta chain of the interleukin-2 receptor. *Science* 264, 965-968 (1994).
2. Bamford, R. N. et al. The Interleukin (Il)-2 Receptor-Beta Chain Is Shared by Il-2 and A Cytokine, Provisionally Designated Il-T, That Stimulates TCell Proliferation and the Induction of Lymphokine-Activated Killer-Cells. *Proceedings of the National Academy of Sciences of the United States of America* 91, 4940-4944 (1994).
3. Bamford, R. N., Battiata, A. P., Burton, J. D., Sharma, H. & Waldmann, T. A. Interleukin (IL) 15/IL-T production by the adult T-cell leukemia cell line HuT-102 is associated with a human T-cell lymphotrophic virus type I region/IL-15 fusion message that lacks many upstream AUGs that normally attenuates IL-15 mRNA translation. *Proc. Natl. Acad. Sci. U.S.A* 93, 2897-2902 (1996).
4. Nishimura, H. et al. A novel autoregulatory mechanism for transcriptional activation of the IL-15 gene by a nonsecretable isoform of IL-15 generated by alternative splicing. *FASEB J* 19, 19-28 (2005).
5. Villinger, F. et al. IL-15 is superior to IL-2 in the generation of long-lived antigen specific memory CD4 and CD8 T cells in rhesus macaques. *Vaccine* 22, 3510-3521 (2004).
6. Burton, J. D. et al. A Lymphokine, Provisionally Designated Interleukin-T and Produced by A Human Adult T-Cell Leukemia Line, Stimulates T-Cell Proliferation and the Induction of Lymphokine-Activated Killer-Cells. *Proceedings of the National Academy of Sciences of the United States of America* 91, 4935-4939 (1994).
7. Giri, J. G. et al. Identification and cloning of a novel IL-15 binding protein that is structurally related to the alpha chain of the IL-2 receptor. *EMBO J* 15, 3654-3633 (1995).
8. Giri, J. G. et al. Utilization of the beta and gamma chains of the IL-2 receptor by the novel cytokine IL-15. *EMBO J.* 13, 2822-2830 (1994).
9. Berard, M., Brandt, K., Paus, S. B. & Tough, D. F. IL-15 promotes the survival of naive and memory phenotype CD8(+) T cells. *Journal of Immunology* 170, 5018-5026 (2003).
10. Park, C. S., Yoon, S. O., Armitage, R. J. & Choi, Y. S. Follicular dendritic cells produce IL-15 that enhances germinal center B cell proliferation in membrane-bound form. *J. Immunol.* 173, 6676-6683 (2004).
11. Goldrath, A. W. et al. Cytokine requirements for acute and basal homeostatic proliferation of naive and memory CD8+ T cells. *J. Exp. Med.* 195, 1515-1522 (2002).
12. Schluns, K. S. et al. Distinct cell types control lymphoid subset development by means of IL-15 and IL-15 receptor alpha expression. *Proc. Natl. Acad. Sci. U.S.A* 101, 5616-5621 (2004).
13. Oh, S., Perera, L. P., Burke, D. S., Waldmann, T. A. & Berzofsky, J. A. IL-15/IL-15R{alpha}-mediated avidity maturation of memory CD8+ T cells. *Proc. Natl. Acad Sci. U.S.A* 101, 15154-15159 (2004).
14. Armitage, R. J., Macduff, B. M., Eisenman, J., Paxton, R. & Grabstein, K. H. IL-15 has stimulatory activity for the induction of B cell proliferation and differentiation. *J. Immunol.* 154, 483-490 (1995).
15. Becker, T. C. et al. Interleukin 15 is required for proliferative renewal of virus-specific memory CD8 T cells. *J. Exp. Med.* 195, 1541-1548 (2002).
16. Cooper, M. A. et al. In vivo evidence for a dependence on interleukin 15 for survival of natural killer cells. *Blood* 100, 3633-3638 (2002).
17. Schluns, K. S., Williams, K., Ma, A., Zheng, X. X. & Lefrançois, L. Cutting Edge: Requirement for IL-15 in the generation of primary and memory antigen-specific CD8 T cells. *J. Immunol.* 168, 4827-4831 (2002).
18. Kennedy, M. K. et al. Reversible defects in natural killer and memory CD8 T cell lineages in Interleukin-15-deficient mice. *J. Exp. Med* 191, 771-780 (2000).
19. Ku, C. C., Murakami, M., Sakamoto, A., Kappler, J. & Marrack, P. Control of homeostasis of CD8+ memory T cells by opposing cytokines. *Science* 288, 675-678 (2000).
20. Tan, J. T. et al. Interleukin (IL)-15 and IL-7 jointly regulate homeostatic proliferation of memory phenotype CD8+ cells but are not required for memory phenotype CD4+ cells. *J. Exp. Med.* 195, 1523-1532 (2002).

21. Ohteki, T., Suzue, K., Maki, C., Ota, T. & Koyasu, S. Critical role of IL-15-IL-15R for antigen-presenting cell functions in the innate immune response. *Nat. Immunol.* 2, 1138-1143 (2001).
22. Lodolce, J. P. et al. IL-15 receptor maintains lymphoid homeostasis by supporting lymphocyte homing and proliferation. *Immunity* 9, 669-676 (1998).
23. Judge, A. D., Zhang, X., Fujii, H., Surh, C. D. & Sprent, J. Interleukin 15 controls both proliferation and survival of a subset of memory-phenotype CD8(+) T Cells. *J. Exp. Med* 196, 935-946 (2002).
24. Ferrari-Lacraz, S. et al. Targeting IL-15 Receptor-Bearing Cells with an Antagonist Mutant IL-15/Fc Protein Prevents Disease Development and Progression in Murine Collagen-Induced Arthritis. *J. Immunol* 173, 5818-5826 (2004).
25. Ruchatz, H., Leung, B. P., Wei, X. Q., McInnes, I. B. & Liew, F. Y. Soluble IL-15 receptor alpha-chain administration prevents murine collagen-induced arthritis: a role for IL-15 in development of antigen-induced immunopathology. *J. Immunol.* 160, 5654-5660 (1998).
26. Smith, X. G. et al. Selective blockade of IL-15 by soluble IL-15 receptor alpha-chain enhances cardiac allograft survival. *J. Immunol.* 165, 3444-3450 (2000).
27. Rubinstein, M. P. et al. Systemic Administration of IL-15 Augments the Antigen-Specific Primary CD8+ T Cell Response Following Vaccination with Peptide-Pulsed Dendritic Cells. *J. Immunol* 169, 4928-4935 (2002).
28. Tsunobuchi, H. et al. A Protective Role of Interleukin-15 in a Mouse Model for Systemic Infection with Herpes Simplex Virus. *Viral.* 275, 57-66 (2000).
29. Oh, S., Berzofsky, J. A., Burke, D. S., Waldmann, T. A. & Perera, L. P. Coadministration of HIV vaccine vectors with vaccinia viruses expressing IL-15 but not IL-2 induces long-lasting cellular immunity. *PNAS* 100, 3392-3397 (2003).
30. Khan, I. A. & Kasper, L. H. IL-15 augments CD8+ T cell-mediated immunity against *Toxoplasma gondii* infection in mice.
31. Maeurer, M. J. et al. Interleukin-7 or interleukin-15 enhances survival of *Mycobacterium tuberculosis*-infected mice. *Infect. Immun.* 68, 2962-2970 (2000).
32. Umemura, M., Nishimura, H., Hirose, K., Matsuguchi, T. & Yoshikai, Y. Overexpression of IL-15 in vivo enhances protection against *Mycobacterium bovis bacillus* Calmette-Guerin infection via augmentation of NK and T cytotoxic 1 responses. *J. Immunol,* 167, 946-956 (2001).
33. Nguyen, L. T. et al. TNF receptor 1 (TNFR1) and CD95 are not required for T cell deletion after virus infection but contribute to peptide-induced deletion under limited conditions. *Eur. J. Immunol.* 30, 683-688 (2000).
34. Chitnis, V., Pahwa, R. & Pahwa, S. Determinants of HIV-Specific CD8 T-cell responses in HIV-infected pediatric patients and enhancement of HIV-gagspecific responses with exogenous IL-15. *Clin. Immunol* 107, 36-45 (2003).
35. Castelli, J., Thomas, E. K., Gilliet, M., Liu, Y. J. & Levy, J. A. Mature Dendritic cells can enhance CD8+ cell non-cytotoxic anti-HIV responses: the role of IL-15. *Blood* 103, 2699-2704 (2004).
36. Lum, J. J. et al. Differential Effects of Interleukin-7 and Interleukin-15 on NK Cell Anti-Human Immunodeficiency. Virus Activity. *J. Virol.* 78, 6033-6042 (2004).
37. Forcina, G. et al. Interleukin-15 modulates interferon-gamma and betachemokine production in patients with HIV infection: implications for immune-based therapy. *Cytokine* 25, 283-290 (2004).
38. Mastroianni, C. M. et al. Interleukin-15 enhances neutrophil functional activity in patients with human immunodeficiency virus infection. *Blood* 96, 1979-1984 (2000).
39. Bamford, R. N., DeFilippis, A. P., Azimi, N., Kurys, G. & Waldmann, T. A. The 5' untranslated region, signal peptide, and the coding sequence of the carboxyl terminus of IL-15 participate in its multifaceted translational control. *Journal of Immunology* 160, 4418-4426 (1998).
40. Mueller, Y. M. et al. IL-15 enhances survival and function of HIV-specific CD8+ T cells. *Blood* 101, 1024-1029 (3 A.D.).
41. Alpdogan, O. et al. Interleukin-15 enhances immune reconstitution after allogenic bone marrow transplantation. *Blood* 105, 865-873 (2005).
42. Chapoval, A. I., Fuller, J. A., Kremlev, S. G., Kamdar, S. J. & Evans, R. Combination chemotherapy and IL-15 administration induce permanent tumor regression in a mouse lung tumor model: NK and T cell-mediated effects antagonized by B cells. *J. Immunol.* 161, 6977-6984 (1998).
43. Wysocka, M. et al. Enhancement of the host immune responses in cutaneous T-cell lymphoma by CpG oligodeoxynucleotides and IL-15. *Blood* 104, 4142-4149 (2004).
44. Klebanoff, C. A. et al. IL-15 enhances the in vivo antitumor activity of tumorreactive CD8+ T cells. *PNAS* 101, 1969-1974 (4 A.D.).
45. de Jong, J. L., Farner, N. L., Widmer, M. B., Giri, J. G. & Sondel, P. M. Interaction of IL-15 with the shared IL-2 receptor beta and gamma c subunits. The IL-15/beta/gamma c receptor-ligand complex is less stable than the IL-2/beta/gamma c receptor-ligand complex. *J. Immunol* 156, 1339-1348 (1996).
46. Budagian, V. et al. Reverse signaling through membrane-bound interleukin-15. *J. Biol. Chem.* 279, 42192-42201 (2004).
47. Sandau, M. M., Schluns, K. S., Lefrancois, L. & Jameson, S. C. Transpresentation of IL-15 by bone marrow-derived cells necessitates expression of IL-15 and IL-15R by the same cells. *J. Immunol.* 173, in press (2004).
48. Burkett, P. R. et al. IL-15Ralpha expression on CD8+ T cells is dispensable for T cell memory. *Proc. Natl. Acad. Sci. U S. A* 100, 4724-4729 (2003).
49. Dubois, S., Mariner, J., Waldmann, T. A. & Tagaya, Y. IL-15Ralpha recycles and presents IL-15 In trans to neighboring cells. *Immunity* 17. 537-547 (2002).
50. Schluns, K. S., Klonowski, K. D. & Lefrançois, L. Trans-regulation of memory CD8 T cell proliferation by IL-15Ra+ bone marrow-derived cells. *Blood* DOI 10.1182/blood-2003-08-2814, (2004).
51. Burkett, P. R. et al. Coordinate expression and trans presentation of interleukin (IL)-15Ralpha and IL-15 supports natural killer cell and memory CD8+ T cell homeostasis. *J Exp. Med.* 200, 825-834 (2004).
52. Lodolce, J. P., Burkett, P. R., Boone, D. L., Chien, M. & Ma, A. T cell independent interleukin 15Ralpha signals are required for bystander proliferation. *J Exp. Med.* 194, 1187-1194 (2001).
53. Koka, R. et al. Interleukin (IL)-15R[alpha]-deficient natural killer cells survive in normal but not IL-15R[alpha]-deficient mice. *J. Exp. Med.* 197, 977-984 (2003).
54. Carson, W. E. et al. Interleukin (IL) 15 is a novel cytokine that activates human natural killer cells via components of the IL-2 receptor. *J. Exp. Med.* 180, 1395-1403 (1994).
55. Dunne, J. et al. Selective expansion and partial activation of human NK cells and NK receptor-positive T cells by IL-2 and IL-15. *J. Immunol.* 167, 3129-3138 (2001).

56. Warren, H. S., Kinnear, B. F., Kastelein, R. L. & Lanier, L. L. Analysis of the costimulatory role of IL-2 and IL-15 in initiating proliferation of resting (CD56dim) human NK cells. *J. Immunol.* 156, 3254-3259 (1996).
57. Murali-Krislma, K. et al. Persistence of memory CD8 T cells in MHC class I-deficient mice. *Science* 286, 1377-1381 (1999).
58. Goldrath, A. W. & Bevan, M. J. Low-Affinity Ligands for the TCR Drive Proliferation of Mature CD8+ TCells in Lymphopenic Hosts. *Immunity* 11, 183-190 (2000).
59. Kieper, W. C. & Jameson, S. C. Homeostatic expansion and phenotypic conversion of naive T cells in response to self peptide/MHC ligands. *PNAS* 96, 13306-13311 (2000).
60. Schluns, K. S., Kieper, W. C., Jameson, S. C. & Lefrançois, L. Interleukin-7 mediates the homeostasis of naive and memory CD8 T cells in vivo. *Nat. Immunol.* 1, 426-432 (2000).
61. Brocker, T. Survival of mature CD4 T lymphocytes is dependent on major histocompatibility complex class II-expressing dendritic cells. *J. Exp. Med.* 186, 1223-1232 (1997).
62. Jung, S. et al. In vivo depletion of CD11c(+) dendritic cells abrogates priming of CD8(+) T cells by exogenous cell-associated antigens. *Immunity* 17, 211-220 (2002).
63. Zammit, D. J., Cauley, L. S., Pham, Q.-M. & Lefrançois, L. Dendritic cells maximize the memory CD8 T cell response to infection. Immunity in press, (2005).
64. Klebanoff, C. A. et al. IL-15 enhances the in vivo antitumor activity of tumorreactive CD8+ T cells. *Proc. Natl. Acad. Sci. U S. A* 101, 1969-1974 (2004).
65. Roychowdhury, S. et al. Failed adoptive immunotherapy with tumorspecific T cells: reversal with low-dose interleukin 15 but not low-dose interleukin 2. *Cancer Res.* 64, 8062-8067 (2004).
66. Zeng, R. et al. Synergy of IL-21 and IL-15 in regulating CD8+ T cell expansion and function. *J. Exp. Med* 201, 139-148 (2005).
67. Alpdogan, O. & van den Brink, M. R. M. IL-7 and IL-15: therapeutic cytokines for immunodeficiency. *Trends Immunol.* 26, 56-64 (2005).
68. Dummer, W. et al. T cell homeostatic proliferation elicits effective antitumor autoimmunity. *J. Clin. Invest* 110, 185-192 (2002).
69. Baccala, R., Gonzalez-Quintial, R., Dummer, W. & Theofilopoulos, A. N. Tumor immunity via homeostatic T cell proliferation: mechanistic aspects and clinical perspectives. *Springer Semin Immunopathol* published online, (2005).
70. Wrzesinski, C. & Restifo, N. P. Less is more: lymphodepletion followed by hematopoietic stem cell transplant anments adoptive T-cell-based antitumor immunotherapy. *Curr. Opin. Immunol.* 17, 195-201 (2005).
71. Dudley, M. E. et al. Adoptive cell transfer therapy following nonmyeloablative but lymphodepleting chemotherapy for the treatment of patients with refractory metastatic melanoma. *J. Clin. Oncol.* 23, 2346-2357 (2005).
72. Porter, D. L. & June, C. H. T-cell reconstitution and expansion after hematopoietic stem cell transplantation: 'T' it up! *Bone Marrow Transplant.* (2005).
73. Cho, B. K., Rao, V. P., Ge, Q., Eisen, H. N. & Chen, J. Homeostasis-stimulated proliferation drives naive T cells to differentiate directly into memory T cells. *J. Exp. Med.* 192, 549-556 (2000).
74. Ruckert, R. et al. Dendritic cell-derived IL-15 controls the induction of CD8 T cell immune responses. *Eur. J. Immunol.* 33, 3493-3503 (2003).
75. Prlic, M., Blazar, B. R., Farrar, M. A. & Jameson, S. C. In vivo survival and homeostatic proliferation of natural killer cells. *J. Exp. Med.* 197, 967-976 (2003).
76. Kassiotis, G., Garcia, S., Simpson, E. & Stockinger, B. Impairment of immunological memory in the absence of MHC despite survival of memory T cells. *Nat. Immunol.* 3, 244-250 (2002).
77. Lyons, A. B. & Parish, C. R. Determination of lymphocyte division by flow cytometry. *J. Immunol. Methods* 171, 131-137 (1994).
78. Altman, J. D. et al. Phenotypic analysis of antigen-specific T lymphocytes. *Science* 274, 94-96 (1996).
79. Masopust, D., Jiang, J., Shen, H. & Lefrançois, L. Direct analysis of the dynamics of the intestinal mucosa CD8 T cell response to systemic virus infection. *J. Immunol.* 166, 2348-2356 (2001).
80. Oehen, S. & Brduscha-Riem, K. Differentiation of naive CTL to effector and memory CTL: correlation of effector function with phenotype and cell division. *J. Immunol* 161, 5338-5346 (1998).
81. Kim, S. K. et al. Generation of mucosal cytotoxic T cells against soluble protein by tissue-specific environmental and costimulatory signals. *Proc. Natl. Acad. Sci. USA* 95, 10814-10819 (1998).

We claim:

1. A method for treating cancer, comprising administering to a human in need thereof a therapeutically effective amount of a composition, wherein the composition comprises:
   (a) a purified complex comprising an interleukin-15 (IL-15) polypeptide bound to a purified chimeric polypeptide comprising a soluble form of an IL-15 receptor alpha (IL-15Ra) polypeptide that is covalently linked to the Fc portion of an antibody; or
   (b) a purified IL-15 polypeptide and a purified chimeric polypeptide comprising the soluble form of an IL-15Ra polypeptide that is covalently linked to the Fc portion of an antibody.

2. The method of claim 1, wherein the composition comprises a purified complex comprising an IL-15 polypeptide bound a purified chimeric polypeptide comprising a soluble form of an IL-15Ra polypeptide that is covalently linked to the Fc portion of an antibody.

3. The method of claim 1, wherein the composition comprises a purified IL-15 polypeptide and a purified chimeric polypeptide comprising the soluble form of an IL-15Ra polypeptide that is covalently linked to the Fc portion of an antibody.

4. The method of claim 2, wherein the IL-15 polypeptide is:
   (i) (a) encoded by a nucleic acid that is at least 80% identical to SEQ ID NO: 2 over the entire length of SEQ ID NO: 2; or (b) at least 95% identical to the amino acid sequence of SEQ ID NO: 6 over the length of the mature form of SEQ ID NO: 6; and
   (ii) capable of forming a complex with IL-15Ra polypeptide.

5. The method of claim 2, wherein the IL-15 polypeptide has the amino acid sequence of SEQ ID NO: 6.

6. The method of claim 2, wherein the soluble form of the IL-15Ra polypeptide is:
   (i) a soluble form of an IL-15Ra polypeptide and the IL-15Ra polypeptide is (a) encoded by a nucleic acid that is at least 80% identical to SEQ ID NO: 4 over the entire length of SEQ ID NO: 4; or (b) at least 95% identical to the amino acid sequence of SEQ ID NO: 8 over the length of the mature form of SEQ ID NO: 8; and
   (ii) capable of forming a complex with IL-15 polypeptide.

7. The method of claim 2, wherein the soluble form of the IL-15Ra polypeptide:
   (i) has the amino acid sequence of the extracellular domain of an IL-15Ra polypeptide and the IL-15Ra polypeptide is (a) encoded by a nucleic acid that is at least 80% identical to SEQ ID NO: 4 over the entire length of SEQ ID NO: 4; or (b) at least 95% identical to the amino acid sequence of SEQ ID NO: 8 over the length of the mature form of SEQ ID NO: 8; and
   (ii) is capable of forming a complex with IL-15 polypeptide.

8. The method of claim 6, wherein the IL-15Ra polypeptide has the amino acid sequence of SEQ ID NO: 8.

9. The method of claim 7, wherein the IL-15Ra polypeptide has the amino acid sequence of SEQ ID NO: 8.

10. The method of claim 4, wherein the soluble form of the IL-15Ra polypeptide is:
    (i) a soluble form of an IL-15Ra polypeptide and the IL-15Ra polypeptide is (a) encoded by a nucleic acid that is at least 80% identical to SEQ ID NO: 4 over the entire length of SEQ ID NO: 4; or (b) at least 95% identical to the amino acid sequence of SEQ ID NO: 8 over the length of the mature form of SEQ ID NO: 8; and
    (ii) capable of forming a complex with IL-15 polypeptide.

11. The method of claim 4, wherein the soluble form of the IL-15Ra polypeptide:
    (i) has the amino acid sequence of the extracellular domain of an IL-15Ra polypeptide and the IL-15Ra polypeptide is (a) encoded by a nucleic acid that is at least 80% identical to SEQ ID NO: 4 over the entire length of SEQ ID NO: 4; or (b) at least 95% identical to the amino acid sequence of SEQ ID NO: 8 over the length of the mature form of SEQ ID NO: 8; and (ii) is capable of forming a complex with IL-15 polypeptide.

12. The method of claim 10, wherein the IL-15Ra polypeptide has the amino acid sequence of SEQ ID NO: 8.

13. The method of claim 11, wherein the IL-15Ra polypeptide has the amino acid sequence of SEQ ID NO: 8.

14. The method of claim 5, wherein the soluble form of the IL-15Ra polypeptide is:
   (i) a soluble form of an IL-15Ra polypeptide and the IL-15Ra polypeptide is (a) encoded by a nucleic acid that is at least 80% identical to SEQ ID NO: 4 over the entire length of SEQ ID NO: 4; or (b) at least 95% identical to the amino acid sequence of SEQ ID NO: 8 over the length of the mature form of SEQ ID NO: 8; and
   (ii) capable of forming a complex with IL-15 polypeptide.

15. The method of claim 5, wherein the soluble form of the IL-15Ra polypeptide:
   (i) has the amino acid sequence of the extracellular domain of an IL-15Ra polypeptide and the IL-15Ra polypeptide is (a) encoded by a nucleic acid that is at least 80% identical to SEQ ID NO: 4 over the entire length of SEQ ID NO: 4; or (b) at least 95% identical to the amino acid sequence of SEQ ID NO: 8 over the length of the mature form of SEQ ID NO: 8; and (ii) is capable of forming a complex with IL-15 polypeptide.

16. The method of claim 14, wherein the IL-15Ra polypeptide has the amino acid sequence of SEQ ID NO: 8.

17. The method of claim 15, wherein the IL-15Ra polypeptide has the amino acid sequence of SEQ ID NO: 8.

18. The method of claim 2, wherein the composition is administered by a parenteral route.

19. The method of claim 2, wherein the composition is administered by an intravenous route, subcutaneous route or intramuscular route.

20. The method of claim 2, wherein the cancer is lymphoma.

21. The method of claim 2, wherein the cancer is leukemia.

22. The method of claim 2, wherein the cancer is prostate cancer, uterus cancer, liver cancer, melanoma, neoplasm, adenocarcinoma, lung cancer, kidney cancer or pancreatic cancer.

23. The method of claim 2, wherein the human is lymphopenic.

24. The method of claim 2, which further comprises administering another active ingredient to the human.

25. The method of claim 24, wherein the active ingredient is anti-oncogenic.

* * * * *

UNITED STATES PATENT AND TRADEMARK OFFICE
CERTIFICATE OF CORRECTION

PATENT NO. : 9,365,630 B2
APPLICATION NO. : 14/567317
DATED : June 14, 2016
INVENTOR(S) : Leo Lefrancois and Thomas A. Stoklasek Page 1 of 1

It is certified that error appears in the above-identified patent and that said Letters Patent is hereby corrected as shown below:

In the Specification

At Column 1, Line 18, replace "The U.S. Government has certain rights in this invention pursuant to Grant No.: R01-A151583 Role of IL-15 in CD8 T Cell Development and Response, awarded by the National Institutes of Health (NIH)." with --This invention was made with government support under AI051583 awarded by the National Institutes of Health. The government has certain rights in the invention.--

Signed and Sealed this
Twenty-fourth Day of June, 2025

Coke Morgan Stewart
*Acting Director of the United States Patent and Trademark Office*

SEQUENCE LISTING

```
<160> NUMBER OF SEQ ID NOS: 16

<210> SEQ ID NO 1
<211> LENGTH: 495
<212> TYPE: DNA
<213> ORGANISM: Mus musculus IL-15 cDNA

<400> SEQUENCE: 1
atgaaaattt tgaaaccata tatgaggaat acatccatct cgtgctactt gtgtttcctt      60
ctaaacagtc acttttttaac tgaggctggc attcatgtct tcattttggg ctgtgtcagt    120
gtaggtctcc ctaaaacaga ggccaactgg atagatgtaa gatatgacct ggagaaaatt    180
gaaagcctta ttcaatctat tcatattgac accactttat acactgacag tgactttcat    240
cccagttgca aagttactgc aatgaactgc tttctcctgg aattgcaggt tattttacat    300
gagtacagta acatgactct taatgaaaca gtaagaaacg tgctctacct tgcaaacagc    360
```

```
actctgtctt ctaacaagaa tgtagcagaa tctggctgca aggaatgtga ggagctggag    420
gagaaaacct tcacagagtt tttgcaaagc tttatacgca ttgtccaaat gttcatcaac    480
acgtcctgac tgcat                                                    495
```

<210> SEQ ID NO 2
<211> LENGTH: 505
<212> TYPE: DNA
<213> ORGANISM: Homo sapiens IL-15 cDNA

<400> SEQUENCE: 2

```
atgagaattt cgaaaccaca tttgagaagt atttccatcc agtgctactt gtgtttactt     60
ctaaacagtc attttctaac tgaagctggc attcatgtct cattttggg ctgtttcagt     120 gcagggcttc ctaaaacaga agccaactgg gtgaatgtaa taagtgattt gaaaaaaatt     180
gaagatctta ttcaatctat gcatattgat gctactttat atacggaaag tgatgttcac     240
cccagttgca aagtaacagc aatgaagtgc tttctcttgg agttacaagt tatttcactt     300
gagtccggag atgcaagtat tcatgataca gtagaaaatc tgatcatcct agcaaacaac     360
agtttgtctt ctaatgggaa tgtaacagaa tctggatgca agaatgtga ggaactggag     420 gaaaaaaata ttaaagaatt tttgcagagt tttgtacata ttgtccaaat gttcatcaac     480
acttcttgat tgcaattgat tcttt                                          505
```

<210> SEQ ID NO 3
<211> LENGTH: 792
<212> TYPE: DNA
<213> ORGANISM: Mus musculus IL-15 Ra cDNA

<400> SEQUENCE: 3

```
atggcctcgc cgcagctccg gggctatgga gtccaggcca ttcctgtgtt gctgctgctg     60
ctgttgctac tgttgctccc gctgagggtg acgccgggca ccacgtgtcc acctcccgta    120
tctattgagc atgctgacat ccgggtcaag aattacagtg tgaactccag ggagaggtat    180
gtctgtaact ctggctttaa gcggaaagct ggaacatcca ccctgattga gtgtgtgatc    240
aacaagaaca caaatgttgc ccactggaca actcccagcc tcaagtgcat cagagacccc    300
tccctagctc actacagtcc agtgccaaca gtagtgacac caaaggtgac ctcacagcca    360
gagagcccct cccctctgc aaaagagcca gaagctttct ctcccaaatc agataccgca    420
atgaccacag agacagctat tatgcctggc tccaggctga caccatccca aacaacttct    480
gcaggaacta cagggacagg cagtcacaag tcctcccgag ccccatctct tgcagcaaca    540
atgaccttgg agcctacagc ctccacctcc ctcaggataa cagagatttc tccccacagt    600
tccaaaatga cgaaagtggc catctctaca tcggtcctct tggttggtgc agggggttgtg   660 atggctttcc tggcctggta catcaaatca aggcagcctt ctcagccgtg ccgtgttgag    720
gtggaaacca tggaaacagt accaatgact gtgagggcca gcagcaagga ggatgaagac    780
acaggagcct aa                                                       792
```

<210> SEQ ID NO 4
<211> LENGTH: 818
<212> TYPE: DNA
<213> ORGANISM: Homo sapiens IL-15Ra cDNA

<400> SEQUENCE: 4

```
atggcccccgc ggcggggcgcg cggctgccgg accctcggtc tccggcgct gctactgctg     60 ctgctgctcc ggccgccggc gacgcggggc atcacgtgcc ctccccccat gtccgtggaa    120
```

-continued

```
cacgcagaca tctgggtcaa gagctacagc ttgtactcca gggagcggta catttgtaac    180
tctggtttca agcgtaaagc cggcacgtcc agcctgacgg agtgcgtgtt gaacaaggcc    240
acgaatgtcg cccactggac aacccccagt ctcaaatgca ttagagaccc tgccctggtt    300
caccaaaggc cagcgccacc ctccacagta acgacggcag gggtgacccc acagccagag    360
agcctctccc cttctggaaa agagcccgca gcttcatctc ccagctcaaa caacacagcg    420
gccacaacag cagctattgt cccgggctcc cagctgatgc cttcaaaatc accttccaca    480
ggaaccacag agataagcag tcatgagtcc tcccacggca ccccctctca gacaacagcc    540
aagaactggg aactcacagc atccgcctcc caccagccgc aggtgtgta tccacagggc    600 cacagcgaca ccactgtggc tatctccacg tccactgtcc tgctgtgtgg gctgagcgct    660
gtgtctctcc tggcatgcta cctcaagtca aggcaaactc ccccgctggc cagcgttgaa    720
atggaagcca tggaggctct gccggtgact tggggggacca gcagcagaga tgaagacttg    780
gaaaactgct ctcaccacct atgaaactcg gggaaacc                            818
```

<210> SEQ ID NO 5
<211> LENGTH: 162
<212> TYPE: PRT
<213> ORGANISM: Mus musculus IL-15 protein

<400> SEQUENCE: 5

```
Met Lys Ile Leu Lys Pro Tyr Met Arg Asn Thr Ser Ile Ser Cys Tyr
1               5                   10                  15

Leu Cys Phe Leu Leu Asn Ser His Phe Leu Thr Glu Ala Gly Ile His
            20                  25                  30

Val Phe Ile Leu Gly Cys Val Ser Val Gly Leu Pro Lys Thr Glu Ala
        35                  40                  45

Asn Trp Ile Asp Val Arg Tyr Asp Leu Glu Lys Ile Glu Ser Leu Ile
    50                  55                  60

Gln Ser Ile His Ile Asp Thr Thr Leu Tyr Thr Asp Ser Asp Phe His
65                  70                  75                  80

Pro Ser Cys Lys Val Thr Ala Met Asn Cys Phe Leu Leu Glu Leu Gln
                85                  90                  95

Val Ile Leu His Glu Tyr Ser Asn Met Thr Leu Asn Glu Thr Val Arg
            100                 105                 110

Asn Val Leu Tyr Leu Ala Asn Ser Thr Leu Ser Ser Asn Lys Asn Val
        115                 120                 125

Ala Glu Ser Gly Cys Lys Glu Cys Glu Glu Leu Glu Glu Lys Thr Phe
    130                 135                 140

Thr Glu Phe Leu Gln Ser Phe Ile Arg Ile Val Gln Met Phe Ile Asn
145                 150                 155                 160

Thr Ser
```

<210> SEQ ID NO 6
<211> LENGTH: 162
<212> TYPE: PRT
<213> ORGANISM: Homo sapiens IL-15 protein

<400> SEQUENCE: 6

```
Met Arg Ile Ser Lys Pro His Leu Arg Ser Ile Ser Ile Gln Cys Tyr
1               5                   10                  15

Leu Cys Leu Leu Leu Asn Ser His Phe Leu Thr Glu Ala Gly Ile His
            20                  25                  30
```

```
Val Phe Ile Leu Gly Cys Phe Ser Ala Gly Leu Pro Lys Thr Glu Ala
         35                  40                  45

Asn Trp Val Asn Val Ile Ser Asp Leu Lys Lys Ile Glu Asp Leu Ile
 50                  55                  60

Gln Ser Met His Ile Asp Ala Thr Leu Tyr Thr Glu Ser Asp Val His
 65                  70                  75                  80

Pro Ser Cys Lys Val Thr Ala Met Lys Cys Phe Leu Leu Glu Leu Gln
                 85                  90                  95

Val Ile Ser Leu Glu Ser Gly Asp Ala Ser Ile His Asp Thr Val Glu
             100                 105                 110

Asn Leu Ile Ile Leu Ala Asn Asn Ser Leu Ser Ser Asn Gly Asn Val
         115                 120                 125

Thr Glu Ser Gly Cys Lys Glu Cys Glu Glu Leu Glu Glu Lys Asn Ile
130                 135                 140

Lys Glu Phe Leu Gln Ser Phe Val His Ile Val Gln Met Phe Ile Asn
145                 150                 155                 160

Thr Ser

<210> SEQ ID NO 7
<211> LENGTH: 263
<212> TYPE: PRT
<213> ORGANISM: Mus musculus IL-15Ra protein

<400> SEQUENCE: 7

Met Ala Ser Pro Gln Leu Arg Gly Tyr Gly Val Gln Ala Ile Pro Val
 1               5                  10                  15

Leu Leu Leu Leu Leu Leu Leu Leu Leu Pro Leu Arg Val Thr Pro
             20                  25                  30

Gly Thr Thr Cys Pro Pro Pro Val Ser Ile Glu His Ala Asp Ile Arg
         35                  40                  45

Val Lys Asn Tyr Ser Val Asn Ser Arg Glu Arg Tyr Val Cys Asn Ser
 50                  55                  60

Gly Phe Lys Arg Lys Ala Gly Thr Ser Thr Leu Ile Glu Cys Val Ile
 65                  70                  75                  80

Asn Lys Asn Thr Asn Val Ala His Trp Thr Thr Pro Ser Leu Lys Cys
                 85                  90                  95

Ile Arg Asp Pro Ser Leu Ala His Tyr Ser Pro Val Pro Thr Val Val
             100                 105                 110

Thr Pro Lys Val Thr Ser Gln Pro Glu Ser Pro Ser Pro Ser Ala Lys
         115                 120                 125

Glu Pro Glu Ala Phe Ser Pro Lys Ser Asp Thr Ala Met Thr Thr Glu
130                 135                 140

Thr Ala Ile Met Pro Gly Ser Arg Leu Thr Pro Ser Gln Thr Thr Ser
145                 150                 155                 160

Ala Gly Thr Thr Gly Thr Gly Ser His Lys Ser Ser Arg Ala Pro Ser
                 165                 170                 175

Leu Ala Ala Thr Met Thr Leu Glu Pro Thr Ala Ser Thr Ser Leu Arg
             180                 185                 190

Ile Thr Glu Ile Ser Pro His Ser Ser Lys Met Thr Lys Val Ala Ile
         195                 200                 205

Ser Thr Ser Val Leu Leu Val Gly Ala Gly Val Val Met Ala Phe Leu
210                 215                 220

Ala Trp Tyr Ile Lys Ser Arg Gln Pro Ser Gln Pro Cys Arg Val Glu
225                 230                 235                 240
```

Val Glu Thr Met Glu Thr Val Pro Met Thr Val Arg Ala Ser Ser Lys
            245                 250                 255

Glu Asp Glu Asp Thr Gly Ala
            260

<210> SEQ ID NO 8
<211> LENGTH: 267
<212> TYPE: PRT
<213> ORGANISM: Homo sapiens IL-15Ra protein

<400> SEQUENCE: 8

Met Ala Pro Arg Arg Ala Arg Gly Cys Arg Thr Leu Gly Leu Pro Ala
1               5                   10                  15

Leu Leu Leu Leu Leu Leu Leu Arg Pro Pro Ala Thr Arg Gly Ile Thr
            20                  25                  30

Cys Pro Pro Pro Met Ser Val Glu His Ala Asp Ile Trp Val Lys Ser
            35                  40                  45

Tyr Ser Leu Tyr Ser Arg Glu Arg Tyr Ile Cys Asn Ser Gly Phe Lys
        50                  55                  60

Arg Lys Ala Gly Thr Ser Ser Leu Thr Glu Cys Val Leu Asn Lys Ala
65              70                  75                  80

Thr Asn Val Ala His Trp Thr Thr Pro Ser Leu Lys Cys Ile Arg Asp
                85                  90                  95

Pro Ala Leu Val His Gln Arg Pro Ala Pro Pro Ser Thr Val Thr Thr
            100                 105                 110

Ala Gly Val Thr Pro Gln Pro Glu Ser Leu Ser Pro Ser Gly Lys Glu
        115                 120                 125

Pro Ala Ala Ser Ser Pro Ser Ser Asn Asn Thr Ala Ala Thr Thr Ala
130                 135                 140

Ala Ile Val Pro Gly Ser Gln Leu Met Pro Ser Lys Ser Pro Ser Thr
145                 150                 155                 160

Gly Thr Thr Glu Ile Ser Ser His Glu Ser Ser His Gly Thr Pro Ser
                165                 170                 175

Gln Thr Thr Ala Lys Asn Trp Glu Leu Thr Ala Ser Ala Ser His Gln
            180                 185                 190

Pro Pro Gly Val Tyr Pro Gln Gly His Ser Asp Thr Thr Val Ala Ile
        195                 200                 205

Ser Thr Ser Thr Val Leu Leu Cys Gly Leu Ser Ala Val Ser Leu Leu
    210                 215                 220

Ala Cys Tyr Leu Lys Ser Arg Gln Thr Pro Pro Leu Ala Ser Val Glu
225                 230                 235                 240

Met Glu Ala Met Glu Ala Leu Pro Val Thr Trp Gly Thr Ser Ser Arg
                245                 250                 255

Asp Glu Asp Leu Glu Asn Cys Ser His His Leu
            260                 265

<210> SEQ ID NO 9
<211> LENGTH: 268
<212> TYPE: PRT
<213> ORGANISM: Mus musculus IL-2Ra protein

<400> SEQUENCE: 9

Met Glu Pro Arg Leu Leu Met Leu Gly Phe Leu Ser Leu Thr Ile Val
1               5                   10                  15

Pro Ser Cys Arg Ala Glu Leu Cys Leu Tyr Asp Pro Pro Glu Val Pro
            20                  25                  30

Asn Ala Thr Phe Lys Ala Leu Ser Tyr Lys Asn Gly Thr Ile Leu Asn
            35                  40                  45
Cys Glu Cys Lys Arg Gly Phe Arg Arg Leu Lys Glu Leu Val Tyr Met
 50                  55                  60
Arg Cys Leu Gly Asn Ser Trp Ser Ser Asn Cys Gln Cys Thr Ser Asn
 65                  70                  75                  80
Ser His Asp Lys Ser Arg Lys Gln Val Thr Ala Gln Leu Glu His Gln
                 85                  90                  95
Lys Glu Gln Gln Thr Thr Thr Asp Met Gln Lys Pro Thr Gln Ser Met
            100                 105                 110
His Gln Glu Asn Leu Thr Gly His Cys Arg Glu Pro Pro Trp Glu
            115                 120                 125
His Glu Asp Ser Lys Arg Ile Tyr His Phe Val Glu Gly Gln Ser Val
130                 135                 140
His Tyr Glu Cys Ile Pro Gly Tyr Lys Ala Leu Gln Arg Gly Pro Ala
145                 150                 155                 160
Ile Ser Ile Cys Lys Met Lys Cys Gly Lys Thr Gly Trp Thr Gln Pro
                165                 170                 175
Gln Leu Thr Cys Val Asp Glu Arg Glu His His Arg Phe Leu Ala Ser
            180                 185                 190
Glu Glu Ser Gln Gly Ser Arg Asn Ser Ser Pro Glu Ser Glu Thr Ser
            195                 200                 205
Cys Pro Ile Thr Thr Thr Asp Phe Pro Gln Pro Thr Glu Thr Thr Ala
            210                 215                 220
Met Thr Glu Thr Phe Val Leu Thr Met Glu Tyr Lys Val Ala Val Ala
225                 230                 235                 240
Ser Cys Leu Phe Leu Leu Ile Ser Ile Leu Leu Leu Ser Gly Leu Thr
                245                 250                 255
Trp Gln His Arg Trp Arg Lys Ser Arg Arg Thr Ile
            260                 265

<210> SEQ ID NO 10
<211> LENGTH: 169
<212> TYPE: PRT
<213> ORGANISM: Mus musculus IL-2 protein

<400> SEQUENCE: 10

Met Tyr Ser Met Gln Leu Ala Ser Cys Val Thr Leu Thr Leu Val Leu
 1               5                  10                  15
Leu Val Asn Ser Ala Pro Thr Ser Ser Ser Thr Ser Ser Ser Thr Ala
                20                  25                  30
Glu Ala Gln Gln Gln Gln Gln Gln Gln Gln Gln Gln Gln His Leu
            35                  40                  45
Glu Gln Leu Leu Met Asp Leu Gln Glu Leu Leu Ser Arg Met Glu Asn
 50                  55                  60
Tyr Arg Asn Leu Lys Leu Pro Arg Met Leu Thr Phe Lys Phe Tyr Leu
 65                  70                  75                  80
Pro Lys Gln Ala Thr Glu Leu Lys Asp Leu Gln Cys Leu Glu Asp Glu
                 85                  90                  95
Leu Gly Pro Leu Arg His Val Leu Asp Leu Thr Gln Ser Lys Ser Phe
            100                 105                 110
Gln Leu Glu Asp Ala Glu Asn Phe Ile Ser Asn Ile Arg Val Thr Val
            115                 120                 125
Val Lys Leu Lys Gly Ser Asp Asn Thr Phe Glu Cys Gln Phe Asp Asp
            130                 135                 140

```
Glu Ser Ala Thr Val Val Asp Phe Leu Arg Arg Trp Ile Ala Phe Cys
145                 150                 155                 160

Gln Ser Ile Ile Ser Thr Ser Pro Gln
                165

<210> SEQ ID NO 11
<211> LENGTH: 272
<212> TYPE: PRT
<213> ORGANISM: Homo sapiens IL-2Ra protein

<400> SEQUENCE: 11

Met Asp Ser Tyr Leu Leu Met Trp Gly Leu Leu Thr Phe Ile Met Val
1               5                   10                  15

Pro Gly Cys Gln Ala Glu Leu Cys Asp Asp Pro Pro Glu Ile Pro
            20                  25                  30

His Ala Thr Phe Lys Ala Met Ala Tyr Lys Glu Gly Thr Met Leu Asn
            35                  40                  45

Cys Glu Cys Lys Arg Gly Phe Arg Arg Ile Lys Ser Gly Ser Leu Tyr
    50                  55                  60

Met Leu Cys Thr Gly Asn Ser Ser His Ser Ser Trp Asp Asn Gln Cys
65                  70                  75                  80

Gln Cys Thr Ser Ser Ala Thr Arg Asn Thr Thr Lys Gln Val Thr Pro
                85                  90                  95

Gln Pro Glu Glu Gln Lys Glu Arg Lys Thr Thr Glu Met Gln Ser Pro
            100                 105                 110

Met Gln Pro Val Asp Gln Ala Ser Leu Pro Gly His Cys Arg Glu Pro
            115                 120                 125

Pro Pro Trp Glu Asn Glu Ala Thr Glu Arg Ile Tyr His Phe Val Val
130                 135                 140

Gly Gln Met Val Tyr Tyr Gln Cys Val Gln Gly Tyr Arg Ala Leu His
145                 150                 155                 160

Arg Gly Pro Ala Glu Ser Val Cys Lys Met Thr His Gly Lys Thr Arg
                165                 170                 175

Trp Thr Gln Pro Gln Leu Ile Cys Thr Gly Glu Met Glu Thr Ser Gln
            180                 185                 190

Phe Pro Gly Glu Glu Lys Pro Gln Ala Ser Pro Glu Gly Arg Pro Glu
            195                 200                 205

Ser Glu Thr Ser Cys Leu Val Thr Thr Thr Asp Phe Gln Ile Gln Thr
        210                 215                 220

Glu Met Ala Ala Thr Met Glu Thr Ser Ile Phe Thr Thr Glu Tyr Gln
225                 230                 235                 240

Val Ala Val Ala Gly Cys Val Phe Leu Leu Ile Ser Val Leu Leu Leu
                245                 250                 255

Ser Gly Leu Thr Trp Gln Arg Arg Gln Arg Lys Ser Arg Arg Thr Ile
            260                 265                 270

<210> SEQ ID NO 12
<211> LENGTH: 153
<212> TYPE: PRT
<213> ORGANISM: Homo sapiens IL-2 protein

<400> SEQUENCE: 12

Met Tyr Arg Met Gln Leu Leu Ser Cys Ile Ala Leu Ser Leu Ala Leu
1               5                   10                  15

Val Thr Asn Ser Ala Pro Thr Ser Ser Ser Thr Lys Lys Thr Gln Leu
            20                  25                  30
```

```
Gln Leu Glu His Leu Leu Asp Leu Gln Met Ile Leu Asn Gly Ile
         35                  40                  45

Asn Asn Tyr Lys Asn Pro Lys Leu Thr Arg Met Leu Thr Phe Lys Phe
 50                  55                  60

Tyr Met Pro Lys Lys Ala Thr Glu Leu Lys His Leu Gln Cys Leu Glu
 65                  70                  75                  80

Glu Glu Leu Lys Pro Leu Glu Glu Val Leu Asn Leu Ala Gln Ser Lys
                 85                  90                  95

Asn Phe His Leu Arg Pro Arg Asp Leu Ile Ser Asn Ile Asn Val Ile
                100                 105                 110

Val Leu Glu Leu Lys Gly Ser Glu Thr Thr Phe Met Cys Glu Tyr Ala
                115                 120                 125

Asp Glu Thr Ala Thr Ile Val Glu Phe Leu Asn Arg Trp Ile Thr Phe
130                 135                 140

Cys Gln Ser Ile Ile Ser Thr Leu Thr
145                 150
```

<210> SEQ ID NO 13
<211> LENGTH: 4367
<212> TYPE: DNA
<213> ORGANISM: Mus musculus IL-2Ra cDNA

<400> SEQUENCE: 13

```
gacattgtct aaaagccaag atgacagact gagaggcctg agcccttgtt ctggcattct      60
cccaggaaga tgcagtaaag gggttgaccc aatatactgc agagaatttc atccagttcc     120
ctcctccatc ctgatcccat gtgccaggaa gatggagcca cgcttgctga tgttggggtt     180
tctctcatta accatagtac ccagttgtcg ggcagaactg tgtctgtatg acccacccga     240
ggtccccaat gccacattca agccctctc ctacaagaac ggcaccatcc taaactgtga      300
atgcaagaga ggtttccgaa gactaaagga attggtctat atgcgttgct taggaaactc     360
ctggagcagc aactgccagt gcaccagcaa ctcccatgac aaatcgagaa agcaagttac     420
agctcaactt gaacaccaga agagcaacaa accacaaca gacatgcaga agccaacaca      480
gtctatgcac caagagaacc ttacaggtca ctgcagggag ccacctcctt gggaacatga     540
agattccaag agaatctatc atttcgtgga aggacagagt gttcactacg agtgtattcc     600
gggatacaag gctctacaga gaggtcctgc tattagcatc tgcaagatga agtgtgggaa     660
aacgggtgg actcagcccc agctcacatg tgtagatgaa agagaacacc accgatttct     720
ggctagtgag gaatctcaag gaagcagaaa ttcttctccc gagagtgaga cttcctgccc     780
cataaccacc acagacttcc cacaaccccac agaaacaact gcaatgacgg agacatttgt     840
gctcacaatg gagtataagg tagcagtggc cagctgcctc ttcctgctca tcagcatcct     900
cctcctgagc gggctcacct ggcaacacag atggaggaag agcagaagaa ccatctagca     960
agctagaaaa gtcagagccc aggcaagcgg atgggaatca caaagctcaa gccaaatctg    1020
agacgccaag cattcaccta acggctgttt ccttctgatc cctgggttc tagaacattc     1080
tgaagtcaca ggacataaca gcaactctat cactaaactg gactttgcca ttgaagaata    1140
ggatctaacc acttcagcac agcagttcta aagctttaat gggagagagg cccaacagt     1200
gctctgtgtg tttgttttt gtgtatatct gttgatggga gctgagatgg tgtggtcact    1260
tttcatgtaa catatagtat agaaaaagta gctttaggtt gacttcattg ttacaaccca    1320
gtttggaaag cccaagtaaa actcagcact aatgtaaata ttcctcctc ctcctcctct     1380
```

```
ctcttttcat cctccgctcc atcttcctct tcttcctcct cctttccac ctcctctgtc    1440
cctacccacc cccacccatc cactttcctt cttccttct gctctcacaa gctcatccta    1500
gctacacgtg catggctggc tccttttca acctctgttt gcctaactgg ctcttctgat    1560
ttcatcactt actgatcagc ctttaaaact ctgagctggc aaagatgact ctatctatgt    1620
tcttggctca gtcccagaag gaaacccct tttcatgaag cttcagtttt gacatcctga    1680
agaacagaaa ctgtggcaga acaatcttca gataacatca aaacaaagtg agaagccac    1740
gggaactgtg gagctctggt attcagaagc ctgtgtctag ggtctgcgcc aggagcagaa    1800
ggctgaagga agtcccagga cgtggactta gatgctttcc cagcaggcca ctctaagcgc    1860
tggtttcttt gggacagctg tcaattgtac gctcaattta gcctgcacta atctgatgct    1920
tacaggtgaa cactcaaggc acaggtatga acttggtaca taccgtgaaa cactggaaa    1980
gaaaagaata ctttcaagtt tacagaagga aggaaggaaa aaggaagcag aggtggtgat    2040
tatacaaaag attagctgta gactggatat cccaggcatc ctcggataat gccccgccc    2100
cagcaccctg atccaggtca ccaaagcctt gtgagatcag actgcagagc cagtctgtct    2160
ctgagtcagt aaatgtagaa tttggatttc tcacaagttc ctggcggtgt cttttttt    2220
tttaatattt tttattaggt attttcctca tttacatttc caatgctatc ccaaaagtcc    2280
cccatacct ccccccacact cccctaccca cccactccca cttttggcc ctggtgttcc    2340
cctgtactgg ggcatataaa gtttgcaagt cctggtggtg tctttatgct gatctctagc    2400
ccacactttg tgaggcactg ggctatccca gtgtgctctc ctcttccaca gataccaaaa    2460
gcacctgggt tgatgctca gacttctgag cacgttcttg ttcaatctct tgcgtaagat    2520
ttcctctcag atgagttgag tcagattctc atgtttaaca gtgttttagg ggattcacag    2580
aagcccaaac tatcagtttt catttctgaa aaggctggaa aatttatga aaaactttca    2640
aaggtcagac agagccattt tgagtctttt atgtgaccaa gtatgaacca gatcttcct    2700
atctatggtc tcccctttcc aaaatatatc ttttgtgggg acacggcaag gaggaaagtt    2760
aaatagaatc tcaagctact aattttagaa aagaaaaaa tattaaactc ttactaaaga    2820
gctgtgggta gtggtacaca cctgtaagcc cagctctcag gagactgagg caggaggatt    2880
gcagtgagtc agagatcagc ttcacctaca agcaaaaccc tgccttaccc ctcaacctt    2940
ccataaaaac agtcttactt gtgtaaaatt aattttaat acatatttgt gcacgatgtg    3000
tgtgcctggt gcccagggaa gccaaaaaaa tatgttcaat gtccctggaa taggtggtta    3060
tgagctgcca tggaggtgat gggatttaaa cccctgttct ctgaaaaagc agctagttct    3120
cttaaccact gagccatctc tacagcccca ttaaattgaa ttttattgtc attactcaat    3180
atgggagatg gggtaatgat aacaattttt tttttataat actaagatgt ttagctattt    3240
tactctcctt cacaagtgta gagtagaatt ttctagaagc tacatgcatg atattatcgc    3300
tctggtgtta acacataatg gatttatctt gttaataaaa gaattagtaa ataatatttt    3360
aaattttttc tttgttttag ttttaagatg attaatatct atagatacta gtgtacatta    3420
agaaagcctt tgggatcctc aatcattttg catggtttta gtaatttttt aataacataa    3480
agaaggtctg acagattatg ctaaagagct attgtggtat ggattagaaa tggcccccac    3540
aggctcctgt gttcaaacat cagctagcag tgctgctttg ggttttggaa cctttaagag    3600
gtggggcctt gcttaaggag ataggtcact ggaggtgaac cagacttgct tccagtctcc    3660
ctctctgctg tcccaggaag ccatcatatg aggagtttca caacatactt ctgctgccac    3720
agagtccctc cagtaaggca cgtactggcc actgtgtagt gtaccctcta aaactgagct    3780
```

```
agagctcccc tctcctccct acactatctc tgttgatgct ttgtcacggt gatgaagaac    3840
ataagtaagg caaagacaag acatagtttg gagactcacg tgagcatctc agccagactc    3900
aggcacagct gcgatgtggg aattatcaag catgagatgc aaagcaatgg aaaatgaatc    3960
gttatgacag aagcctacat ctagtcttcc cttcttccca ttagtaataa tagcccgtgt    4020
tttagaagaa cacatctttt tggtgttcta ggtagcttat attgcaaatg tggcacaatc    4080
taagagaaat ctgggatgag ggaacctcag tgaaagattc tccttgatca gattgtccca    4140
ctgatgattg atatgggaag gcccaaccca ctgtgaaagg caccacccat tggcaggatg    4200
actggggtta tagaagcaaa caggctgagc atgagccagt gagcaagcca gtaagcagtg    4260
gcttctcttt ggaagaagca tggctttctt ccgtggcttc tgtttgatct ctctcaatga    4320
tagattgtga cctagaagta taagctaaaa taaaccattt cttaccc                  4367
```

<210> SEQ ID NO 14
<211> LENGTH: 939
<212> TYPE: DNA
<213> ORGANISM: Mus musculus IL-2 cDNA

<400> SEQUENCE: 14

```
atcacccttg ctaatcactc ctcacagtga cctcaagtcc tgcaggcatg tacagcatgc     60
agctcgcatc ctgtgtcaca ttgacacttg tgctccttgt caacagcgca cccacttcaa    120
gctccacttc aagctctaca gcggaagcac agcagcagca gcagcagcag cagcagcagc    180
agcagcacct ggagcagctg ttgatggacc tacaggagct cctgagcagg atggagaatt    240
acaggaacct gaaactcccc aggatgctca ccttcaaatt ttacttgccc aagcaggcca    300
cagaattgaa agatcttcag tgcctagaag atgaacttgg acctctgcgg catgttctgg    360
atttgactca aagcaaaagc tttcaattgg aagatgctga aatttcatc agcaatatca     420 gagtaactgt tgtaaaacta aagggctctg acaacacatt tgagtgccaa ttcgatgatg    480
agtcagcaac tgtggtggac tttctgagga gatggatagc cttctgtcaa agcatcatct    540
caacaagccc tcaataacta tgtacctcct gcttacaaca cataaggctc tctatttatt    600
taaatattta actttaattt attttttggat gtattgttta ctatcttttg taactactag    660
tcttcagatg ataaatatgg atcttttaaag attcttttg taagccccaa gggctcaaaa    720
atgttttaaa ctatttatct gaaattattt attatattga attgttaaat atcatgtgta    780
ggtagactca ttaataaaag tatttagatg attcaaatat aaataagctc agatgtctgt    840 cattttagg acagcacaaa gtaagcgcta aaataacttc tcagttattc ctgtgaactc    900
tatgttaatc agtgttttca agaaataaag ctctcctct                           939
```

<210> SEQ ID NO 15
<211> LENGTH: 1047
<212> TYPE: DNA
<213> ORGANISM: Homo sapiens IL-2 cDNA

<400> SEQUENCE: 15

```
cgaattcccc tatcacctaa gtgtgggcta atgtaacaaa gagggatttc acctacatcc     60
attcagtcag tctttggggg tttaaagaaa ttccaaagag tcatcagaag aggaaaaatg    120
aaggtaatgt ttttttcagac aggtaaagtc tttgaaaata tgtgtaatat gtaaaacatt    180
ttgcaccccc cataatattt ttccagaatt aacagtataa attgcatctc ttgttcaaga    240
gttccctatc actctcttta atcactactc acagtaacct caactcctgc cacaatgtac    300
```

-continued

| | |
|---|---|
| aggatgcaac tcctgtcttg cattgcacta agtcttgcac ttgtcacaaa cagtgcacct | 360 |
| acttcaagtt ctacaaagaa aacacagcta caactggagc atttactgct ggatttacag | 420 |
| atgattttga atggaattaa taattacaag aatcccaaac tcaccaggat gctcacattt | 480 |
| aagttttaca tgcccaagaa ggccacagaa ctgaaacatc ttcagtgtct agaagaagaa | 540 |
| ctcaaacctc tggaggaagt gctaaattta gctcaaagca aaactttca cttaagaccc | 600 |
| agggacttaa tcagcaatat caacgtaata gttctggaac taaagggatc tgaaacaaca | 660 |
| ttcatgtgtg aatatgctga tgagacagca accattgtag aatttctgaa cagatggatt | 720 |
| acctttgtc aaagcatcat ctcaacactg acttgataat taagtgcttc ccacttaaaa | 780 |
| catatcaggc cttctattta tttaaatatt taaattttat atttattgtt gaatgtatgg | 840 |
| tttgctacct attgtaacta ttattcttaa tcttaaaact ataaatatgg atcttttatg | 900 |
| attcttttg taagccctag gggctctaaa atggtttcac ttatttatcc caaaatattt | 960 |
| attattatgt tgaatgttaa atatagtatc tatgtagatt ggttagtaaa actatttaat | 1020 |
| aaatttgata aatataaaaa aaaaaaa | 1047 |

<210> SEQ ID NO 16
<211> LENGTH: 2308
<212> TYPE: DNA
<213> ORGANISM: Homo sapiens IL-2Ra cDNA

<400> SEQUENCE: 16

| | |
|---|---|
| gagagactgg atggacccac aagggtgaca gcccaggcgg accgatcttc ccatcccaca | 60 |
| tcctccggcg cgatgccaaa agaggctga cggcaactgg gccttctgca gagaaagacc | 120 |
| tccgcttcac tgccccggct ggtcccaagg gtcaggaaga tggattcata cctgctgatg | 180 |
| tggggactgc tcacgttcat catggtgcct ggctgccagg cagagctctg tgacgatgac | 240 |
| ccgccagaga tcccacacgc cacattcaaa gccatggcct acaaggaagg aaccatgttg | 300 |
| aactgtgaat gcaagagagg tttccgcaga ataaaaagcg ggtcactcta tatgctctgt | 360 |
| acaggaaact ctagccactc gtcctgggac aaccaatgtc aatgcacaag ctctgccact | 420 |
| cggaacacaa cgaaacaagt gacacctcaa cctgaagaac agaagaaag gaaaaccaca | 480 |
| gaaatgcaaa gtccaatgca gccagtggac caagcgagcc ttccaggtca ctgcagggaa | 540 |
| cctccaccat gggaaaatga agccacagag agaatttatc atttcgtggt ggggcagatg | 600 |
| gtttattatc agtgcgtcca gggatacagg gctctacaca gaggtcctgc tgagagcgtc | 660 |
| tgcaaaatga cccacgggaa gacaaggtgg acccagcccc agctcatatg cacaggtgaa | 720 |
| atggagacca gtcagtttcc aggtgaagag aagcctcagg caagcccga aggccgtcct | 780 |
| gagagtgaga cttcctgcct cgtcacaaca acagattttc aaatacagac agaaatggct | 840 |
| gcaaccatgg agacgtccat atttacaaca gagtaccagg tagcagtggc cggctgtgtt | 900 |
| ttcctgctga tcagcgtcct cctcctgagt gggctcacct ggcagcggag acagaggaag | 960 |
| agtagaagaa caatctagaa aaccaaaaga acaagaattt cttggtaaga agccgggaac | 1020 |
| agacaacaga agtcatgaag cccaagtgaa atcaaggtg ctaaatggtc gcccaggaga | 1080 |
| catccgttgt gcttgcctgc gttttggaag ctctgaagtc acatcacagg acacggggca | 1140 |
| gtggcaacct tgtctctatg ccagctcagt cccatcagag agcgagcgct acccacttct | 1200 |
| aaatagcaat ttcgccgttg aagaggaagg gcaaaaccac tagaactctc atcttatttt | 1260 |
| tcatgtatat gtgttcatta aagcatgaat ggtatgaac tctctccacc ctatatgtag | 1320 |
| tataaagaaa agtaggttta cattcatctc attccaactt cccagttcag gagtcccaag | 1380 |

```
gaaagcccca gcactaacgt aaatacacaa cacacacact ctaccctata caactggaca    1440
ttgtctgcgt ggttcctttc tcagccgctt ctgactgctg attctcccgt tcacgttgcc    1500
taataaacat ccttcaagaa ctctgggctg ctacccagaa atcattttac ccttggctca    1560
atcctctaag ctaaccccct tctactgagc cttcagtctt gaatttctaa aaaacagagg    1620
ccatggcaga ataatctttg ggtaacttca aaacggggca gccaaaccca tgaggcaatg    1680
tcaggaacag aaggatgaat gaggtcccag gcagagaatc atacttagca aagttttacc    1740
tgtgcgttac taattggcct ctttaagagt tagtttcttt gggattgcta tgaatgatac    1800
cctgaatttg gcctgcacta atttgatgtt tacaggtgga cacacaaggt gcaaatcaat    1860
gcgtacgttt cctgagaagt gtctaaaaac accaaaaagg gatccgtaca ttcaatgttt    1920
atgcaaggaa ggaaagaaag aaggaagtga agagggagaa gggatggagg tcacactggt    1980
agaacgtaac cacggaaaag agcgcatcag gcctggcacg gtggctcagg cctataaccc    2040
cagctcccta ggagaccaag gcgggagcat ctcttgaggc caggagtttg agaccagcct    2100
gggcagcata gcaagacaca tccctacaaa aaattagaaa ttggctggat gtggtggcat    2160
acgcctgtag tcctagccac tcaggaggct gaggcaggag gattgcttga gcccaggagt    2220
tcgaggctgc agtcagtcat gatggcacca ctgcactcca gcctgggcaa cagagcaaga    2280
tcctgtcttt aaggaaaaaa agacaagg                                       2308
```